(12) United States Patent
Zhao et al.

(10) Patent No.: US 11,939,578 B2
(45) Date of Patent: Mar. 26, 2024

(54) DOUBLE-STRANDED RNA MOLECULE TARGETING CKIP-1 AND USE THEREOF

(71) Applicant: BEIJING TIDE PHARMACEUTICAL CO., LTD., Beijing (CN)

(72) Inventors: Yanping Zhao, Beijing (CN); Hongjun Wang, Beijing (CN); Yuanyuan Jiang, Beijing (CN); Weiting Zhong, Beijing (CN); Jianmei Pang, Beijing (CN); Gong Li, Beijing (CN); Xiang Li, Beijing (CN); Yixin He, Beijing (CN); Liying Zhou, Beijing (CN); Yanan Liu, Beijing (CN)

(73) Assignee: BEIJING TIDE PHARMACEUTICAL CO., LTD., Beijing (CN)

( * ) Notice: Subject to any disclaimer, the term of this patent is extended or adjusted under 35 U.S.C. 154(b) by 2 days.

(21) Appl. No.: 17/474,396

(22) Filed: Sep. 14, 2021

(65) Prior Publication Data
US 2022/0064645 A1 Mar. 3, 2022

Related U.S. Application Data

(62) Division of application No. 16/644,977, filed as application No. PCT/CN2018/104552 on Sep. 7, 2018, now Pat. No. 11,155,819.

(30) Foreign Application Priority Data

Sep. 7, 2017 (WO) ............... PCT/CN2017/100863
Sep. 7, 2017 (WO) ............... PCT/CN2017/100864
Sep. 7, 2017 (WO) ............... PCT/CN2017/100865
Sep. 7, 2017 (WO) ............... PCT/CN2017/100866
Sep. 7, 2017 (WO) ............... PCT/CN2017/100867

(51) Int. Cl.
| C07H 21/04 | (2006.01) |
| A61P 19/02 | (2006.01) |
| A61P 19/08 | (2006.01) |
| A61P 29/00 | (2006.01) |
| C12N 15/113 | (2010.01) |
| C12N 15/85 | (2006.01) |
| A61K 48/00 | (2006.01) |

(52) U.S. Cl.
CPC ............ *C12N 15/113* (2013.01); *A61P 19/02* (2018.01); *A61P 19/08* (2018.01); *A61P 29/00* (2018.01); *C12N 15/85* (2013.01); *A61K 48/00* (2013.01); *C12N 2310/14* (2013.01); *C12N 2310/314* (2013.01); *C12N 2310/315* (2013.01); *C12N 2310/321* (2013.01); *C12N 2310/322* (2013.01); *C12N 2310/334* (2013.01); *C12N 2310/335* (2013.01)

(58) Field of Classification Search
None
See application file for complete search history.

(56) References Cited

U.S. PATENT DOCUMENTS

| 7,691,997 B2 | 4/2010 | Khvorova et al. |
| 7,750,144 B2 | 7/2010 | Zamore et al. |
| 2007/0135372 A1 | 6/2007 | MacLachlan et al. |
| 2016/0272967 A1 | 9/2016 | Zhang et al. |

FOREIGN PATENT DOCUMENTS

| EP | 2213738 | 8/2010 |
| EP | 3018209 | 5/2016 |
| WO | 2015027895 | 3/2015 |

OTHER PUBLICATIONS

Shaikh AB. "Role of CKIP-1 in suppression of osteoblast mediated bone repair in a collagen induced non-human primate arthritis model." Dec. 1, 2017, pp. 1-82.
International Search Report of Int'l Appl. No. PCT/CN2018/104552, dated Dec. 5, 2018.
Chen et al. "MicroRNA-20a Promotes Osteogenic Differentiation of C3H/10T1/2 Cells through Regulating CKIP-1 Expression." Journal of Experimental Hematology. Feb. 2017;25(1):214-220. (abstract).
Guo et al. "Therapeutic RNA interference targeting CKIP-1 with a cross-species sequence to stimulate bone formation." Bone. Feb. 1, 2014;59:76-88.

*Primary Examiner* — Kimberly Chong
(74) *Attorney, Agent, or Firm* — Robin L. Teskin; Baker, Donelson, Bearman, Caldwell & Berkowitz PC

(57) ABSTRACT

The present invention relates to the field of biomedicine, particularly to double-stranded RNA molecules targeting CKIP-1 and uses thereof, particularly to use of the double-stranded RNA molecules for the treatment of inflammatory diseases such as arthritis, particularly rheumatoid arthritis.

14 Claims, 13 Drawing Sheets

Specification includes a Sequence Listing.

| siRNA | sense strand (5'-3') Sequence | SEQ ID NO | antisense strand (5'-3') Sequence | SEQ ID NO |
|---|---|---|---|---|
| si-TD029 | CGCCCGAGAAGGUCGGCUGUU | 193 | CAGCCGACCUUCUCGGGCGTT | 194 |
| si-TD030 | GCCCGAGAAGGUCGGCUGGTT | 195 | CCAGCCGACCUUCUCGGGCTT | 196 |
| si-TD031 | CCCGAGAAGGUCGGCUGGGTT | 197 | CCCAGCCGACCUUCUCGGGTT | 198 |
| si-TD032 | CCGAGAAGGUCGGCUGGGUTT | 199 | ACCCAGCCGACCUUCUCGGTT | 200 |
| si-TD033 | CGAGAAGGUCGGCUGGGUCTT | 201 | GACCCAGCCGACCUUCUCGTT | 202 |
| si-TD034 | GAGAAGGUCGGCUGGGUCCTT | 203 | GGACCCAGCCGACCUUCUCTT | 204 |
| si-TD035 | AGAAGGUCGGCUGGGUCCGTT | 205 | CGGACCCAGCCGACCUUCUTT | 206 |
| si-TD036 | GAAGGUCGGCUGGGUCCGGTT | 207 | CCGGACCCAGCCGACCUUCTT | 208 |
| si-TD037 | AAGGUCGGCUGGGUCCGGATT | 209 | UCCGGACCCAGCCGACCUUTT | 210 |
| si-TD038 | AGGUCGGCUGGGUCCGGAATT | 211 | UUCCGGACCCAGCCGACCUTT | 212 |
| si-TD040 | GUCGGCUGGGUCCGGAAAUTT | 213 | AUUCCGGACCCAGCCGACTT | 214 |
| si-TD041 | UCGGCUGGGUCCGGAAAUUTT | 215 | AAUUCCGGACCCAGCCGATT | 216 |
| si-TD042 | CGGCUGGGUCCGGAAAUUCTT | 217 | GAAUUCCGGACCCAGCCGTT | 218 |
| si-TD043 | GGCUGGGUCCGGAAAUUCUTT | 219 | AGAAUUCCGGACCCAGCCTT | 220 |
| si-TD044 | GCUGGGUCCGGAAAUUCUGTT | 221 | CAGAAUUCCGGACCCAGCTT | 222 |
| si-TD045 | CUGGGUCCGGAAAUUCUGCTT | 223 | GCAGAAUUCCGGACCCAGTT | 224 |
| si-TD046 | UGGGUCCGGAAAUUCUGCGTT | 225 | CGCAGAAUUCCGGACCCATT | 226 |
| si-TD047 | GGGUCCGGAAAUUCUGCGGTT | 227 | CCGCAGAAUUCCGGACCCTT | 228 |
| si-TD048 | GGUCCGGAAAUUCUGCGGGTT | 229 | CCCGCAGAAUUCCGGACCTT | 230 |
| si-TD049 | GUCCGGAAAUUCUGCGGGATT | 231 | UCCCGCAGAAUUCCGGACTT | 232 |
| si-TD050 | UCCGGAAAUUCUGCGGGAATT | 233 | UUCCCGCAGAAUUCCGGATT | 234 |
| si-TD052 | CGGAAAUUCUGCGGGAAAGTT | 235 | CUUUCCGCAGAAUUUCCGTT | 236 |
| si-TD053 | GGAAAUUCUGCGGGAAAGGTT | 237 | CCUUUCCGCAGAAUUCCTT | 238 |
| si-TD054 | GAAAUUCUGCGGGAAAGGGTT | 239 | CCCUUUCCGCAGAAUUUCTT | 240 |
| si-TD055 | AAAUUCUGCGGGAAAGGGATT | 241 | UCCCUUUCCGCAGAAUUUTT | 242 |
| si-TD056 | AAUUCUGCGGGAAAGGGAUTT | 243 | AUCCCUUUCCGCAGAAUUTT | 244 |
| si-TD057 | AUUCUGCGGGAAAGGGAUUTT | 245 | AAUCCCUUUCCGCAGAAUTT | 246 |
| si-TD058 | UUCUGCGGGAAAGGGAUUUTT | 247 | AAAUCCCUUUCCGCAGAATT | 248 |
| si-TD059 | UCUGCGGGAAAGGGAUUUUTT | 249 | AAAAUCCCUUUCCGCAGATT | 250 |
| si-TD060 | CUGCGGGAAAGGGAUUUUCTT | 251 | GAAAAUCCCUUUCCGCAGTT | 252 |
| si-TD061 | UGCGGGAAAGGGAUUUUCATT | 253 | UGAAAAUCCCUUUCCGCATT | 254 |
| si-TD062 | GCGGGAAAGGGAUUUUCAGTT | 255 | CUGAAAAUCCCUUUCCGCTT | 256 |
| si-TD063 | CGGGAAAGGGAUUUUCAGGTT | 257 | CCUGAAAAUCCCUUUCCGTT | 258 |
| si-TD064 | GGGAAAGGGAUUUUCAGGGTT | 259 | CCCUGAAAAUCCCUUUCCTT | 260 |
| si-TD065 | GGAAAGGGAUUUUCAGGGATT | 261 | UCCCUGAAAAUCCCUUUCTT | 262 |
| si-TD066 | GAAAGGGAUUUUCAGGGAGTT | 263 | CUCCCUGAAAAUCCCUUUCTT | 264 |
| si-TD067 | AAAGGGAUUUUCAGGGAGATT | 265 | UCUCCCUGAAAAUCCCUUUTT | 266 |
| si-TD068 | AAGGGAUUUUCAGGGAGAUTT | 267 | AUCUCCCUGAAAAUCCCUUTT | 268 |
| si-TD069 | AGGGAUUUUCAGGGAGAUUTT | 269 | AAUCUCCCUGAAAAUCCCUTT | 270 |
| si-TD070 | GGGAUUUUCAGGGAGAUUUTT | 271 | AAAUCUCCCUGAAAAUCCCTT | 272 |
| si-TD071 | GGAUUUUCAGGGAGAUUUGTT | 273 | CAAAUCUCCCUGAAAAUCCTT | 274 |

Fig. 1A

| | | | | |
|---|---|---|---|---|
| si-TD072 | GAUUUUCAGGGAGAUUUGGTT | 275 | CCAAAUCUCCCUGAAAAUCTT | 276 |
| si-TD073 | AUUUUCAGGGAGAUUUGGATT | 277 | UCCAAAUCUCCCUGAAAAUTT | 278 |
| si-TD074 | UUUUCAGGGAGAUUUGGAATT | 279 | UUCCAAAUCUCCCUGAAAATT | 280 |
| si-TD075 | UUUCAGGGAGAUUUGGAAATT | 281 | UUUCCAAAUCUCCCUGAAATT | 282 |
| si-TD076 | UUCAGGGAGAUUUGGAAAATT | 283 | UUUUCCAAAUCUCCCUGAATT | 284 |
| si-TD077 | UCAGGGAGAUUUGGAAAAATT | 285 | UUUUUCCAAAUCUCCCUGATT | 286 |
| si-TD078 | CAGGGAGAUUUGGAAAAACTT | 287 | GUUUUUCCAAAUCUCCCUGTT | 288 |
| si-TD079 | AGGGAGAUUUGGAAAAACCTT | 289 | GGUUUUUCCAAAUCUCCCUTT | 290 |
| si-TD080 | GGGAGAUUUGGAAAAACCGTT | 291 | CGGUUUUUCCAAAUCUCCCTT | 292 |
| si-TD081 | GGAGAUUUGGAAAAACCGCTT | 293 | GCGGUUUUUCCAAAUCUCCTT | 294 |
| si-TD082 | GAGAUUUGGAAAAACCGCUTT | 295 | AGCGGUUUUUCCAAAUCUCTT | 296 |
| si-TD083 | AGAUUUGGAAAAACCGCUATT | 297 | UAGCGGUUUUUCCAAAUCUTT | 298 |
| si-TD084 | GAUUUGGAAAAACCGCUAUTT | 299 | AUAGCGGUUUUUCCAAAUCTT | 300 |
| si-TD085 | AUUUGGAAAAACCGCUAUGTT | 301 | CAUAGCGGUUUUUCCAAAUTT | 302 |
| si-TD086 | UUUGGAAAAACCGCUAUGUTT | 303 | ACAUAGCGGUUUUUCCAAATT | 304 |
| si-TD087 | UUGGAAAAACCGCUAUGUGTT | 305 | CACAUAGCGGUUUUUCCAATT | 306 |
| si-TD088 | UGGAAAAACCGCUAUGUGGTT | 307 | CCACAUAGCGGUUUUUCCATT | 308 |
| si-TD089 | GGAAAAACCGCUAUGUGGUTT | 309 | ACCACAUAGCGGUUUUUCCTT | 310 |
| si-TD090 | GAAAAACCGCUAUGUGGUGTT | 311 | CACCACAUAGCGGUUUUUCTT | 312 |
| si-TD091 | AAAAACCGCUAUGUGGUGCTT | 313 | GCACCACAUAGCGGUUUUUTT | 314 |
| si-TD092 | AAAACCGCUAUGUGGUGCUTT | 315 | AGCACCACAUAGCGGUUUUTT | 316 |
| si-TD093 | AAACCGCUAUGUGGUGCUGTT | 317 | CAGCACCACAUAGCGGUUUTT | 318 |
| si-TD094 | AACCGCUAUGUGGUGCUGATT | 319 | UCAGCACCACAUAGCGGUUTT | 320 |
| si-TD096 | CCGCUAUGUGGUGCUGAAATT | 321 | UUUCAGCACCACAUAGCGGTT | 322 |
| si-TD097 | CGCUAUGUGGUGCUGAAAGTT | 323 | CUUUCAGCACCACAUAGCGTT | 324 |
| si-TD098 | GCUAUGUGGUGCUGAAAGGTT | 325 | CCUUUCAGCACCACAUAGCTT | 326 |
| si-TD136 | GAGAAGGAGGUAAAAGAUGTT | 327 | CAUCUUUUACCUCCUUCUCTT | 328 |
| si-TD137 | AGAAGGAGGUAAAAGAUGATT | 329 | UCAUCUUUUACCUCCUUCUTT | 330 |
| si-TD138 | GAAGGAGGUAAAAGAUGAGTT | 331 | CUCAUCUUUUACCUCCUUCTT | 332 |
| si-TD139 | AAGGAGGUAAAAGAUGAGATT | 333 | UCUCAUCUUUUACCUCCUUTT | 334 |
| si-TD140 | AGGAGGUAAAAGAUGAGAATT | 335 | UUCUCAUCUUUUACCUCCUTT | 336 |
| si-TD141 | GGAGGUAAAAGAUGAGAAATT | 337 | UUUCUCAUCUUUUACCUCCTT | 338 |
| si-TD142 | GAGGUAAAAGAUGAGAAAATT | 339 | UUUUCUCAUCUUUUACCUCTT | 340 |
| si-TD143 | AGGUAAAAGAUGAGAAAAATT | 341 | UUUUUCUCAUCUUUUACCUTT | 342 |
| si-TD182 | UGAGUGACUAUGAGAAGUGTT | 343 | CACUUCUCAUAGUCACUCATT | 344 |
| si-TD181 | CUGAGUGACUAUGAGAAGUTT | 345 | ACUUCUCAUAGUCACUCAGTT | 346 |
| si-TD179 | ACCUGAGUGACUAUGAGAATT | 347 | UUCUCAUAGUCACUCAGGUTT | 348 |
| si-TD178 | GACCUGAGUGACUAUGAGATT | 349 | UCUCAUAGUCACUCAGGUCTT | 350 |
| si-TD177 | UGACCUGAGUGACUAUGAGTT | 351 | CUCAUAGUCACUCAGGUCATT | 352 |
| si-TD176 | UUGACCUGAGUGACUAUGATT | 353 | UCAUAGUCACUCAGGUCAATT | 354 |
| si-TD175 | UUUGACCUGAGUGACUAUGTT | 355 | CAUAGUCACUCAGGUCAAATT | 356 |
| si-TD224 | GCAGGAGCAAGAAAAAUCATT | 357 | UGAUUUUCUUGCUCCUGCTT | 358 |
| si-TD223 | AGCAGGAGCAAGAAAAAUCTT | 359 | GAUUUUCUUGCUCCUGCUTT | 360 |
| si-TD222 | GAGCAGGAGCAAGAAAAAUTT | 361 | AUUUUCUUGCUCCUGCUCTT | 362 |

Fig. 1B

| | | | | |
|---|---|---|---|---|
| si-TD221 | AGAGCAGGAGCAAGAAAAATT | 363 | UUUUUCUUGCUCCUGCUCUTT | 364 |
| si-TD220 | AAGAGCAGGAGCAAGAAAATT | 365 | UUUUCUUGCUCCUGCUCUUTT | 366 |
| si-TD219 | CAAGAGCAGGAGCAAGAAATT | 367 | UUUCUUGCUCCUGCUCUUGTT | 368 |
| si-TD218 | CCAAGAGCAGGAGCAAGAATT | 369 | UUCUUGCUCCUGCUCUUGGTT | 370 |
| si-TD217 | UCCAAGAGCAGGAGCAAGATT | 371 | UCUUGCUCCUGCUCUUGGATT | 372 |
| si-TD385 | AGGACAGCUAUCUUGCCCATT | 373 | UGGGCAAGAUAGCUGUCCUTT | 374 |
| si-TD384 | GAGGACAGCUAUCUUGCCCTT | 375 | GGGCAAGAUAGCUGUCCUCTT | 376 |
| si-TD383 | GGAGGACAGCUAUCUUGCCTT | 377 | GGCAAGAUAGCUGUCCUCCTT | 378 |
| si-TD382 | AGGAGGACAGCUAUCUUGCTT | 379 | GCAAGAUAGCUGUCCUCCUTT | 380 |
| si-TD381 | GAGGAGGACAGCUAUCUUGTT | 381 | CAAGAUAGCUGUCCUCCUCTT | 382 |
| si-TD380 | UGAGGAGGACAGCUAUCUUTT | 383 | AAGAUAGCUGUCCUCCUCATT | 384 |
| si-TD379 | UUGAGGAGGACAGCUAUCUTT | 385 | AGAUAGCUGUCCUCCUCAATT | 386 |
| si-TD378 | GUUGAGGAGGACAGCUAUCTT | 387 | GAUAGCUGUCCUCCUCAACTT | 388 |
| si-TD377 | CGUUGAGGAGGACAGCUAUTT | 389 | AUAGCUGUCCUCCUCAACGTT | 390 |
| si-TD376 | CCGUUGAGGAGGACAGCUATT | 391 | UAGCUGUCCUCCUCAACGGTT | 392 |
| si-TD375 | ACCGUUGAGGAGGACAGCUTT | 393 | AGCUGUCCUCCUCAACGGUTT | 394 |
| si-TD374 | CACCGUUGAGGAGGACAGCTT | 395 | GCUGUCCUCCUCAACGGUGTT | 396 |
| si-TD373 | UCACCGUUGAGGAGGACAGTT | 397 | CUGUCCUCCUCAACGGUGATT | 398 |
| si-TD372 | GUCACCGUUGAGGAGGACATT | 399 | UGUCCUCCUCAACGGUGACTT | 400 |
| si-TD371 | GGUCACCGUUGAGGAGGACTT | 401 | GUCCUCCUCAACGGUGACCTT | 402 |
| si-TD370 | AGGUCACCGUUGAGGAGGATT | 403 | UCCUCCUCAACGGUGACCUTT | 404 |
| si-TD369 | GAGGUCACCGUUGAGGAGGTT | 405 | CCUCCUCAACGGUGACCUCTT | 406 |
| si-TD368 | UGAGGUCACCGUUGAGGAGTT | 407 | CUCCUCAACGGUGACCUCATT | 408 |
| si-TD367 | AUGAGGUCACCGUUGAGGATT | 409 | UCCUCAACGGUGACCUCAUTT | 410 |
| si-TD366 | GAUGAGGUCACCGUUGAGGTT | 411 | CCUCAACGGUGACCUCAUCTT | 412 |
| si-TD364 | UGGAUGAGGUCACCGUUGATT | 413 | UCAACGGUGACCUCAUCCATT | 414 |
| si-TD363 | UUGGAUGAGGUCACCGUUGTT | 415 | CAACGGUGACCUCAUCCAATT | 416 |
| si-TD362 | CUUGGAUGAGGUCACCGUUTT | 417 | AACGGUGACCUCAUCCAAGTT | 418 |
| si-TD361 | UCUUGGAUGAGGUCACCGUTT | 419 | ACGGUGACCUCAUCCAAGATT | 420 |
| si-TD360 | AUCUUGGAUGAGGUCACCGTT | 421 | CGGUGACCUCAUCCAAGAUTT | 422 |
| si-TD359 | UAUCUUGGAUGAGGUCACCTT | 423 | GGUGACCUCAUCCAAGAUATT | 424 |
| si-TD358 | GUAUCUUGGAUGAGGUCACTT | 425 | GUGACCUCAUCCAAGAUACTT | 426 |
| si-TD357 | CGUAUCUUGGAUGAGGUCATT | 427 | UGACCUCAUCCAAGAUACGTT | 428 |
| si-TD356 | CCGUAUCUUGGAUGAGGUCTT | 429 | GACCUCAUCCAAGAUACGGTT | 430 |
| si-TD355 | ACCGUAUCUUGGAUGAGGUTT | 431 | ACCUCAUCCAAGAUACGGUTT | 432 |
| si-TD354 | AACCGUAUCUUGGAUGAGGTT | 433 | CCUCAUCCAAGAUACGGUUTT | 434 |
| si-TD454 | AAGACCCUUCCCCUGAGGATT | 435 | UCCUCAGGGGAAGGGUCUUTT | 436 |
| si-TD453 | GAAGACCCUUCCCCUGAGGTT | 437 | CCUCAGGGGAAGGGUCUUCTT | 438 |
| si-TD452 | GGAAGACCCUUCCCCUGAGTT | 439 | CUCAGGGGAAGGGUCUUCCTT | 440 |
| si-TD451 | AGGAAGACCCUUCCCCUGATT | 441 | UCAGGGGAAGGGUCUUCCUTT | 442 |
| si-TD450 | GAGGAAGACCCUUCCCCUGTT | 443 | CAGGGGAAGGGUCUUCCUCTT | 444 |
| si-TD449 | AGAGGAAGACCCUUCCCCUTT | 445 | AGGGGAAGGGUCUUCCUCUTT | 446 |
| si-TD448 | AAGAGGAAGACCCUUCCCCTT | 447 | GGGGAAGGGUCUUCCUCUUTT | 448 |
| si-TD447 | CAAGAGGAAGACCCUUCCCTT | 449 | GGGAAGGGUCUUCCUCUUGTT | 450 |

Fig. 1C

| | | | | |
|---|---|---|---|---|
| si-TD446 | CCAAGAGGAAGACCCUUCCTT | 451 | GGAAGGGUCUUCCUCUUGGTT | 452 |
| si-TD445 | UCCAAGAGGAAGACCCUUCTT | 453 | GAAGGGUCUUCCUCUUGGATT | 454 |
| si-TD444 | AUCCAAGAGGAAGACCCUUTT | 455 | AAGGGUCUUCCUCUUGGAUTT | 456 |
| si-TD443 | GAUCCAAGAGGAAGACCCUTT | 457 | AGGGUCUUCCUCUUGGAUCTT | 458 |
| si-TD442 | UGAUCCAAGAGGAAGACCCTT | 459 | GGGUCUUCCUCUUGGAUCATT | 460 |
| si-TD509 | GGACAAGUCUGUGGCCCAGTT | 461 | CUGGGCCACAGACUUGUCCTT | 462 |
| si-TD508 | UGGACAAGUCUGUGGCCCATT | 463 | UGGGCCACAGACUUGUCCATT | 464 |
| si-TD507 | CUGGACAAGUCUGUGGCCCTT | 465 | GGGCCACAGACUUGUCCAGTT | 466 |
| si-TD577 | GCCUCCUGGAGGAGAUCCTT | 467 | GGAUCUCCUCCAGGGAGGCTT | 468 |
| si-TD578 | CCUCCCUGGAGGAGAUCCUTT | 469 | AGGAUCUCCUCCAGGGAGGTT | 470 |
| si-TD611 | GGUAGCAAGGAAACUGGAGTT | 471 | CUCCAGUUUCCUUGCUACCTT | 472 |
| si-TD610 | UGGUAGCAAGGAAACUGGATT | 473 | UCCAGUUUCCUUGCUACCATT | 474 |
| si-TD609 | CUGGUAGCAAGGAAACUGGTT | 475 | CCAGUUUCCUUGCUACCAGTT | 476 |
| si-TD608 | CCUGGUAGCAAGGAAACUGTT | 477 | CAGUUUCCUUGCUACCAGGTT | 478 |
| si-TD607 | ACCUGGUAGCAAGGAAACUTT | 479 | AGUUUCCUUGCUACCAGGUTT | 480 |
| si-TD606 | GACCUGGUAGCAAGGAAACTT | 481 | GUUUCCUUGCUACCAGGUCTT | 482 |
| si-TD604 | AGGACCUGGUAGCAAGGAATT | 483 | UUCCUUGCUACCAGGUCCUTT | 484 |
| si-TD603 | CAGGACCUGGUAGCAAGGATT | 485 | UCCUUGCUACCAGGUCCUGTT | 486 |
| si-TD602 | CCAGGACCUGGUAGCAAGGTT | 487 | CCUUGCUACCAGGUCCUGGTT | 488 |
| si-TD601 | UCCAGGACCUGGUAGCAAGTT | 489 | CUUGCUACCAGGUCCUGGATT | 490 |
| si-TD600 | AUCCAGGACCUGGUAGCAATT | 491 | UUGCUACCAGGUCCUGGAUTT | 492 |
| si-TD599 | GAUCCAGGACCUGGUAGCATT | 493 | UGCUACCAGGUCCUGGAUCTT | 494 |
| si-TD598 | GGAUCCAGGACCUGGUAGCTT | 495 | GCUACCAGGUCCUGGAUCCTT | 496 |
| si-TD597 | CGGAUCCAGGACCUGGUAGTT | 497 | CUACCAGGUCCUGGAUCCGTT | 498 |
| si-TD596 | CCGGAUCCAGGACCUGGUATT | 499 | UACCAGGUCCUGGAUCCGGTT | 500 |
| si-TD595 | CCCGGAUCCAGGACCUGGUTT | 501 | ACCAGGUCCUGGAUCCGGGTT | 502 |
| si-TD594 | UCCCGGAUCCAGGACCUGGTT | 503 | CCAGGUCCUGGAUCCGGGATT | 504 |
| si-TD593 | GUCCCGGAUCCAGGACCUGTT | 505 | CAGGUCCUGGAUCCGGGACTT | 506 |
| si-TD592 | UGUCCCGGAUCCAGGACCUTT | 507 | AGGUCCUGGAUCCGGGACATT | 508 |
| si-TD591 | CUGUCCCGGAUCCAGGACCTT | 509 | GGUCCUGGAUCCGGGACAGTT | 510 |
| si-TD590 | GCUGUCCCGGAUCCAGGACTT | 511 | GUCCUGGAUCCGGGACAGCTT | 512 |
| si-TD589 | AGCUGUCCCGGAUCCAGGATT | 513 | UCCUGGAUCCGGGACAGCUTT | 514 |
| si-TD588 | CAGCUGUCCCGGAUCCAGGTT | 515 | CCUGGAUCCGGGACAGCUGTT | 516 |
| si-TD587 | GCAGCUGUCCCGGAUCCAGTT | 517 | CUGGAUCCGGGACAGCUGCTT | 518 |
| si-TD586 | GGCAGCUGUCCCGGAUCCATT | 519 | UGGAUCCGGGACAGCUGCCTT | 520 |
| si-TD585 | GGGCAGCUGUCCCGGAUCCTT | 521 | GGAUCCGGGACAGCUGCCCTT | 522 |
| si-TD721 | AGCUGAGAGACCUGUACAGTT | 523 | CUGUACAGGUCUCUCAGCUTT | 524 |
| si-TD720 | GAGCUGAGAGACCUGUACATT | 525 | UGUACAGGUCUCUCAGCUCTT | 526 |
| si-TD719 | GGAGCUGAGAGACCUGUACTT | 527 | GUACAGGUCUCUCAGCUCCTT | 528 |
| si-TD718 | GGGAGCUGAGAGACCUGUATT | 529 | UACAGGUCUCUCAGCUCCCTT | 530 |
| si-TD742 | AGAUGGACCUGCAGACCCTT | 531 | GGGGUCUGCAGGUCCAUCUTT | 532 |
| si-TD741 | CAGAUGGACCUGCAGACCCTT | 533 | GGGUCUGCAGGUCCAUCUGTT | 534 |
| si-TD744 | ACUCCCACCUCAGACAGACTT | 535 | GUCUGUCUGAGGUGGGAGUTT | 536 |
| si-TD743 | GACUCCCACCUCAGACAGATT | 537 | UCUGUCUGAGGUGGGAGUCTT | 538 |

Fig. 1D

| | | | | |
|---|---|---|---|---|
| si-TD144 | GGUAAAGAUGAGAAAAAUTT | 539 | AUUUUUCUCAUCUUUUACCTT | 540 |
| si-TD145 | GUAAAGAUGAGAAAAAUATT | 541 | UAUUUUUCUCAUCUUUUACTT | 542 |
| si-TD479 | CUCUUGUGCUGAGAGCUUUTT | 543 | AAAGCUCUCAGCACAAGAGTT | 544 |
| si-TD480 | UCUUGUGCUGAGAGCUUUCTT | 545 | GAAAGCUCUCAGCACAAGATT | 546 |
| si-TD481 | CUUGUGCUGAGAGCUUUCGTT | 547 | CGAAAGCUCUCAGCACAAGTT | 548 |
| si-TD482 | UUGUGCUGAGAGCUUUCGGTT | 549 | CCGAAAGCUCUCAGCACAATT | 550 |
| si-TD483 | UGUGCUGAGAGCUUUCGGGTT | 551 | CCCGAAAGCUCUCAGCACATT | 552 |
| si-TD584 | GGGGCAGCUGUCCCGGAUCTT | 553 | GAUCCGGGACAGCUGCCCCTT | 554 |
| si-TD583 | CGGGGCAGCUGUCCCGGAUTT | 555 | AUCCGGGACAGCUGCCCCGTT | 556 |
| si-TD582 | CCGGGGCAGCUGUCCCGGATT | 557 | UCCGGGACAGCUGCCCCGGTT | 558 |
| si-TD740 | ACAGAUGGACCUGCAGACCTT | 559 | GGUCUGCAGGUCCAUCUGUTT | 560 |
| si-TD739 | GACAGAUGGACCUGCAGACTT | 561 | GUCUGCAGGUCCAUCUGUCTT | 562 |
| si-TD738 | AGACAGAUGGACCUGCAGATT | 563 | UCUGCAGGUCCAUCUGUCUTT | 564 |
| si-TD737 | CAGACAGAUGGACCUGCAGTT | 565 | CUGCAGGUCCAUCUGUCUGTT | 566 |
| si-TD736 | ACAGACAGAUGGACCUGCATT | 567 | UGCAGGUCCAUCUGUCUGUTT | 568 |
| si-TD735 | UACAGACAGAUGGACCUGCTT | 569 | GCAGGUCCAUCUGUCUGUATT | 570 |
| si-TD734 | GUACAGACAGAUGGACCUGTT | 571 | CAGGUCCAUCUGUCUGUACTT | 572 |
| si-TD733 | UGUACAGACAGAUGGACCUTT | 573 | AGGUCCAUCUGUCUGUACATT | 574 |
| si-TD732 | CUGUACAGACAGAUGGACCTT | 575 | GGUCCAUCUGUCUGUACAGTT | 576 |
| si-TD731 | CCUGUACAGACAGAUGGACTT | 577 | GUCCAUCUGUCUGUACAGGTT | 578 |
| si-TD730 | ACCUGUACAGACAGAUGGATT | 579 | UCCAUCUGUCUGUACAGGUTT | 580 |
| si-TD729 | GACCUGUACAGACAGAUGGTT | 581 | CCAUCUGUCUGUACAGGUCTT | 582 |
| si-TD728 | AGACCUGUACAGACAGAUGTT | 583 | CAUCUGUCUGUACAGGUCUTT | 584 |
| si-TD727 | GAGACCUGUACAGACAGAUTT | 585 | AUCUGUCUGUACAGGUCUCTT | 586 |
| si-TD726 | AGAGACCUGUACAGACAGATT | 587 | UCUGUCUGUACAGGUCUCUTT | 588 |
| si-TD725 | GAGAGACCUGUACAGACAGTT | 589 | CUGUCUGUACAGGUCUCUCTT | 590 |
| si-TD723 | CUGAGAGACCUGUACAGACTT | 591 | GUCUGUACAGGUCUCUCAGTT | 592 |
| si-TD722 | GCUGAGAGACCUGUACAGATT | 593 | UCUGUACAGGUCUCUCAGCTT | 594 |
| si-TD717 | AGGGAGCUGAGAGACCUGUTT | 595 | ACAGGUCUCUCAGCUCCCUTT | 596 |
| si-TD716 | CAGGGAGCUGAGAGACCUGTT | 597 | CAGGUCUCUCAGCUCCCUGTT | 598 |
| si-TD715 | UCAGGGAGCUGAGAGACCUTT | 599 | AGGUCUCUCAGCUCCCUGATT | 600 |
| si-TD714 | GUCAGGGAGCUGAGAGACCTT | 601 | GGUCUCUCAGCUCCCUGACTT | 602 |
| si-7 | UGGGAGAUGGGAAGCGAAATT | 603 | UUUCGCUUCCCAUCUCCCATT | 604 |
| si-10 | CAGACAAAGGGGCCACCUATT | 605 | UAGGUGGCCCCUUUGUCUGTT | 606 |
| si-1 | GGACCUGGUAGCAAGGAAATT | 607 | UUUCCUUGCUACCAGGUCCTT | 608 |
| NC-1 | GAAAGAUAGAGAAGGUAGATT | 609 | UCUACCUUCUCUAUCUUUCTT | 610 |
| NC-2 | GCAACAGCCGAUGAAGUUATT | 611 | UAACUUCAUCGGCUGUUGCTT | 612 |
| NC-3 | GGCCGAGCAACGAAUGUCATT | 613 | UGACAUUCGUUGCUCGGCCTT | 614 |
| NC-4 | GGACAUCGAACGAAGUGCUTT | 615 | AGCACUUCGUUCGAUGUCCTT | 616 |
| NC-5 | GCGGUCCUGCGACGUACATT | 617 | UGUACGUCGCAGGGACCGCTT | 618 |
| NC-6 | GCUGCGCGAACCCAUCAAATT | 619 | UUUGAUGGGUUCGCGCAGCTT | 620 |
| NC-7 | UUCUCCGAACGUGUCACGUTT | 621 | ACGUGACACGUUCGGAGAATT | 622 |
| NC-8 | GCGACGAUCUGCCUAAGAUTT | 623 | AUCUUAGGCAGAUCGUCGCTT | 624 |

Fig. 1E

SEQUENCE LISTING

<160> NUMBER OF SEQ ID NOS: 625

<210> SEQ ID NO 1
<211> LENGTH: 19
<212> TYPE: RNA
<213> ORGANISM: Artificial Sequence

```
<220> FEATURE:
<223> OTHER INFORMATION: si-TD037 sense

<400> SEQUENCE: 1
aaggucggcu ggguccgga                                                      19

<210> SEQ ID NO 2
<211> LENGTH: 19
<212> TYPE: RNA
<213> ORGANISM: Artificial Sequence
<220> FEATURE:
<223> OTHER INFORMATION: si-TD037 antisense

<400> SEQUENCE: 2
uccggaccca gccgaccuu                                                      19

<210> SEQ ID NO 3
<211> LENGTH: 19
<212> TYPE: RNA
<213> ORGANISM: Artificial Sequence
<220> FEATURE:
<223> OTHER INFORMATION: si-TD040 sense

<400> SEQUENCE: 3
gucggcuggg uccggaaau                                                      19

<210> SEQ ID NO 4
<211> LENGTH: 19
<212> TYPE: RNA
<213> ORGANISM: Artificial Sequence
<220> FEATURE:
<223> OTHER INFORMATION: si-TD040 antisense

<400> SEQUENCE: 4
auuuccggac ccagccgac                                                      19

<210> SEQ ID NO 5
<211> LENGTH: 19
<212> TYPE: RNA
<213> ORGANISM: Artificial Sequence
<220> FEATURE:
<223> OTHER INFORMATION: si-TD042 sense

<400> SEQUENCE: 5
cggcuggguc cggaaauuc                                                      19

<210> SEQ ID NO 6
<211> LENGTH: 19
<212> TYPE: RNA
<213> ORGANISM: Artificial Sequence
<220> FEATURE:
<223> OTHER INFORMATION: si-TD042 antisense

<400> SEQUENCE: 6
gaauuuccgg acccagccg                                                      19

<210> SEQ ID NO 7
<211> LENGTH: 19
<212> TYPE: RNA
<213> ORGANISM: Artificial Sequence
<220> FEATURE:
<223> OTHER INFORMATION: si-TD044 sense

<400> SEQUENCE: 7
gcuggguccg gaaauucug                                                      19
```

```
<210> SEQ ID NO 8
<211> LENGTH: 19
<212> TYPE: RNA
<213> ORGANISM: Artificial Sequence
<220> FEATURE:
<223> OTHER INFORMATION: si-TD044 antisense

<400> SEQUENCE: 8
cagaauuucc ggacccagc                                              19

<210> SEQ ID NO 9
<211> LENGTH: 19
<212> TYPE: RNA
<213> ORGANISM: Artificial Sequence
<220> FEATURE:
<223> OTHER INFORMATION: si-TD050 sense

<400> SEQUENCE: 9
uccggaaauu cugcgggaa                                              19

<210> SEQ ID NO 10
<211> LENGTH: 19
<212> TYPE: RNA
<213> ORGANISM: Artificial Sequence
<220> FEATURE:
<223> OTHER INFORMATION: si-TD050 antisense

<400> SEQUENCE: 10
uucccgcaga auuccgga                                               19

<210> SEQ ID NO 11
<211> LENGTH: 19
<212> TYPE: RNA
<213> ORGANISM: Artificial Sequence
<220> FEATURE:
<223> OTHER INFORMATION: si-TD057 sense

<400> SEQUENCE: 11
auucugcggg aaagggauu                                              19

<210> SEQ ID NO 12
<211> LENGTH: 19
<212> TYPE: RNA
<213> ORGANISM: Artificial Sequence
<220> FEATURE:
<223> OTHER INFORMATION: si-TD057 antisense

<400> SEQUENCE: 12
aaucccuuuc ccgcagaau                                              19

<210> SEQ ID NO 13
<211> LENGTH: 19
<212> TYPE: RNA
<213> ORGANISM: Artificial Sequence
<220> FEATURE:
<223> OTHER INFORMATION: si-TD058 sense

<400> SEQUENCE: 13
uucugcggga aagggauuu                                              19

<210> SEQ ID NO 14
<211> LENGTH: 19
<212> TYPE: RNA
<213> ORGANISM: Artificial Sequence
<220> FEATURE:
<223> OTHER INFORMATION: si-TD058 antisense
```

```
<400> SEQUENCE: 14
aaaucccuuu cccgcagaa                                               19

<210> SEQ ID NO 15
<211> LENGTH: 19
<212> TYPE: RNA
<213> ORGANISM: Artificial Sequence
<220> FEATURE:
<223> OTHER INFORMATION: si-TD060 sense

<400> SEQUENCE: 15
cugcgggaaa gggauuuuc                                               19

<210> SEQ ID NO 16
<211> LENGTH: 19
<212> TYPE: RNA
<213> ORGANISM: Artificial Sequence
<220> FEATURE:
<223> OTHER INFORMATION: si-TD060 antisense

<400> SEQUENCE: 16
gaaaaucccu uucccgcag                                               19

<210> SEQ ID NO 17
<211> LENGTH: 19
<212> TYPE: RNA
<213> ORGANISM: Artificial Sequence
<220> FEATURE:
<223> OTHER INFORMATION: si-TD061 sense

<400> SEQUENCE: 17
ugcgggaaag ggauuuuca                                               19

<210> SEQ ID NO 18
<211> LENGTH: 19
<212> TYPE: RNA
<213> ORGANISM: Artificial Sequence
<220> FEATURE:
<223> OTHER INFORMATION: si-TD061 antisense

<400> SEQUENCE: 18
ugaaaauccc uucccgca                                                19

<210> SEQ ID NO 19
<211> LENGTH: 19
<212> TYPE: RNA
<213> ORGANISM: Artificial Sequence
<220> FEATURE:
<223> OTHER INFORMATION: si-TD062 sense

<400> SEQUENCE: 19
gcgggaaagg gauuuucag                                               19

<210> SEQ ID NO 20
<211> LENGTH: 19
<212> TYPE: RNA
<213> ORGANISM: Artificial Sequence
<220> FEATURE:
<223> OTHER INFORMATION: si-TD062 antisense

<400> SEQUENCE: 20
cugaaaaucc cuucccgc                                                19
```

```
<210> SEQ ID NO 21
<211> LENGTH: 19
<212> TYPE: RNA
<213> ORGANISM: Artificial Sequence
<220> FEATURE:
<223> OTHER INFORMATION: si-TD064 sense

<400> SEQUENCE: 21
gggaaaggga uuucaggg                                          19

<210> SEQ ID NO 22
<211> LENGTH: 19
<212> TYPE: RNA
<213> ORGANISM: Artificial Sequence
<220> FEATURE:
<223> OTHER INFORMATION: si-TD064 antisense

<400> SEQUENCE: 22
cccugaaaau cccuuuccc                                         19

<210> SEQ ID NO 23
<211> LENGTH: 19
<212> TYPE: RNA
<213> ORGANISM: Artificial Sequence
<220> FEATURE:
<223> OTHER INFORMATION: si-TD065 sense

<400> SEQUENCE: 23
ggaaagggau uuucaggga                                         19

<210> SEQ ID NO 24
<211> LENGTH: 19
<212> TYPE: RNA
<213> ORGANISM: Artificial Sequence
<220> FEATURE:
<223> OTHER INFORMATION: si-TD065 antisense

<400> SEQUENCE: 24
ucccugaaaa ucccuuucc                                         19

<210> SEQ ID NO 25
<211> LENGTH: 19
<212> TYPE: RNA
<213> ORGANISM: Artificial Sequence
<220> FEATURE:
<223> OTHER INFORMATION: si-TD066 sense

<400> SEQUENCE: 25
gaaagggauu uucagggag                                         19

<210> SEQ ID NO 26
<211> LENGTH: 19
<212> TYPE: RNA
<213> ORGANISM: Artificial Sequence
<220> FEATURE:
<223> OTHER INFORMATION: si-TD066 antisense

<400> SEQUENCE: 26
cucccugaaa aucccuuuc                                         19

<210> SEQ ID NO 27
<211> LENGTH: 19
<212> TYPE: RNA
<213> ORGANISM: Artificial Sequence
<220> FEATURE:
<223> OTHER INFORMATION: si-TD067 sense
```

```
<400> SEQUENCE: 27
aaagggauuu ucagggaga                                                19

<210> SEQ ID NO 28
<211> LENGTH: 19
<212> TYPE: RNA
<213> ORGANISM: Artificial Sequence
<220> FEATURE:
<223> OTHER INFORMATION: si-TD067 antisense

<400> SEQUENCE: 28
ucucccugaa aaucccuuu                                                19

<210> SEQ ID NO 29
<211> LENGTH: 19
<212> TYPE: RNA
<213> ORGANISM: Artificial Sequence
<220> FEATURE:
<223> OTHER INFORMATION: si-TD068 sense

<400> SEQUENCE: 29
aagggauuuu cagggagau                                                19

<210> SEQ ID NO 30
<211> LENGTH: 19
<212> TYPE: RNA
<213> ORGANISM: Artificial Sequence
<220> FEATURE:
<223> OTHER INFORMATION: si-TD068 antisense

<400> SEQUENCE: 30
aucucccuga aaaucccuu                                                19

<210> SEQ ID NO 31
<211> LENGTH: 19
<212> TYPE: RNA
<213> ORGANISM: Artificial Sequence
<220> FEATURE:
<223> OTHER INFORMATION: si-TD070 sense

<400> SEQUENCE: 31
gggauuuuca gggagauuu                                                19

<210> SEQ ID NO 32
<211> LENGTH: 19
<212> TYPE: RNA
<213> ORGANISM: Artificial Sequence
<220> FEATURE:
<223> OTHER INFORMATION: si-TD070 antisense

<400> SEQUENCE: 32
aaaucucccu gaaaauccc                                                19

<210> SEQ ID NO 33
<211> LENGTH: 19
<212> TYPE: RNA
<213> ORGANISM: Artificial Sequence
<220> FEATURE:
<223> OTHER INFORMATION: si-TD072 sense

<400> SEQUENCE: 33
gauuuucagg gagauuugg                                                19
```

```
<210> SEQ ID NO 34
<211> LENGTH: 19
<212> TYPE: RNA
<213> ORGANISM: Artificial Sequence
<220> FEATURE:
<223> OTHER INFORMATION: si-TD072 antisense

<400> SEQUENCE: 34
ccaaaucucc cugaaaauc                                                19

<210> SEQ ID NO 35
<211> LENGTH: 19
<212> TYPE: RNA
<213> ORGANISM: Artificial Sequence
<220> FEATURE:
<223> OTHER INFORMATION: si-TD074 sense

<400> SEQUENCE: 35
uuuucaggga gauuuggaa                                                19

<210> SEQ ID NO 36
<211> LENGTH: 19
<212> TYPE: RNA
<213> ORGANISM: Artificial Sequence
<220> FEATURE:
<223> OTHER INFORMATION: si-TD074 antisense

<400> SEQUENCE: 36
uuccaaaucu cccugaaaa                                                19

<210> SEQ ID NO 37
<211> LENGTH: 19
<212> TYPE: RNA
<213> ORGANISM: Artificial Sequence
<220> FEATURE:
<223> OTHER INFORMATION: si-TD076 sense

<400> SEQUENCE: 37
uucagggaga uuuggaaaa                                                19

<210> SEQ ID NO 38
<211> LENGTH: 19
<212> TYPE: RNA
<213> ORGANISM: Artificial Sequence
<220> FEATURE:
<223> OTHER INFORMATION: si-TD076 antisense

<400> SEQUENCE: 38
uuuuccaaau cucccugaa                                                19

<210> SEQ ID NO 39
<211> LENGTH: 19
<212> TYPE: RNA
<213> ORGANISM: Artificial Sequence
<220> FEATURE:
<223> OTHER INFORMATION: si-TD078 sense

<400> SEQUENCE: 39
cagggagauu uggaaaaac                                                19

<210> SEQ ID NO 40
<211> LENGTH: 19
<212> TYPE: RNA
<213> ORGANISM: Artificial Sequence
<220> FEATURE:
<223> OTHER INFORMATION: si-TD078 antisense
```

```
<400> SEQUENCE: 40
guuuuuccaa aucucccug                                                19

<210> SEQ ID NO 41
<211> LENGTH: 19
<212> TYPE: RNA
<213> ORGANISM: Artificial Sequence
<220> FEATURE:
<223> OTHER INFORMATION: si-TD080 sense

<400> SEQUENCE: 41
gggagauuug gaaaaaccg                                                19

<210> SEQ ID NO 42
<211> LENGTH: 19
<212> TYPE: RNA
<213> ORGANISM: Artificial Sequence
<220> FEATURE:
<223> OTHER INFORMATION: si-TD080 antisense

<400> SEQUENCE: 42
cgguuuuucc aaaucuccc                                                19

<210> SEQ ID NO 43
<211> LENGTH: 19
<212> TYPE: RNA
<213> ORGANISM: Artificial Sequence
<220> FEATURE:
<223> OTHER INFORMATION: si-TD082 sense

<400> SEQUENCE: 43
gagauuugga aaaccgcu                                                 19

<210> SEQ ID NO 44
<211> LENGTH: 19
<212> TYPE: RNA
<213> ORGANISM: Artificial Sequence
<220> FEATURE:
<223> OTHER INFORMATION: si-TD082 antisense

<400> SEQUENCE: 44
agcgguuuuu ccaaaucuc                                                19

<210> SEQ ID NO 45
<211> LENGTH: 19
<212> TYPE: RNA
<213> ORGANISM: Artificial Sequence
<220> FEATURE:
<223> OTHER INFORMATION: si-TD084 sense

<400> SEQUENCE: 45
gauuuggaaa aaccgcuau                                                19

<210> SEQ ID NO 46
<211> LENGTH: 19
<212> TYPE: RNA
<213> ORGANISM: Artificial Sequence
<220> FEATURE:
<223> OTHER INFORMATION: si-TD084 antisense

<400> SEQUENCE: 46
auagcgguuu uuccaaauc                                                19
```

```
<210> SEQ ID NO 47
<211> LENGTH: 19
<212> TYPE: RNA
<213> ORGANISM: Artificial Sequence
<220> FEATURE:
<223> OTHER INFORMATION: si-TD087 sense

<400> SEQUENCE: 47
uuggaaaaac cgcuaugug                                              19

<210> SEQ ID NO 48
<211> LENGTH: 19
<212> TYPE: RNA
<213> ORGANISM: Artificial Sequence
<220> FEATURE:
<223> OTHER INFORMATION: si-TD087 antisense

<400> SEQUENCE: 48
cacauagcgg uuuuuccaa                                              19

<210> SEQ ID NO 49
<211> LENGTH: 19
<212> TYPE: RNA
<213> ORGANISM: Artificial Sequence
<220> FEATURE:
<223> OTHER INFORMATION: si-TD089 sense

<400> SEQUENCE: 49
ggaaaaaccg cuaugggu                                               19

<210> SEQ ID NO 50
<211> LENGTH: 19
<212> TYPE: RNA
<213> ORGANISM: Artificial Sequence
<220> FEATURE:
<223> OTHER INFORMATION: si-TD089 antisense

<400> SEQUENCE: 50
accacauagc gguuuuucc                                              19

<210> SEQ ID NO 51
<211> LENGTH: 19
<212> TYPE: RNA
<213> ORGANISM: Artificial Sequence
<220> FEATURE:
<223> OTHER INFORMATION: si-TD093 sense

<400> SEQUENCE: 51
aaaccgcuau guggugcug                                              19

<210> SEQ ID NO 52
<211> LENGTH: 19
<212> TYPE: RNA
<213> ORGANISM: Artificial Sequence
<220> FEATURE:
<223> OTHER INFORMATION: si-TD093 antisense

<400> SEQUENCE: 52
cagcaccaca uagcgguuu                                              19

<210> SEQ ID NO 53
<211> LENGTH: 19
<212> TYPE: RNA
<213> ORGANISM: Artificial Sequence
<220> FEATURE:
<223> OTHER INFORMATION: si-TD094 sense
```

```
<400> SEQUENCE: 53
aaccgcuaug uggugcuga                                                19

<210> SEQ ID NO 54
<211> LENGTH: 19
<212> TYPE: RNA
<213> ORGANISM: Artificial Sequence
<220> FEATURE:
<223> OTHER INFORMATION: si-TD094 antisense

<400> SEQUENCE: 54
ucagcaccac auagcgguu                                                19

<210> SEQ ID NO 55
<211> LENGTH: 19
<212> TYPE: RNA
<213> ORGANISM: Artificial Sequence
<220> FEATURE:
<223> OTHER INFORMATION: si-TD096 sense

<400> SEQUENCE: 55
ccgcuaugug gugcugaaa                                                19

<210> SEQ ID NO 56
<211> LENGTH: 19
<212> TYPE: RNA
<213> ORGANISM: Artificial Sequence
<220> FEATURE:
<223> OTHER INFORMATION: si-TD096 antisense

<400> SEQUENCE: 56
uuucagcacc acauagcgg                                                19

<210> SEQ ID NO 57
<211> LENGTH: 19
<212> TYPE: RNA
<213> ORGANISM: Artificial Sequence
<220> FEATURE:
<223> OTHER INFORMATION: si-TD097 sense

<400> SEQUENCE: 57
cgcuaugugg ugcugaaag                                                19

<210> SEQ ID NO 58
<211> LENGTH: 19
<212> TYPE: RNA
<213> ORGANISM: Artificial Sequence
<220> FEATURE:
<223> OTHER INFORMATION: si-TD097 antisense

<400> SEQUENCE: 58
cuuucagcac cacauagcg                                                19

<210> SEQ ID NO 59
<211> LENGTH: 19
<212> TYPE: RNA
<213> ORGANISM: Artificial Sequence
<220> FEATURE:
<223> OTHER INFORMATION: si-TD098 sense

<400> SEQUENCE: 59
gcuauguggu gcugaaagg                                                19
```

```
<210> SEQ ID NO 60
<211> LENGTH: 19
<212> TYPE: RNA
<213> ORGANISM: Artificial Sequence
<220> FEATURE:
<223> OTHER INFORMATION: si-TD098 antisense

<400> SEQUENCE: 60
ccuuucagca ccacauagc                                                  19

<210> SEQ ID NO 61
<211> LENGTH: 19
<212> TYPE: RNA
<213> ORGANISM: Artificial Sequence
<220> FEATURE:
<223> OTHER INFORMATION: si-TD136 sense

<400> SEQUENCE: 61
gagaaggagg uaaaagaug                                                  19

<210> SEQ ID NO 62
<211> LENGTH: 19
<212> TYPE: RNA
<213> ORGANISM: Artificial Sequence
<220> FEATURE:
<223> OTHER INFORMATION: si-TD136 antisense

<400> SEQUENCE: 62
caucuuuuac cuccuucuc                                                  19

<210> SEQ ID NO 63
<211> LENGTH: 19
<212> TYPE: RNA
<213> ORGANISM: Artificial Sequence
<220> FEATURE:
<223> OTHER INFORMATION: si-TD137 sense

<400> SEQUENCE: 63
agaaggaggu aaaagauga                                                  19

<210> SEQ ID NO 64
<211> LENGTH: 19
<212> TYPE: RNA
<213> ORGANISM: Artificial Sequence
<220> FEATURE:
<223> OTHER INFORMATION: si-TD137 antisense

<400> SEQUENCE: 64
ucaucuuuua ccuccuucu                                                  19

<210> SEQ ID NO 65
<211> LENGTH: 19
<212> TYPE: RNA
<213> ORGANISM: Artificial Sequence
<220> FEATURE:
<223> OTHER INFORMATION: si-TD138 sense

<400> SEQUENCE: 65
gaaggaggua aaagaugag                                                  19

<210> SEQ ID NO 66
<211> LENGTH: 19
<212> TYPE: RNA
<213> ORGANISM: Artificial Sequence
<220> FEATURE:
<223> OTHER INFORMATION: si-TD138 antisense
```

```
<400> SEQUENCE: 66
cucaucuuuu accuccuuc                                              19

<210> SEQ ID NO 67
<211> LENGTH: 19
<212> TYPE: RNA
<213> ORGANISM: Artificial Sequence
<220> FEATURE:
<223> OTHER INFORMATION: si-TD139 sense

<400> SEQUENCE: 67
aaggagguaa aagaugaga                                              19

<210> SEQ ID NO 68
<211> LENGTH: 19
<212> TYPE: RNA
<213> ORGANISM: Artificial Sequence
<220> FEATURE:
<223> OTHER INFORMATION: si-TD139 antisense

<400> SEQUENCE: 68
ucucaucuuu uaccuccuu                                              19

<210> SEQ ID NO 69
<211> LENGTH: 19
<212> TYPE: RNA
<213> ORGANISM: Artificial Sequence
<220> FEATURE:
<223> OTHER INFORMATION: si-TD140 sense

<400> SEQUENCE: 69
aggagguaaa agaugagaa                                              19

<210> SEQ ID NO 70
<211> LENGTH: 19
<212> TYPE: RNA
<213> ORGANISM: Artificial Sequence
<220> FEATURE:
<223> OTHER INFORMATION: si-TD140 antisense

<400> SEQUENCE: 70
uucucaucuu uuaccuccu                                              19

<210> SEQ ID NO 71
<211> LENGTH: 19
<212> TYPE: RNA
<213> ORGANISM: Artificial Sequence
<220> FEATURE:
<223> OTHER INFORMATION: si-TD141 sense

<400> SEQUENCE: 71
ggagguaaaa gaugagaaa                                              19

<210> SEQ ID NO 72
<211> LENGTH: 19
<212> TYPE: RNA
<213> ORGANISM: Artificial Sequence
<220> FEATURE:
<223> OTHER INFORMATION: si-TD141 antisense

<400> SEQUENCE: 72
uuucucaucu uuuaccucc                                              19
```

```
<210> SEQ ID NO 73
<211> LENGTH: 19
<212> TYPE: RNA
<213> ORGANISM: Artificial Sequence
<220> FEATURE:
<223> OTHER INFORMATION: si-TD143 sense

<400> SEQUENCE: 73
agguaaaaga ugagaaaaa                                              19

<210> SEQ ID NO 74
<211> LENGTH: 19
<212> TYPE: RNA
<213> ORGANISM: Artificial Sequence
<220> FEATURE:
<223> OTHER INFORMATION: si-TD143 antisense

<400> SEQUENCE: 74
uuuuucucau cuuuuaccu                                              19

<210> SEQ ID NO 75
<211> LENGTH: 19
<212> TYPE: RNA
<213> ORGANISM: Artificial Sequence
<220> FEATURE:
<223> OTHER INFORMATION: si-TD181 sense

<400> SEQUENCE: 75
cugagugacu augagaagu                                              19

<210> SEQ ID NO 76
<211> LENGTH: 19
<212> TYPE: RNA
<213> ORGANISM: Artificial Sequence
<220> FEATURE:
<223> OTHER INFORMATION: si-TD181 antisense

<400> SEQUENCE: 76
acuucucaua gucacucag                                              19

<210> SEQ ID NO 77
<211> LENGTH: 19
<212> TYPE: RNA
<213> ORGANISM: Artificial Sequence
<220> FEATURE:
<223> OTHER INFORMATION: si-TD179 sense

<400> SEQUENCE: 77
accugaguga cuaugagaa                                              19

<210> SEQ ID NO 78
<211> LENGTH: 19
<212> TYPE: RNA
<213> ORGANISM: Artificial Sequence
<220> FEATURE:
<223> OTHER INFORMATION: si-TD179 antisense

<400> SEQUENCE: 78
uucucauagu cacucaggu                                              19

<210> SEQ ID NO 79
<211> LENGTH: 19
<212> TYPE: RNA
<213> ORGANISM: Artificial Sequence
<220> FEATURE:
<223> OTHER INFORMATION: si-TD178 sense
```

```
<400> SEQUENCE: 79
gaccugagug acuaugaga                                              19

<210> SEQ ID NO 80
<211> LENGTH: 19
<212> TYPE: RNA
<213> ORGANISM: Artificial Sequence
<220> FEATURE:
<223> OTHER INFORMATION: si-TD178 antisense

<400> SEQUENCE: 80
ucucauaguc acucagguc                                              19

<210> SEQ ID NO 81
<211> LENGTH: 19
<212> TYPE: RNA
<213> ORGANISM: Artificial Sequence
<220> FEATURE:
<223> OTHER INFORMATION: si-TD177 sense

<400> SEQUENCE: 81
ugaccugagu gacuaugag                                              19

<210> SEQ ID NO 82
<211> LENGTH: 19
<212> TYPE: RNA
<213> ORGANISM: Artificial Sequence
<220> FEATURE:
<223> OTHER INFORMATION: si-TD177 antisense

<400> SEQUENCE: 82
cucauaguca cucagguca                                              19

<210> SEQ ID NO 83
<211> LENGTH: 19
<212> TYPE: RNA
<213> ORGANISM: Artificial Sequence
<220> FEATURE:
<223> OTHER INFORMATION: si-TD176 sense

<400> SEQUENCE: 83
uugaccugag ugacuauga                                              19

<210> SEQ ID NO 84
<211> LENGTH: 19
<212> TYPE: RNA
<213> ORGANISM: Artificial Sequence
<220> FEATURE:
<223> OTHER INFORMATION: si-TD176 antisense

<400> SEQUENCE: 84
ucauagucac ucaggucaa                                              19

<210> SEQ ID NO 85
<211> LENGTH: 19
<212> TYPE: RNA
<213> ORGANISM: Artificial Sequence
<220> FEATURE:
<223> OTHER INFORMATION: si-TD224 sense

<400> SEQUENCE: 85
gcaggagcaa gaaaaauca                                              19
```

-continued

```
<210> SEQ ID NO 86
<211> LENGTH: 19
<212> TYPE: RNA
<213> ORGANISM: Artificial Sequence
<220> FEATURE:
<223> OTHER INFORMATION: si-TD224 antisense

<400> SEQUENCE: 86 ugauuuucu ugcuccugc                                                   19

<210> SEQ ID NO 87
<211> LENGTH: 19
<212> TYPE: RNA
<213> ORGANISM: Artificial Sequence
<220> FEATURE:
<223> OTHER INFORMATION: si-TD221 sense

<400> SEQUENCE: 87
agagcaggag caagaaaaa                                                  19

<210> SEQ ID NO 88
<211> LENGTH: 19
<212> TYPE: RNA
<213> ORGANISM: Artificial Sequence
<220> FEATURE:
<223> OTHER INFORMATION: si-TD221 antisense

<400> SEQUENCE: 88
uuuuucuugc uccugcucu                                                  19

<210> SEQ ID NO 89
<211> LENGTH: 19
<212> TYPE: RNA
<213> ORGANISM: Artificial Sequence
<220> FEATURE:
<223> OTHER INFORMATION: si-TD217 sense

<400> SEQUENCE: 89
uccaagagca ggagcaaga                                                  19

<210> SEQ ID NO 90
<211> LENGTH: 19
<212> TYPE: RNA
<213> ORGANISM: Artificial Sequence
<220> FEATURE:
<223> OTHER INFORMATION: si-TD217 antisense

<400> SEQUENCE: 90
ucuugcuccu gcucuugga                                                  19

<210> SEQ ID NO 91
<211> LENGTH: 19
<212> TYPE: RNA
<213> ORGANISM: Artificial Sequence
<220> FEATURE:
<223> OTHER INFORMATION: si-TD380 sense

<400> SEQUENCE: 91
ugaggaggac agcuaucuu                                                  19

<210> SEQ ID NO 92
<211> LENGTH: 19
<212> TYPE: RNA
<213> ORGANISM: Artificial Sequence
<220> FEATURE:
<223> OTHER INFORMATION: si-TD380 antisense
```

<400> SEQUENCE: 92
aagauagcug uccuccuca                                    19

<210> SEQ ID NO 93
<211> LENGTH: 19
<212> TYPE: RNA
<213> ORGANISM: Artificial Sequence
<220> FEATURE:
<223> OTHER INFORMATION: si-TD378 sense

<400> SEQUENCE: 93
guugaggagg acagcuauc                                    19

<210> SEQ ID NO 94
<211> LENGTH: 19
<212> TYPE: RNA
<213> ORGANISM: Artificial Sequence
<220> FEATURE:
<223> OTHER INFORMATION: si-TD378 antisense

<400> SEQUENCE: 94
gauagcuguc cuccucaac                                    19

<210> SEQ ID NO 95
<211> LENGTH: 19
<212> TYPE: RNA
<213> ORGANISM: Artificial Sequence
<220> FEATURE:
<223> OTHER INFORMATION: si-TD376 sense

<400> SEQUENCE: 95
ccguugagga ggacagcua                                    19

<210> SEQ ID NO 96
<211> LENGTH: 19
<212> TYPE: RNA
<213> ORGANISM: Artificial Sequence
<220> FEATURE:
<223> OTHER INFORMATION: si-TD376 antisense

<400> SEQUENCE: 96
uagcuguccu ccucaacgg                                    19

<210> SEQ ID NO 97
<211> LENGTH: 19
<212> TYPE: RNA
<213> ORGANISM: Artificial Sequence
<220> FEATURE:
<223> OTHER INFORMATION: si-TD372 sense

<400> SEQUENCE: 97
gucaccguug aggaggaca                                    19

<210> SEQ ID NO 98
<211> LENGTH: 19
<212> TYPE: RNA
<213> ORGANISM: Artificial Sequence
<220> FEATURE:
<223> OTHER INFORMATION: si-TD372 antisense

<400> SEQUENCE: 98
uguccuccuc aacggugac                                    19

```
<210> SEQ ID NO 99
<211> LENGTH: 19
<212> TYPE: RNA
<213> ORGANISM: Artificial Sequence
<220> FEATURE:
<223> OTHER INFORMATION: si-TD370 sense

<400> SEQUENCE: 99
aggucaccgu ugaggagga                                                      19

<210> SEQ ID NO 100
<211> LENGTH: 19
<212> TYPE: RNA
<213> ORGANISM: Artificial Sequence
<220> FEATURE:
<223> OTHER INFORMATION: si-TD370 antisense

<400> SEQUENCE: 100
uccuccucaa cggugaccu                                                      19

<210> SEQ ID NO 101
<211> LENGTH: 19
<212> TYPE: RNA
<213> ORGANISM: Artificial Sequence
<220> FEATURE:
<223> OTHER INFORMATION: si-TD364 sense

<400> SEQUENCE: 101
uggaugaggu caccguuga                                                      19

<210> SEQ ID NO 102
<211> LENGTH: 19
<212> TYPE: RNA
<213> ORGANISM: Artificial Sequence
<220> FEATURE:
<223> OTHER INFORMATION: si-TD364 antisense

<400> SEQUENCE: 102
ucaacgguga ccucaucca                                                      19

<210> SEQ ID NO 103
<211> LENGTH: 19
<212> TYPE: RNA
<213> ORGANISM: Artificial Sequence
<220> FEATURE:
<223> OTHER INFORMATION: si-TD362 sense

<400> SEQUENCE: 103
cuuggaugag gucaccguu                                                      19

<210> SEQ ID NO 104
<211> LENGTH: 19
<212> TYPE: RNA
<213> ORGANISM: Artificial Sequence
<220> FEATURE:
<223> OTHER INFORMATION: si-TD362 antisense

<400> SEQUENCE: 104
aacggugacc ucauccaag                                                      19

<210> SEQ ID NO 105
<211> LENGTH: 19
<212> TYPE: RNA
<213> ORGANISM: Artificial Sequence
<220> FEATURE:
<223> OTHER INFORMATION: si-TD358 sense
```

```
<400> SEQUENCE: 105
guaucuugga ugaggucac                                              19

<210> SEQ ID NO 106
<211> LENGTH: 19
<212> TYPE: RNA
<213> ORGANISM: Artificial Sequence
<220> FEATURE:
<223> OTHER INFORMATION: si-TD358 antisense

<400> SEQUENCE: 106
gugaccucau ccaagauac                                              19

<210> SEQ ID NO 107
<211> LENGTH: 19
<212> TYPE: RNA
<213> ORGANISM: Artificial Sequence
<220> FEATURE:
<223> OTHER INFORMATION: si-TD451 sense

<400> SEQUENCE: 107
aggaagaccc uuccccuga                                              19

<210> SEQ ID NO 108
<211> LENGTH: 19
<212> TYPE: RNA
<213> ORGANISM: Artificial Sequence
<220> FEATURE:
<223> OTHER INFORMATION: si-TD451 antisense

<400> SEQUENCE: 108
ucaggggaag ggucuuccu                                              19

<210> SEQ ID NO 109
<211> LENGTH: 19
<212> TYPE: RNA
<213> ORGANISM: Artificial Sequence
<220> FEATURE:
<223> OTHER INFORMATION: si-TD443 sense

<400> SEQUENCE: 109
gauccaagag gaagacccu                                              19

<210> SEQ ID NO 110
<211> LENGTH: 19
<212> TYPE: RNA
<213> ORGANISM: Artificial Sequence
<220> FEATURE:
<223> OTHER INFORMATION: si-TD443 antisense

<400> SEQUENCE: 110
agggucuucc ucuuggauc                                              19

<210> SEQ ID NO 111
<211> LENGTH: 19
<212> TYPE: RNA
<213> ORGANISM: Artificial Sequence
<220> FEATURE:
<223> OTHER INFORMATION: si-TD509 sense

<400> SEQUENCE: 111
ggacaagucu guggcccag                                              19
```

```
<210> SEQ ID NO 112
<211> LENGTH: 19
<212> TYPE: RNA
<213> ORGANISM: Artificial Sequence
<220> FEATURE:
<223> OTHER INFORMATION: si-TD509 antisense

<400> SEQUENCE: 112
cugggccaca gacuugucc                                                  19

<210> SEQ ID NO 113
<211> LENGTH: 19
<212> TYPE: RNA
<213> ORGANISM: Artificial Sequence
<220> FEATURE:
<223> OTHER INFORMATION: si-TD508 sense

<400> SEQUENCE: 113
uggacaaguc uguggccca                                                  19

<210> SEQ ID NO 114
<211> LENGTH: 19
<212> TYPE: RNA
<213> ORGANISM: Artificial Sequence
<220> FEATURE:
<223> OTHER INFORMATION: si-TD508 antisense

<400> SEQUENCE: 114
ugggccacag acuugucca                                                  19

<210> SEQ ID NO 115
<211> LENGTH: 19
<212> TYPE: RNA
<213> ORGANISM: Artificial Sequence
<220> FEATURE:
<223> OTHER INFORMATION: si-TD577 sense

<400> SEQUENCE: 115
gccucccugg aggagaucc                                                  19

<210> SEQ ID NO 116
<211> LENGTH: 19
<212> TYPE: RNA
<213> ORGANISM: Artificial Sequence
<220> FEATURE:
<223> OTHER INFORMATION: si-TD577 antisense

<400> SEQUENCE: 116
ggaucuccuc cagggaggc                                                  19

<210> SEQ ID NO 117
<211> LENGTH: 19
<212> TYPE: RNA
<213> ORGANISM: Artificial Sequence
<220> FEATURE:
<223> OTHER INFORMATION: si-TD611 sense

<400> SEQUENCE: 117
gguagcaagg aaacuggag                                                  19

<210> SEQ ID NO 118
<211> LENGTH: 19
<212> TYPE: RNA
<213> ORGANISM: Artificial Sequence
<220> FEATURE:
<223> OTHER INFORMATION: si-TD611 antisense
```

<400> SEQUENCE: 118
cuccaguuuc cuugcuacc                                              19

<210> SEQ ID NO 119
<211> LENGTH: 19
<212> TYPE: RNA
<213> ORGANISM: Artificial Sequence
<220> FEATURE:
<223> OTHER INFORMATION: si-TD609 sense

<400> SEQUENCE: 119
cugguagcaa ggaaacugg                                              19

<210> SEQ ID NO 120
<211> LENGTH: 19
<212> TYPE: RNA
<213> ORGANISM: Artificial Sequence
<220> FEATURE:
<223> OTHER INFORMATION: si-TD609 antisense

<400> SEQUENCE: 120
ccaguuuccu ugcuaccag                                              19

<210> SEQ ID NO 121
<211> LENGTH: 19
<212> TYPE: RNA
<213> ORGANISM: Artificial Sequence
<220> FEATURE:
<223> OTHER INFORMATION: si-TD607 sense

<400> SEQUENCE: 121
accugguagc aaggaaacu                                              19

<210> SEQ ID NO 122
<211> LENGTH: 19
<212> TYPE: RNA
<213> ORGANISM: Artificial Sequence
<220> FEATURE:
<223> OTHER INFORMATION: si-TD607 antisense

<400> SEQUENCE: 122 aguuccuug cuaccaggu                                               19

<210> SEQ ID NO 123
<211> LENGTH: 19
<212> TYPE: RNA
<213> ORGANISM: Artificial Sequence
<220> FEATURE:
<223> OTHER INFORMATION: si-TD604 sense

<400> SEQUENCE: 123
aggaccuggu agcaaggaa                                              19

<210> SEQ ID NO 124
<211> LENGTH: 19
<212> TYPE: RNA
<213> ORGANISM: Artificial Sequence
<220> FEATURE:
<223> OTHER INFORMATION: si-TD604 antisense

<400> SEQUENCE: 124
uuccuugcua ccagguccu                                              19

```
<210> SEQ ID NO 125
<211> LENGTH: 19
<212> TYPE: RNA
<213> ORGANISM: Artificial Sequence
<220> FEATURE:
<223> OTHER INFORMATION: si-TD600 sense

<400> SEQUENCE: 125
auccaggacc ugguagcaa                                                  19

<210> SEQ ID NO 126
<211> LENGTH: 19
<212> TYPE: RNA
<213> ORGANISM: Artificial Sequence
<220> FEATURE:
<223> OTHER INFORMATION: si-TD600 antisense

<400> SEQUENCE: 126
uugcuaccag guccuggau                                                  19

<210> SEQ ID NO 127
<211> LENGTH: 19
<212> TYPE: RNA
<213> ORGANISM: Artificial Sequence
<220> FEATURE:
<223> OTHER INFORMATION: si-TD598 sense

<400> SEQUENCE: 127
ggauccagga ccugguagc                                                  19

<210> SEQ ID NO 128
<211> LENGTH: 19
<212> TYPE: RNA
<213> ORGANISM: Artificial Sequence
<220> FEATURE:
<223> OTHER INFORMATION: si-TD598 antisense

<400> SEQUENCE: 128
gcuaccaggu ccuggaucc                                                  19

<210> SEQ ID NO 129
<211> LENGTH: 19
<212> TYPE: RNA
<213> ORGANISM: Artificial Sequence
<220> FEATURE:
<223> OTHER INFORMATION: si-TD596 sense

<400> SEQUENCE: 129
ccggauccag gaccuggua                                                  19

<210> SEQ ID NO 130
<211> LENGTH: 19
<212> TYPE: RNA
<213> ORGANISM: Artificial Sequence
<220> FEATURE:
<223> OTHER INFORMATION: si-TD596 antisense

<400> SEQUENCE: 130
uaccaggucc uggauccgg                                                  19

<210> SEQ ID NO 131
<211> LENGTH: 19
<212> TYPE: RNA
<213> ORGANISM: Artificial Sequence
<220> FEATURE:
<223> OTHER INFORMATION: si-TD588 sense
```

```
<400> SEQUENCE: 131
cagcuguccc ggauccagg                                           19

<210> SEQ ID NO 132
<211> LENGTH: 19
<212> TYPE: RNA
<213> ORGANISM: Artificial Sequence
<220> FEATURE:
<223> OTHER INFORMATION: si-TD588 antisense

<400> SEQUENCE: 132
ccuggauccg ggacagcug                                           19

<210> SEQ ID NO 133
<211> LENGTH: 19
<212> TYPE: RNA
<213> ORGANISM: Artificial Sequence
<220> FEATURE:
<223> OTHER INFORMATION: si-TD587 sense

<400> SEQUENCE: 133
gcagcugucc cggauccag                                           19

<210> SEQ ID NO 134
<211> LENGTH: 19
<212> TYPE: RNA
<213> ORGANISM: Artificial Sequence
<220> FEATURE:
<223> OTHER INFORMATION: si-TD587 antisense

<400> SEQUENCE: 134
cuggauccgg gacagcugc                                           19

<210> SEQ ID NO 135
<211> LENGTH: 19
<212> TYPE: RNA
<213> ORGANISM: Artificial Sequence
<220> FEATURE:
<223> OTHER INFORMATION: si-TD585 sense

<400> SEQUENCE: 135
gggcagcugu cccggaucc                                           19

<210> SEQ ID NO 136
<211> LENGTH: 19
<212> TYPE: RNA
<213> ORGANISM: Artificial Sequence
<220> FEATURE:
<223> OTHER INFORMATION: si-TD585 antisense

<400> SEQUENCE: 136
ggauccggga cagcugccc                                           19

<210> SEQ ID NO 137
<211> LENGTH: 19
<212> TYPE: RNA
<213> ORGANISM: Artificial Sequence
<220> FEATURE:
<223> OTHER INFORMATION: si-TD720 sense

<400> SEQUENCE: 137
gagcugagag accuguaca                                           19
```

```
<210> SEQ ID NO 138
<211> LENGTH: 19
<212> TYPE: RNA
<213> ORGANISM: Artificial Sequence
<220> FEATURE:
<223> OTHER INFORMATION: si-TD720 antisense

<400> SEQUENCE: 138
uguacagguc ucucagcuc                                                    19

<210> SEQ ID NO 139
<211> LENGTH: 19
<212> TYPE: RNA
<213> ORGANISM: Artificial Sequence
<220> FEATURE:
<223> OTHER INFORMATION: si-TD718 sense

<400> SEQUENCE: 139
gggagcugag agaccugua                                                    19

<210> SEQ ID NO 140
<211> LENGTH: 19
<212> TYPE: RNA
<213> ORGANISM: Artificial Sequence
<220> FEATURE:
<223> OTHER INFORMATION: si-TD718 antisense

<400> SEQUENCE: 140
uacaggucuc ucagcuccc                                                    19

<210> SEQ ID NO 141
<211> LENGTH: 19
<212> TYPE: RNA
<213> ORGANISM: Artificial Sequence
<220> FEATURE:
<223> OTHER INFORMATION: si-TD743 sense

<400> SEQUENCE: 141
gacucccacc ucagacaga                                                    19

<210> SEQ ID NO 142
<211> LENGTH: 19
<212> TYPE: RNA
<213> ORGANISM: Artificial Sequence
<220> FEATURE:
<223> OTHER INFORMATION: si-TD743 antisense

<400> SEQUENCE: 142
ucugucugag gugggaguc                                                    19

<210> SEQ ID NO 143
<211> LENGTH: 19
<212> TYPE: RNA
<213> ORGANISM: Artificial Sequence
<220> FEATURE:
<223> OTHER INFORMATION: si-TD145 sense

<400> SEQUENCE: 143
guaaaagaug agaaaaaua                                                    19

<210> SEQ ID NO 144
<211> LENGTH: 19
<212> TYPE: RNA
<213> ORGANISM: Artificial Sequence
<220> FEATURE:
<223> OTHER INFORMATION: si-TD145 antisense
```

```
<400> SEQUENCE: 144
uauuuuucuc aucuuuuac                                               19

<210> SEQ ID NO 145
<211> LENGTH: 19
<212> TYPE: RNA
<213> ORGANISM: Artificial Sequence
<220> FEATURE:
<223> OTHER INFORMATION: si-TD480 sense

<400> SEQUENCE: 145
ucuugugcug agagcuuuc                                               19

<210> SEQ ID NO 146
<211> LENGTH: 19
<212> TYPE: RNA
<213> ORGANISM: Artificial Sequence
<220> FEATURE:
<223> OTHER INFORMATION: si-TD480 antisense

<400> SEQUENCE: 146
gaaagcucuc agcacaaga                                               19

<210> SEQ ID NO 147
<211> LENGTH: 19
<212> TYPE: RNA
<213> ORGANISM: Artificial Sequence
<220> FEATURE:
<223> OTHER INFORMATION: si-TD483 sense

<400> SEQUENCE: 147
ugugcugaga gcuuucggg                                               19

<210> SEQ ID NO 148
<211> LENGTH: 19
<212> TYPE: RNA
<213> ORGANISM: Artificial Sequence
<220> FEATURE:
<223> OTHER INFORMATION: si-TD483 antisense

<400> SEQUENCE: 148
cccgaaagcu cucagcaca                                               19

<210> SEQ ID NO 149
<211> LENGTH: 19
<212> TYPE: RNA
<213> ORGANISM: Artificial Sequence
<220> FEATURE:
<223> OTHER INFORMATION: si-TD736 sense

<400> SEQUENCE: 149
acagacagau ggaccugca                                               19

<210> SEQ ID NO 150
<211> LENGTH: 19
<212> TYPE: RNA
<213> ORGANISM: Artificial Sequence
<220> FEATURE:
<223> OTHER INFORMATION: si-TD736 antisense

<400> SEQUENCE: 150
ugcaggucca ucugucugu                                               19
```

```
<210> SEQ ID NO 151
<211> LENGTH: 19
<212> TYPE: RNA
<213> ORGANISM: Artificial Sequence
<220> FEATURE:
<223> OTHER INFORMATION: si-TD734 sense

<400> SEQUENCE: 151
guacagacag auggaccug                                              19

<210> SEQ ID NO 152
<211> LENGTH: 19
<212> TYPE: RNA
<213> ORGANISM: Artificial Sequence
<220> FEATURE:
<223> OTHER INFORMATION: si-TD734 antisense

<400> SEQUENCE: 152
cagguccauc ugucuguac                                              19

<210> SEQ ID NO 153
<211> LENGTH: 19
<212> TYPE: RNA
<213> ORGANISM: Artificial Sequence
<220> FEATURE:
<223> OTHER INFORMATION: si-TD730 sense

<400> SEQUENCE: 153
accuguacag acagaugga                                              19

<210> SEQ ID NO 154
<211> LENGTH: 19
<212> TYPE: RNA
<213> ORGANISM: Artificial Sequence
<220> FEATURE:
<223> OTHER INFORMATION: si-TD730 antisense

<400> SEQUENCE: 154
uccaucuguc uguacaggu                                              19

<210> SEQ ID NO 155
<211> LENGTH: 19
<212> TYPE: RNA
<213> ORGANISM: Artificial Sequence
<220> FEATURE:
<223> OTHER INFORMATION: si-TD726 sense

<400> SEQUENCE: 155
agagaccugu acagacaga                                              19

<210> SEQ ID NO 156
<211> LENGTH: 19
<212> TYPE: RNA
<213> ORGANISM: Artificial Sequence
<220> FEATURE:
<223> OTHER INFORMATION: si-TD726 antisense

<400> SEQUENCE: 156
ucugucugua caggucucu                                              19

<210> SEQ ID NO 157
<211> LENGTH: 19
<212> TYPE: RNA
<213> ORGANISM: Artificial Sequence
<220> FEATURE:
<223> OTHER INFORMATION: si-TD723 sense
```

```
<400> SEQUENCE: 157
cugagagacc uguacagac                                                19

<210> SEQ ID NO 158
<211> LENGTH: 19
<212> TYPE: RNA
<213> ORGANISM: Artificial Sequence
<220> FEATURE:
<223> OTHER INFORMATION: si-TD723 antisense

<400> SEQUENCE: 158
gucuguacag gucucucag                                                19

<210> SEQ ID NO 159
<211> LENGTH: 19
<212> TYPE: RNA
<213> ORGANISM: Artificial Sequence
<220> FEATURE:
<223> OTHER INFORMATION: si-TD717 sense

<400> SEQUENCE: 159
agggagcuga gagaccugu                                                19

<210> SEQ ID NO 160
<211> LENGTH: 19
<212> TYPE: RNA
<213> ORGANISM: Artificial Sequence
<220> FEATURE:
<223> OTHER INFORMATION: si-TD717 antisense

<400> SEQUENCE: 160
acaggucucu cagcucccu                                                19

<210> SEQ ID NO 161
<211> LENGTH: 19
<212> TYPE: RNA
<213> ORGANISM: Artificial Sequence
<220> FEATURE:
<223> OTHER INFORMATION: si-7 sense

<400> SEQUENCE: 161
ugggagaugg gaagcgaaa                                                19

<210> SEQ ID NO 162
<211> LENGTH: 19
<212> TYPE: RNA
<213> ORGANISM: Artificial Sequence
<220> FEATURE:
<223> OTHER INFORMATION: si-7 antisense

<400> SEQUENCE: 162
uuucgcuucc caucuccca                                                19

<210> SEQ ID NO 163
<211> LENGTH: 19
<212> TYPE: RNA
<213> ORGANISM: Artificial Sequence
<220> FEATURE:
<223> OTHER INFORMATION: si-10 sense

<400> SEQUENCE: 163
cagacaaagg ggccaccua                                                19
```

```
<210> SEQ ID NO 164
<211> LENGTH: 19
<212> TYPE: RNA
<213> ORGANISM: Artificial Sequence
<220> FEATURE:
<223> OTHER INFORMATION: si-10 antisense

<400> SEQUENCE: 164
uagguggccc cuuugucug                                                  19

<210> SEQ ID NO 165
<211> LENGTH: 19
<212> TYPE: RNA
<213> ORGANISM: Artificial Sequence
<220> FEATURE:
<223> OTHER INFORMATION: si-1 sense

<400> SEQUENCE: 165
ggaccuggua gcaaggaaa                                                  19

<210> SEQ ID NO 166
<211> LENGTH: 19
<212> TYPE: RNA
<213> ORGANISM: Artificial Sequence
<220> FEATURE:
<223> OTHER INFORMATION: si-1 antisense

<400> SEQUENCE: 166
uuuccuugcu accaggucc                                                  19

<210> SEQ ID NO 167
<211> LENGTH: 20
<212> TYPE: DNA
<213> ORGANISM: Artificial Sequence
<220> FEATURE:
<223> OTHER INFORMATION: hCIKP1-F

<400> SEQUENCE: 167
ggaaccaacc tcttgtgctg                                                 20

<210> SEQ ID NO 168
<211> LENGTH: 20
<212> TYPE: DNA
<213> ORGANISM: Artificial Sequence
<220> FEATURE:
<223> OTHER INFORMATION: hCIKP1-R

<400> SEQUENCE: 168
gtcaacttct tgggtgcctg                                                 20

<210> SEQ ID NO 169
<211> LENGTH: 23
<212> TYPE: DNA
<213> ORGANISM: Artificial Sequence
<220> FEATURE:
<223> OTHER INFORMATION: hGADPH-F

<400> SEQUENCE: 169
catgagaagt atgacaacag cct                                             23

<210> SEQ ID NO 170
<211> LENGTH: 22
<212> TYPE: DNA
<213> ORGANISM: Artificial Sequence
<220> FEATURE:
<223> OTHER INFORMATION: hGADPH-R
```

```
<400> SEQUENCE: 170
agtccttcca cgataccaaa gt                                              22

<210> SEQ ID NO 171
<211> LENGTH: 18
<212> TYPE: DNA
<213> ORGANISM: Artificial Sequence
<220> FEATURE:
<223> OTHER INFORMATION: mouse TNF-a-F

<400> SEQUENCE: 171
tcagcgagga cagcaagg                                                   18

<210> SEQ ID NO 172
<211> LENGTH: 22
<212> TYPE: DNA
<213> ORGANISM: Artificial Sequence
<220> FEATURE:
<223> OTHER INFORMATION: mouse TNFa-R

<400> SEQUENCE: 172
agtgagtgaa agggacagaa cc                                              22

<210> SEQ ID NO 173
<211> LENGTH: 20
<212> TYPE: DNA
<213> ORGANISM: Artificial Sequence
<220> FEATURE:
<223> OTHER INFORMATION: mouse IL6-F

<400> SEQUENCE: 173
ccttcttggg actgatgctg                                                 20

<210> SEQ ID NO 174
<211> LENGTH: 22
<212> TYPE: DNA
<213> ORGANISM: Artificial Sequence
<220> FEATURE:
<223> OTHER INFORMATION: mouse IL6-R

<400> SEQUENCE: 174
ttgggagtgg tatcctctgt ga                                              22

<210> SEQ ID NO 175
<211> LENGTH: 24
<212> TYPE: DNA
<213> ORGANISM: Artificial Sequence
<220> FEATURE:
<223> OTHER INFORMATION: mouse GAPDH-F

<400> SEQUENCE: 175
ccttcattga cctcaactac atgg                                            24

<210> SEQ ID NO 176
<211> LENGTH: 20
<212> TYPE: DNA
<213> ORGANISM: Artificial Sequence
<220> FEATURE:
<223> OTHER INFORMATION: mouse GAPDH-R

<400> SEQUENCE: 176
ctcgctcctg gaagatggtg                                                 20
```

```
<210> SEQ ID NO 177
<211> LENGTH: 20
<212> TYPE: DNA
<213> ORGANISM: Artificial Sequence
<220> FEATURE:
<223> OTHER INFORMATION: ALP-F

<400> SEQUENCE: 177
gtcagctcca ccacaaccct                                                 20

<210> SEQ ID NO 178
<211> LENGTH: 20
<212> TYPE: DNA
<213> ORGANISM: Artificial Sequence
<220> FEATURE:
<223> OTHER INFORMATION: ALP-R

<400> SEQUENCE: 178
gccctcattg gccttcaccc                                                 20

<210> SEQ ID NO 179
<211> LENGTH: 20
<212> TYPE: DNA
<213> ORGANISM: Artificial Sequence
<220> FEATURE:
<223> OTHER INFORMATION: COL1-F

<400> SEQUENCE: 179
cactggtgat gctggtcctg                                                 20

<210> SEQ ID NO 180
<211> LENGTH: 19
<212> TYPE: DNA
<213> ORGANISM: Artificial Sequence
<220> FEATURE:
<223> OTHER INFORMATION: COL1-R

<400> SEQUENCE: 180
cgaggtcacg gtcacgaac                                                  19

<210> SEQ ID NO 181
<211> LENGTH: 20
<212> TYPE: DNA
<213> ORGANISM: Artificial Sequence
<220> FEATURE:
<223> OTHER INFORMATION: OPN-F

<400> SEQUENCE: 181
gtaccctgat gctacagacg                                                 20

<210> SEQ ID NO 182
<211> LENGTH: 20
<212> TYPE: DNA
<213> ORGANISM: Artificial Sequence
<220> FEATURE:
<223> OTHER INFORMATION: OPN-R

<400> SEQUENCE: 182
ttcataactg tccttcccac                                                 20

<210> SEQ ID NO 183
<211> LENGTH: 20
<212> TYPE: DNA
<213> ORGANISM: Artificial Sequence
<220> FEATURE:
<223> OTHER INFORMATION: BSP-F
```

```
<400> SEQUENCE: 183
ggcacctcga agacaacaac                                              20

<210> SEQ ID NO 184
<211> LENGTH: 20
<212> TYPE: DNA
<213> ORGANISM: Artificial Sequence
<220> FEATURE:
<223> OTHER INFORMATION: BSP-R

<400> SEQUENCE: 184
gcccgtgtat tcgtactccc                                              20

<210> SEQ ID NO 185
<211> LENGTH: 20
<212> TYPE: DNA
<213> ORGANISM: Artificial Sequence
<220> FEATURE:
<223> OTHER INFORMATION: OC-F

<400> SEQUENCE: 185
agggcagcga ggtagtgaag                                              20

<210> SEQ ID NO 186
<211> LENGTH: 20
<212> TYPE: DNA
<213> ORGANISM: Artificial Sequence
<220> FEATURE:
<223> OTHER INFORMATION: OC-R

<400> SEQUENCE: 186
tgtggtcagc caactcgtca                                              20

<210> SEQ ID NO 187
<211> LENGTH: 21
<212> TYPE: DNA
<213> ORGANISM: Artificial Sequence
<220> FEATURE:
<223> OTHER INFORMATION: GAPDH-F

<400> SEQUENCE: 187
ggcatggact gtggtcatga g                                            21

<210> SEQ ID NO 188
<211> LENGTH: 20
<212> TYPE: DNA
<213> ORGANISM: Artificial Sequence
<220> FEATURE:
<223> OTHER INFORMATION: GAPDH-R

<400> SEQUENCE: 188
tgcaccacca actgcttagc                                              20

<210> SEQ ID NO 189
<211> LENGTH: 19
<212> TYPE: DNA
<213> ORGANISM: Artificial Sequence
<220> FEATURE:
<223> OTHER INFORMATION: mouse IL-17A-F

<400> SEQUENCE: 189
ctccaccgca atgaagacc                                               19
```

<210> SEQ ID NO 190
<211> LENGTH: 20
<212> TYPE: DNA
<213> ORGANISM: Artificial Sequence
<220> FEATURE:
<223> OTHER INFORMATION: mouse IL-17A-R

<400> SEQUENCE: 190
ccctcttcag gaccaggatc                                               20

<210> SEQ ID NO 191
<211> LENGTH: 21
<212> TYPE: DNA
<213> ORGANISM: Artificial Sequence
<220> FEATURE:
<223> OTHER INFORMATION: mouse CKIP-1-F

<400> SEQUENCE: 191
tttctcggcc ttgggaaaaa c                                             21

<210> SEQ ID NO 192
<211> LENGTH: 19
<212> TYPE: DNA
<213> ORGANISM: Artificial Sequence
<220> FEATURE:
<223> OTHER INFORMATION: mouse CKIP-1-R

<400> SEQUENCE: 192
gaggcacatc ggctcttct                                                19

<210> SEQ ID NO 193
<211> LENGTH: 21
<212> TYPE: DNA
<213> ORGANISM: Artificial Sequence
<220> FEATURE:
<223> OTHER INFORMATION: si-TD

<400> SEQUENCE: 193
cgcccgagaa ggucggcugt t                                             21

<210> SEQ ID NO 194
<211> LENGTH: 21
<212> TYPE: DNA
<213> ORGANISM: Artificial Sequence
<220> FEATURE:
<223> OTHER INFORMATION: si-TD

<400> SEQUENCE: 194
cagccgaccu ucucgggcgt t                                             21

<210> SEQ ID NO 195
<211> LENGTH: 21
<212> TYPE: DNA
<213> ORGANISM: Artificial Sequence
<220> FEATURE:
<223> OTHER INFORMATION: si-TD

<400> SEQUENCE: 195
gcccgagaag gucggcuggt t                                             21

<210> SEQ ID NO 196
<211> LENGTH: 21
<212> TYPE: DNA
<213> ORGANISM: Artificial Sequence
<220> FEATURE:
<223> OTHER INFORMATION: si-TD

<400> SEQUENCE: 196
ccagccgacc uucucgggct t         21

<210> SEQ ID NO 197
<211> LENGTH: 21
<212> TYPE: DNA
<213> ORGANISM: Artificial Sequence
<220> FEATURE:
<223> OTHER INFORMATION: si-TD

<400> SEQUENCE: 197
cccgagaagg ucggcugggt t         21

<210> SEQ ID NO 198
<211> LENGTH: 21
<212> TYPE: DNA
<213> ORGANISM: Artificial Sequence
<220> FEATURE:
<223> OTHER INFORMATION: si-TD

<400> SEQUENCE: 198
cccagccgac cuucucgggt t         21

<210> SEQ ID NO 199
<211> LENGTH: 21
<212> TYPE: DNA
<213> ORGANISM: Artificial Sequence
<220> FEATURE:
<223> OTHER INFORMATION: si-TD

<400> SEQUENCE: 199
ccgagaaggu cggcugggut t         21

<210> SEQ ID NO 200
<211> LENGTH: 21
<212> TYPE: DNA
<213> ORGANISM: Artificial Sequence
<220> FEATURE:
<223> OTHER INFORMATION: si-TD

<400> SEQUENCE: 200
acccagccga ccuucucggt t         21

<210> SEQ ID NO 201
<211> LENGTH: 21
<212> TYPE: DNA
<213> ORGANISM: Artificial Sequence
<220> FEATURE:
<223> OTHER INFORMATION: si-TD

<400> SEQUENCE: 201
cgagaagguc ggcuggguct t         21

<210> SEQ ID NO 202
<211> LENGTH: 21
<212> TYPE: DNA
<213> ORGANISM: Artificial Sequence
<220> FEATURE:
<223> OTHER INFORMATION: si-TD

<400> SEQUENCE: 202
gacccagccg accuucucgt t         21

<210> SEQ ID NO 203
<211> LENGTH: 21
<212> TYPE: DNA
<213> ORGANISM: Artificial Sequence
<220> FEATURE:
<223> OTHER INFORMATION: si-TD

<400> SEQUENCE: 203
gagaaggucg gcugggucct t                                              21

<210> SEQ ID NO 204
<211> LENGTH: 21
<212> TYPE: DNA
<213> ORGANISM: Artificial Sequence
<220> FEATURE:
<223> OTHER INFORMATION: si-TD

<400> SEQUENCE: 204
ggacccagcc gaccuucuct t                                              21

<210> SEQ ID NO 205
<211> LENGTH: 21
<212> TYPE: DNA
<213> ORGANISM: Artificial Sequence
<220> FEATURE:
<223> OTHER INFORMATION: si-TD

<400> SEQUENCE: 205
agaaggucgg cuggguccgt t                                              21

<210> SEQ ID NO 206
<211> LENGTH: 21
<212> TYPE: DNA
<213> ORGANISM: Artificial Sequence
<220> FEATURE:
<223> OTHER INFORMATION: si-TD

<400> SEQUENCE: 206
cggacccagc cgaccuucut t                                              21

<210> SEQ ID NO 207
<211> LENGTH: 21
<212> TYPE: DNA
<213> ORGANISM: Artificial Sequence
<220> FEATURE:
<223> OTHER INFORMATION: si-TD

<400> SEQUENCE: 207
gaaggucggc uggguccggt t                                              21

<210> SEQ ID NO 208
<211> LENGTH: 21
<212> TYPE: DNA
<213> ORGANISM: Artificial Sequence
<220> FEATURE:
<223> OTHER INFORMATION: si-TD

<400> SEQUENCE: 208
ccggacccag ccgaccuuct t                                              21

<210> SEQ ID NO 209
<211> LENGTH: 21
<212> TYPE: DNA
<213> ORGANISM: Artificial Sequence
<220> FEATURE:
<223> OTHER INFORMATION: si-TD

<400> SEQUENCE: 209
aaggucggcu ggguccggat t                                              21

<210> SEQ ID NO 210
<211> LENGTH: 21
<212> TYPE: DNA
<213> ORGANISM: Artificial Sequence
<220> FEATURE:
<223> OTHER INFORMATION: si-TD

<400> SEQUENCE: 210
uccggaccca gccgaccuut t                                              21

<210> SEQ ID NO 211
<211> LENGTH: 21
<212> TYPE: DNA
<213> ORGANISM: Artificial Sequence
<220> FEATURE:
<223> OTHER INFORMATION: si-TD

<400> SEQUENCE: 211
aggucggcug gguccggaat t                                              21

<210> SEQ ID NO 212
<211> LENGTH: 21
<212> TYPE: DNA
<213> ORGANISM: Artificial Sequence
<220> FEATURE:
<223> OTHER INFORMATION: si-TD

<400> SEQUENCE: 212
uuccggaccc agccgaccut t                                              21

<210> SEQ ID NO 213
<211> LENGTH: 21
<212> TYPE: DNA
<213> ORGANISM: Artificial Sequence
<220> FEATURE:
<223> OTHER INFORMATION: si-TD

<400> SEQUENCE: 213
gucggcuggg uccggaaaut t                                              21

<210> SEQ ID NO 214
<211> LENGTH: 21
<212> TYPE: DNA
<213> ORGANISM: Artificial Sequence
<220> FEATURE:
<223> OTHER INFORMATION: si-TD

<400> SEQUENCE: 214
auuuccggac ccagccgact t                                              21

<210> SEQ ID NO 215
<211> LENGTH: 21
<212> TYPE: DNA
<213> ORGANISM: Artificial Sequence
<220> FEATURE:
<223> OTHER INFORMATION: si-TD

<400> SEQUENCE: 215
ucggcugggu ccggaaauut t                                              21

```
<210> SEQ ID NO 216
<211> LENGTH: 21
<212> TYPE: DNA
<213> ORGANISM: Artificial Sequence
<220> FEATURE:
<223> OTHER INFORMATION: si-TD

<400> SEQUENCE: 216
aauuuccgga cccagccgat t                                              21

<210> SEQ ID NO 217
<211> LENGTH: 21
<212> TYPE: DNA
<213> ORGANISM: Artificial Sequence
<220> FEATURE:
<223> OTHER INFORMATION: si-TD

<400> SEQUENCE: 217
cggcuggguc cggaaauuct t                                              21

<210> SEQ ID NO 218
<211> LENGTH: 21
<212> TYPE: DNA
<213> ORGANISM: Artificial Sequence
<220> FEATURE:
<223> OTHER INFORMATION: si-TD

<400> SEQUENCE: 218 gaauuccgg acccagccgt t                                               21

<210> SEQ ID NO 219
<211> LENGTH: 21
<212> TYPE: DNA
<213> ORGANISM: Artificial Sequence
<220> FEATURE:
<223> OTHER INFORMATION: si-TD

<400> SEQUENCE: 219
ggcugggucc ggaaauucut t                                              21

<210> SEQ ID NO 220
<211> LENGTH: 21
<212> TYPE: DNA
<213> ORGANISM: Artificial Sequence
<220> FEATURE:
<223> OTHER INFORMATION: si-TD

<400> SEQUENCE: 220
agaauuuccg gacccagcct t                                              21

<210> SEQ ID NO 221
<211> LENGTH: 21
<212> TYPE: DNA
<213> ORGANISM: Artificial Sequence
<220> FEATURE:
<223> OTHER INFORMATION: si-TD

<400> SEQUENCE: 221
gcuggguccg gaaauucugt t                                              21

<210> SEQ ID NO 222
<211> LENGTH: 21
<212> TYPE: DNA
<213> ORGANISM: Artificial Sequence
<220> FEATURE:
<223> OTHER INFORMATION: si-TD
```

```
<400> SEQUENCE: 222
cagaauuucc ggacccagct t                                              21

<210> SEQ ID NO 223
<211> LENGTH: 21
<212> TYPE: DNA
<213> ORGANISM: Artificial Sequence
<220> FEATURE:
<223> OTHER INFORMATION: si-TD

<400> SEQUENCE: 223
cuggguccgg aaauucugct t                                              21

<210> SEQ ID NO 224
<211> LENGTH: 21
<212> TYPE: DNA
<213> ORGANISM: Artificial Sequence
<220> FEATURE:
<223> OTHER INFORMATION: si-TD

<400> SEQUENCE: 224
gcagaauuuc cggacccagt t                                              21

<210> SEQ ID NO 225
<211> LENGTH: 21
<212> TYPE: DNA
<213> ORGANISM: Artificial Sequence
<220> FEATURE:
<223> OTHER INFORMATION: si-TD

<400> SEQUENCE: 225
uggguccgga aauucugcgt t                                              21

<210> SEQ ID NO 226
<211> LENGTH: 21
<212> TYPE: DNA
<213> ORGANISM: Artificial Sequence
<220> FEATURE:
<223> OTHER INFORMATION: si-TD

<400> SEQUENCE: 226
cgcagaauuu ccggacccat t                                              21

<210> SEQ ID NO 227
<211> LENGTH: 21
<212> TYPE: DNA
<213> ORGANISM: Artificial Sequence
<220> FEATURE:
<223> OTHER INFORMATION: si-TD

<400> SEQUENCE: 227
ggguccggaa auucugcggt t                                              21

<210> SEQ ID NO 228
<211> LENGTH: 21
<212> TYPE: DNA
<213> ORGANISM: Artificial Sequence
<220> FEATURE:
<223> OTHER INFORMATION: si-TD

<400> SEQUENCE: 228
ccgcagaauu uccggaccct t                                              21
```

```
<210> SEQ ID NO 229
<211> LENGTH: 21
<212> TYPE: DNA
<213> ORGANISM: Artificial Sequence
<220> FEATURE:
<223> OTHER INFORMATION: si-TD

<400> SEQUENCE: 229
gguccggaaa uucugcgggt t                                              21

<210> SEQ ID NO 230
<211> LENGTH: 21
<212> TYPE: DNA
<213> ORGANISM: Artificial Sequence
<220> FEATURE:
<223> OTHER INFORMATION: si-TD

<400> SEQUENCE: 230
cccgcagaau uuccggacct t                                              21

<210> SEQ ID NO 231
<211> LENGTH: 21
<212> TYPE: DNA
<213> ORGANISM: Artificial Sequence
<220> FEATURE:
<223> OTHER INFORMATION: si-TD

<400> SEQUENCE: 231
guccggaaau ucugcgggat t                                              21

<210> SEQ ID NO 232
<211> LENGTH: 21
<212> TYPE: DNA
<213> ORGANISM: Artificial Sequence
<220> FEATURE:
<223> OTHER INFORMATION: si-TD

<400> SEQUENCE: 232
ucccgcagaa uuuccggact t                                              21

<210> SEQ ID NO 233
<211> LENGTH: 21
<212> TYPE: DNA
<213> ORGANISM: Artificial Sequence
<220> FEATURE:
<223> OTHER INFORMATION: si-TD

<400> SEQUENCE: 233
uccggaaauu cugcgggaat t                                              21

<210> SEQ ID NO 234
<211> LENGTH: 21
<212> TYPE: DNA
<213> ORGANISM: Artificial Sequence
<220> FEATURE:
<223> OTHER INFORMATION: si-TD

<400> SEQUENCE: 234
uucccgcaga auuccggat t                                               21

<210> SEQ ID NO 235
<211> LENGTH: 21
<212> TYPE: DNA
<213> ORGANISM: Artificial Sequence
<220> FEATURE:
<223> OTHER INFORMATION: si-TD
```

<400> SEQUENCE: 235
cggaaauucu gcgggaaagt t    21

<210> SEQ ID NO 236
<211> LENGTH: 21
<212> TYPE: DNA
<213> ORGANISM: Artificial Sequence
<220> FEATURE:
<223> OTHER INFORMATION: si-TD

<400> SEQUENCE: 236
cuuucccgca gaauuuccgt t    21

<210> SEQ ID NO 237
<211> LENGTH: 21
<212> TYPE: DNA
<213> ORGANISM: Artificial Sequence
<220> FEATURE:
<223> OTHER INFORMATION: si-TD

<400> SEQUENCE: 237
ggaaauucug cgggaaaggt t    21

<210> SEQ ID NO 238
<211> LENGTH: 21
<212> TYPE: DNA
<213> ORGANISM: Artificial Sequence
<220> FEATURE:
<223> OTHER INFORMATION: si-TD

<400> SEQUENCE: 238
ccuuucccgc agaauuucct t    21

<210> SEQ ID NO 239
<211> LENGTH: 21
<212> TYPE: DNA
<213> ORGANISM: Artificial Sequence
<220> FEATURE:
<223> OTHER INFORMATION: si-TD

<400> SEQUENCE: 239 gaaaucugc gggaaagggt t    21

<210> SEQ ID NO 240
<211> LENGTH: 21
<212> TYPE: DNA
<213> ORGANISM: Artificial Sequence
<220> FEATURE:
<223> OTHER INFORMATION: si-TD

<400> SEQUENCE: 240
cccuuucccg cagaauuuct t    21

<210> SEQ ID NO 241
<211> LENGTH: 21
<212> TYPE: DNA
<213> ORGANISM: Artificial Sequence
<220> FEATURE:
<223> OTHER INFORMATION: si-TD

<400> SEQUENCE: 241
aaauucugcg ggaaagggat t    21

```
<210> SEQ ID NO 242
<211> LENGTH: 21
<212> TYPE: DNA
<213> ORGANISM: Artificial Sequence
<220> FEATURE:
<223> OTHER INFORMATION: si-TD

<400> SEQUENCE: 242 ucccuuccc gcagaauuut t                                          21

<210> SEQ ID NO 243
<211> LENGTH: 21
<212> TYPE: DNA
<213> ORGANISM: Artificial Sequence
<220> FEATURE:
<223> OTHER INFORMATION: si-TD

<400> SEQUENCE: 243
aauucugcgg gaaagggaut t                                         21

<210> SEQ ID NO 244
<211> LENGTH: 21
<212> TYPE: DNA
<213> ORGANISM: Artificial Sequence
<220> FEATURE:
<223> OTHER INFORMATION: si-TD

<400> SEQUENCE: 244
aucccuuucc cgcagaauut t                                         21

<210> SEQ ID NO 245
<211> LENGTH: 21
<212> TYPE: DNA
<213> ORGANISM: Artificial Sequence
<220> FEATURE:
<223> OTHER INFORMATION: si-TD

<400> SEQUENCE: 245
auucugcggg aaagggauut t                                         21

<210> SEQ ID NO 246
<211> LENGTH: 21
<212> TYPE: DNA
<213> ORGANISM: Artificial Sequence
<220> FEATURE:
<223> OTHER INFORMATION: si-TD

<400> SEQUENCE: 246
aaucccuuuc ccgcagaaut t                                         21

<210> SEQ ID NO 247
<211> LENGTH: 21
<212> TYPE: DNA
<213> ORGANISM: Artificial Sequence
<220> FEATURE:
<223> OTHER INFORMATION: si-TD

<400> SEQUENCE: 247
uucugcggga aagggauuut t                                         21

<210> SEQ ID NO 248
<211> LENGTH: 21
<212> TYPE: DNA
<213> ORGANISM: Artificial Sequence
<220> FEATURE:
<223> OTHER INFORMATION: si-TD
```

<400> SEQUENCE: 248
aaaucccuuu cccgcagaat t    21

<210> SEQ ID NO 249
<211> LENGTH: 21
<212> TYPE: DNA
<213> ORGANISM: Artificial Sequence
<220> FEATURE:
<223> OTHER INFORMATION: si-TD

<400> SEQUENCE: 249
ucugcgggaa agggauuuut t    21

<210> SEQ ID NO 250
<211> LENGTH: 21
<212> TYPE: DNA
<213> ORGANISM: Artificial Sequence
<220> FEATURE:
<223> OTHER INFORMATION: si-TD

<400> SEQUENCE: 250
aaaaucccuu ucccgcagat t    21

<210> SEQ ID NO 251
<211> LENGTH: 21
<212> TYPE: DNA
<213> ORGANISM: Artificial Sequence
<220> FEATURE:
<223> OTHER INFORMATION: si-TD

<400> SEQUENCE: 251
cugcgggaaa gggauuuuct t    21

<210> SEQ ID NO 252
<211> LENGTH: 21
<212> TYPE: DNA
<213> ORGANISM: Artificial Sequence
<220> FEATURE:
<223> OTHER INFORMATION: si-TD

<400> SEQUENCE: 252
gaaaaucccu ucccgcagt t    21

<210> SEQ ID NO 253
<211> LENGTH: 21
<212> TYPE: DNA
<213> ORGANISM: Artificial Sequence
<220> FEATURE:
<223> OTHER INFORMATION: si-TD

<400> SEQUENCE: 253
ugcgggaaag ggauuuucat t    21

<210> SEQ ID NO 254
<211> LENGTH: 21
<212> TYPE: DNA
<213> ORGANISM: Artificial Sequence
<220> FEATURE:
<223> OTHER INFORMATION: si-TD

<400> SEQUENCE: 254 ugaaaaucccc uuucccgcat t    21

-continued

```
<210> SEQ ID NO 255
<211> LENGTH: 21
<212> TYPE: DNA
<213> ORGANISM: Artificial Sequence
<220> FEATURE:
<223> OTHER INFORMATION: si-TD

<400> SEQUENCE: 255
gcgggaaagg gauuuucagt t                                             21

<210> SEQ ID NO 256
<211> LENGTH: 21
<212> TYPE: DNA
<213> ORGANISM: Artificial Sequence
<220> FEATURE:
<223> OTHER INFORMATION: si-TD

<400> SEQUENCE: 256
cugaaaaucc cuuucccgct t                                             21

<210> SEQ ID NO 257
<211> LENGTH: 21
<212> TYPE: DNA
<213> ORGANISM: Artificial Sequence
<220> FEATURE:
<223> OTHER INFORMATION: si-TD

<400> SEQUENCE: 257
cgggaaaggg auuuucaggt t                                             21

<210> SEQ ID NO 258
<211> LENGTH: 21
<212> TYPE: DNA
<213> ORGANISM: Artificial Sequence
<220> FEATURE:
<223> OTHER INFORMATION: si-TD

<400> SEQUENCE: 258
ccugaaaauc cuuucccgt t                                              21

<210> SEQ ID NO 259
<211> LENGTH: 21
<212> TYPE: DNA
<213> ORGANISM: Artificial Sequence
<220> FEATURE:
<223> OTHER INFORMATION: si-TD

<400> SEQUENCE: 259
gggaaaggga uuuucagggt t                                             21

<210> SEQ ID NO 260
<211> LENGTH: 21
<212> TYPE: DNA
<213> ORGANISM: Artificial Sequence
<220> FEATURE:
<223> OTHER INFORMATION: si-TD

<400> SEQUENCE: 260
cccugaaaau cccuuuccct t                                             21

<210> SEQ ID NO 261
<211> LENGTH: 21
<212> TYPE: DNA
<213> ORGANISM: Artificial Sequence
<220> FEATURE:
<223> OTHER INFORMATION: si-TD
```

<400> SEQUENCE: 261
ggaaagggau uucagggat t                                       21

<210> SEQ ID NO 262
<211> LENGTH: 21
<212> TYPE: DNA
<213> ORGANISM: Artificial Sequence
<220> FEATURE:
<223> OTHER INFORMATION: si-TD

<400> SEQUENCE: 262
ucccugaaaa ucccuuucct t                                      21

<210> SEQ ID NO 263
<211> LENGTH: 21
<212> TYPE: DNA
<213> ORGANISM: Artificial Sequence
<220> FEATURE:
<223> OTHER INFORMATION: si-TD

<400> SEQUENCE: 263
gaaagggauu uucagggagt t                                      21

<210> SEQ ID NO 264
<211> LENGTH: 21
<212> TYPE: DNA
<213> ORGANISM: Artificial Sequence
<220> FEATURE:
<223> OTHER INFORMATION: si-TD

<400> SEQUENCE: 264
cucccugaaa aucccuuuct t                                      21

<210> SEQ ID NO 265
<211> LENGTH: 21
<212> TYPE: DNA
<213> ORGANISM: Artificial Sequence
<220> FEATURE:
<223> OTHER INFORMATION: si-TD

<400> SEQUENCE: 265
aaagggauuu ucagggagat t                                      21

<210> SEQ ID NO 266
<211> LENGTH: 21
<212> TYPE: DNA
<213> ORGANISM: Artificial Sequence
<220> FEATURE:
<223> OTHER INFORMATION: si-TD

<400> SEQUENCE: 266
ucucccugaa aaucccuuut t                                      21

<210> SEQ ID NO 267
<211> LENGTH: 21
<212> TYPE: DNA
<213> ORGANISM: Artificial Sequence
<220> FEATURE:
<223> OTHER INFORMATION: si-TD

<400> SEQUENCE: 267
aagggauuuu cagggagaut t                                      21

```
<210> SEQ ID NO 268
<211> LENGTH: 21
<212> TYPE: DNA
<213> ORGANISM: Artificial Sequence
<220> FEATURE:
<223> OTHER INFORMATION: si-TD

<400> SEQUENCE: 268
aucucccuga aaaucccuut t                                              21

<210> SEQ ID NO 269
<211> LENGTH: 21
<212> TYPE: DNA
<213> ORGANISM: Artificial Sequence
<220> FEATURE:
<223> OTHER INFORMATION: si-TD

<400> SEQUENCE: 269
agggauuuuc agggagauut t                                              21

<210> SEQ ID NO 270
<211> LENGTH: 21
<212> TYPE: DNA
<213> ORGANISM: Artificial Sequence
<220> FEATURE:
<223> OTHER INFORMATION: si-TD

<400> SEQUENCE: 270
aaucucccug aaaauccut t                                               21

<210> SEQ ID NO 271
<211> LENGTH: 21
<212> TYPE: DNA
<213> ORGANISM: Artificial Sequence
<220> FEATURE:
<223> OTHER INFORMATION: si-TD

<400> SEQUENCE: 271
gggauuuuca gggagauuut t                                              21

<210> SEQ ID NO 272
<211> LENGTH: 21
<212> TYPE: DNA
<213> ORGANISM: Artificial Sequence
<220> FEATURE:
<223> OTHER INFORMATION: si-TD

<400> SEQUENCE: 272
aaaucucccu gaaaauccct t                                              21

<210> SEQ ID NO 273
<211> LENGTH: 21
<212> TYPE: DNA
<213> ORGANISM: Artificial Sequence
<220> FEATURE:
<223> OTHER INFORMATION: si-TD

<400> SEQUENCE: 273
ggauuuucag ggagauuugt t                                              21

<210> SEQ ID NO 274
<211> LENGTH: 21
<212> TYPE: DNA
<213> ORGANISM: Artificial Sequence
<220> FEATURE:
<223> OTHER INFORMATION: si-TD
```

```
<400> SEQUENCE: 274
caaaucuccc ugaaaaucct t                                              21

<210> SEQ ID NO 275
<211> LENGTH: 21
<212> TYPE: DNA
<213> ORGANISM: Artificial Sequence
<220> FEATURE:
<223> OTHER INFORMATION: si-TD

<400> SEQUENCE: 275 gauuucagg gagauuuggt t                                               21

<210> SEQ ID NO 276
<211> LENGTH: 21
<212> TYPE: DNA
<213> ORGANISM: Artificial Sequence
<220> FEATURE:
<223> OTHER INFORMATION: si-TD

<400> SEQUENCE: 276
ccaaaucucc cugaaaauct t                                              21

<210> SEQ ID NO 277
<211> LENGTH: 21
<212> TYPE: DNA
<213> ORGANISM: Artificial Sequence
<220> FEATURE:
<223> OTHER INFORMATION: si-TD

<400> SEQUENCE: 277 auuucaggg agauuuggat t                                               21

<210> SEQ ID NO 278
<211> LENGTH: 21
<212> TYPE: DNA
<213> ORGANISM: Artificial Sequence
<220> FEATURE:
<223> OTHER INFORMATION: si-TD

<400> SEQUENCE: 278
uccaaaucuc ccugaaaaut t                                              21

<210> SEQ ID NO 279
<211> LENGTH: 21
<212> TYPE: DNA
<213> ORGANISM: Artificial Sequence
<220> FEATURE:
<223> OTHER INFORMATION: si-TD

<400> SEQUENCE: 279
uuuucaggga gauuuggaat t                                              21

<210> SEQ ID NO 280
<211> LENGTH: 21
<212> TYPE: DNA
<213> ORGANISM: Artificial Sequence
<220> FEATURE:
<223> OTHER INFORMATION: si-TD

<400> SEQUENCE: 280
uuccaaaucu cccugaaaat t                                              21
```

```
<210> SEQ ID NO 281
<211> LENGTH: 21
<212> TYPE: DNA
<213> ORGANISM: Artificial Sequence
<220> FEATURE:
<223> OTHER INFORMATION: si-TD

<400> SEQUENCE: 281
uuucagggag auuuggaaat t                                              21

<210> SEQ ID NO 282
<211> LENGTH: 21
<212> TYPE: DNA
<213> ORGANISM: Artificial Sequence
<220> FEATURE:
<223> OTHER INFORMATION: si-TD

<400> SEQUENCE: 282
uuuccaaauc ucccugaaat t                                              21

<210> SEQ ID NO 283
<211> LENGTH: 21
<212> TYPE: DNA
<213> ORGANISM: Artificial Sequence
<220> FEATURE:
<223> OTHER INFORMATION: si-TD

<400> SEQUENCE: 283
uucagggaga uuuggaaaat t                                              21

<210> SEQ ID NO 284
<211> LENGTH: 21
<212> TYPE: DNA
<213> ORGANISM: Artificial Sequence
<220> FEATURE:
<223> OTHER INFORMATION: si-TD

<400> SEQUENCE: 284
uuuuccaaau cucccugaat t                                              21

<210> SEQ ID NO 285
<211> LENGTH: 21
<212> TYPE: DNA
<213> ORGANISM: Artificial Sequence
<220> FEATURE:
<223> OTHER INFORMATION: si-TD

<400> SEQUENCE: 285
ucagggagau uuggaaaaat t                                              21

<210> SEQ ID NO 286
<211> LENGTH: 21
<212> TYPE: DNA
<213> ORGANISM: Artificial Sequence
<220> FEATURE:
<223> OTHER INFORMATION: si-TD

<400> SEQUENCE: 286
uuuuuccaaa ucucccugat t                                              21

<210> SEQ ID NO 287
<211> LENGTH: 21
<212> TYPE: DNA
<213> ORGANISM: Artificial Sequence
<220> FEATURE:
<223> OTHER INFORMATION: si-TD
```

<400> SEQUENCE: 287 caggagauu uggaaaaact t                     21

<210> SEQ ID NO 288
<211> LENGTH: 21
<212> TYPE: DNA
<213> ORGANISM: Artificial Sequence
<220> FEATURE:
<223> OTHER INFORMATION: si-TD

<400> SEQUENCE: 288 guuuuccaa aucuccugt t                      21

<210> SEQ ID NO 289
<211> LENGTH: 21
<212> TYPE: DNA
<213> ORGANISM: Artificial Sequence
<220> FEATURE:
<223> OTHER INFORMATION: si-TD

<400> SEQUENCE: 289
agggagauuu ggaaaaacct t                    21

<210> SEQ ID NO 290
<211> LENGTH: 21
<212> TYPE: DNA
<213> ORGANISM: Artificial Sequence
<220> FEATURE:
<223> OTHER INFORMATION: si-TD

<400> SEQUENCE: 290
gguuuuucca aaucucccut t                    21

<210> SEQ ID NO 291
<211> LENGTH: 21
<212> TYPE: DNA
<213> ORGANISM: Artificial Sequence
<220> FEATURE:
<223> OTHER INFORMATION: si-TD

<400> SEQUENCE: 291
gggagauuug gaaaaaccgt t                    21

<210> SEQ ID NO 292
<211> LENGTH: 21
<212> TYPE: DNA
<213> ORGANISM: Artificial Sequence
<220> FEATURE:
<223> OTHER INFORMATION: si-TD

<400> SEQUENCE: 292
cgguuuuucc aaaucuccct t                    21

<210> SEQ ID NO 293
<211> LENGTH: 21
<212> TYPE: DNA
<213> ORGANISM: Artificial Sequence
<220> FEATURE:
<223> OTHER INFORMATION: si-TD

<400> SEQUENCE: 293
ggagauuugg aaaaaccgct t                    21

```
<210> SEQ ID NO 294
<211> LENGTH: 21
<212> TYPE: DNA
<213> ORGANISM: Artificial Sequence
<220> FEATURE:
<223> OTHER INFORMATION: si-TD

<400> SEQUENCE: 294
gcgguuuuuc caaaucucct t                                          21

<210> SEQ ID NO 295
<211> LENGTH: 21
<212> TYPE: DNA
<213> ORGANISM: Artificial Sequence
<220> FEATURE:
<223> OTHER INFORMATION: si-TD

<400> SEQUENCE: 295
gagauuugga aaaccgcut t                                           21

<210> SEQ ID NO 296
<211> LENGTH: 21
<212> TYPE: DNA
<213> ORGANISM: Artificial Sequence
<220> FEATURE:
<223> OTHER INFORMATION: si-TD

<400> SEQUENCE: 296
agcgguuuuu ccaaaucuct t                                          21

<210> SEQ ID NO 297
<211> LENGTH: 21
<212> TYPE: DNA
<213> ORGANISM: Artificial Sequence
<220> FEATURE:
<223> OTHER INFORMATION: si-TD

<400> SEQUENCE: 297
agauuuggaa aaccgcuat t                                           21

<210> SEQ ID NO 298
<211> LENGTH: 21
<212> TYPE: DNA
<213> ORGANISM: Artificial Sequence
<220> FEATURE:
<223> OTHER INFORMATION: si-TD

<400> SEQUENCE: 298
uagcgguuuu uccaaaucut t                                          21

<210> SEQ ID NO 299
<211> LENGTH: 21
<212> TYPE: DNA
<213> ORGANISM: Artificial Sequence
<220> FEATURE:
<223> OTHER INFORMATION: si-TD

<400> SEQUENCE: 299
gauuuggaaa aaccgcuaut t                                          21

<210> SEQ ID NO 300
<211> LENGTH: 21
<212> TYPE: DNA
<213> ORGANISM: Artificial Sequence
<220> FEATURE:
<223> OTHER INFORMATION: si-TD
```

<400> SEQUENCE: 300
auagcgguuu uccaaauct t                                          21

<210> SEQ ID NO 301
<211> LENGTH: 21
<212> TYPE: DNA
<213> ORGANISM: Artificial Sequence
<220> FEATURE:
<223> OTHER INFORMATION: si-TD

<400> SEQUENCE: 301
auuuggaaaa accgcuaugt t                                         21

<210> SEQ ID NO 302
<211> LENGTH: 21
<212> TYPE: DNA
<213> ORGANISM: Artificial Sequence
<220> FEATURE:
<223> OTHER INFORMATION: si-TD

<400> SEQUENCE: 302
cauagcgguu uuccaaaut t                                          21

<210> SEQ ID NO 303
<211> LENGTH: 21
<212> TYPE: DNA
<213> ORGANISM: Artificial Sequence
<220> FEATURE:
<223> OTHER INFORMATION: si-TD

<400> SEQUENCE: 303
uuuggaaaaa ccgcuaugut t                                         21

<210> SEQ ID NO 304
<211> LENGTH: 21
<212> TYPE: DNA
<213> ORGANISM: Artificial Sequence
<220> FEATURE:
<223> OTHER INFORMATION: si-TD

<400> SEQUENCE: 304
acauagcggu uuuccaaat t                                          21

<210> SEQ ID NO 305
<211> LENGTH: 21
<212> TYPE: DNA
<213> ORGANISM: Artificial Sequence
<220> FEATURE:
<223> OTHER INFORMATION: si-TD

<400> SEQUENCE: 305
uuggaaaaac cgcuaugugt t                                         21

<210> SEQ ID NO 306
<211> LENGTH: 21
<212> TYPE: DNA
<213> ORGANISM: Artificial Sequence
<220> FEATURE:
<223> OTHER INFORMATION: si-TD

<400> SEQUENCE: 306
cacauagcgg uuuuccaat t                                          21

```
<210> SEQ ID NO 307
<211> LENGTH: 21
<212> TYPE: DNA
<213> ORGANISM: Artificial Sequence
<220> FEATURE:
<223> OTHER INFORMATION: si-TD

<400> SEQUENCE: 307
uggaaaaacc gcuauguggt t                                            21

<210> SEQ ID NO 308
<211> LENGTH: 21
<212> TYPE: DNA
<213> ORGANISM: Artificial Sequence
<220> FEATURE:
<223> OTHER INFORMATION: si-TD

<400> SEQUENCE: 308
ccacauagcg guuuuuccat t                                            21

<210> SEQ ID NO 309
<211> LENGTH: 21
<212> TYPE: DNA
<213> ORGANISM: Artificial Sequence
<220> FEATURE:
<223> OTHER INFORMATION: si-TD

<400> SEQUENCE: 309
ggaaaaaccg cuaugugggt t                                            21

<210> SEQ ID NO 310
<211> LENGTH: 21
<212> TYPE: DNA
<213> ORGANISM: Artificial Sequence
<220> FEATURE:
<223> OTHER INFORMATION: si-TD

<400> SEQUENCE: 310
accacauagc gguuuuucct t                                            21

<210> SEQ ID NO 311
<211> LENGTH: 21
<212> TYPE: DNA
<213> ORGANISM: Artificial Sequence
<220> FEATURE:
<223> OTHER INFORMATION: si-TD

<400> SEQUENCE: 311
gaaaaaccgc uauguggugt t                                            21

<210> SEQ ID NO 312
<211> LENGTH: 21
<212> TYPE: DNA
<213> ORGANISM: Artificial Sequence
<220> FEATURE:
<223> OTHER INFORMATION: si-TD

<400> SEQUENCE: 312
caccacauag cgguuuuuct t                                            21

<210> SEQ ID NO 313
<211> LENGTH: 21
<212> TYPE: DNA
<213> ORGANISM: Artificial Sequence
<220> FEATURE:
<223> OTHER INFORMATION: si-TD
```

```
<400> SEQUENCE: 313
aaaaaccgcu auguggugct t                                              21

<210> SEQ ID NO 314
<211> LENGTH: 21
<212> TYPE: DNA
<213> ORGANISM: Artificial Sequence
<220> FEATURE:
<223> OTHER INFORMATION: si-TD

<400> SEQUENCE: 314
gcaccacaua gcgguuuuut t                                              21

<210> SEQ ID NO 315
<211> LENGTH: 21
<212> TYPE: DNA
<213> ORGANISM: Artificial Sequence
<220> FEATURE:
<223> OTHER INFORMATION: si-TD

<400> SEQUENCE: 315
aaaaccgcua uguggugcut t                                              21

<210> SEQ ID NO 316
<211> LENGTH: 21
<212> TYPE: DNA
<213> ORGANISM: Artificial Sequence
<220> FEATURE:
<223> OTHER INFORMATION: si-TD

<400> SEQUENCE: 316
agcaccacau agcgguuuut t                                              21

<210> SEQ ID NO 317
<211> LENGTH: 21
<212> TYPE: DNA
<213> ORGANISM: Artificial Sequence
<220> FEATURE:
<223> OTHER INFORMATION: si-TD

<400> SEQUENCE: 317
aaaccgcuau guggugcugt t                                              21

<210> SEQ ID NO 318
<211> LENGTH: 21
<212> TYPE: DNA
<213> ORGANISM: Artificial Sequence
<220> FEATURE:
<223> OTHER INFORMATION: si-TD

<400> SEQUENCE: 318
cagcaccaca uagcgguuut t                                              21

<210> SEQ ID NO 319
<211> LENGTH: 21
<212> TYPE: DNA
<213> ORGANISM: Artificial Sequence
<220> FEATURE:
<223> OTHER INFORMATION: si-TD

<400> SEQUENCE: 319
aaccgcuaug uggugcugat t                                              21
```

-continued

```
<210> SEQ ID NO 320
<211> LENGTH: 21
<212> TYPE: DNA
<213> ORGANISM: Artificial Sequence
<220> FEATURE:
<223> OTHER INFORMATION: si-TD

<400> SEQUENCE: 320
ucagcaccac auagcgguut t                                              21

<210> SEQ ID NO 321
<211> LENGTH: 21
<212> TYPE: DNA
<213> ORGANISM: Artificial Sequence
<220> FEATURE:
<223> OTHER INFORMATION: si-TD

<400> SEQUENCE: 321
ccgcuaugug gugcugaaat t                                              21

<210> SEQ ID NO 322
<211> LENGTH: 21
<212> TYPE: DNA
<213> ORGANISM: Artificial Sequence
<220> FEATURE:
<223> OTHER INFORMATION: si-TD

<400> SEQUENCE: 322
uuucagcacc acauagcggt t                                              21

<210> SEQ ID NO 323
<211> LENGTH: 21
<212> TYPE: DNA
<213> ORGANISM: Artificial Sequence
<220> FEATURE:
<223> OTHER INFORMATION: si-TD

<400> SEQUENCE: 323
cgcuaugugg ugcugaaagt t                                              21

<210> SEQ ID NO 324
<211> LENGTH: 21
<212> TYPE: DNA
<213> ORGANISM: Artificial Sequence
<220> FEATURE:
<223> OTHER INFORMATION: si-TD

<400> SEQUENCE: 324
cuuucagcac cacauagcgt t                                              21

<210> SEQ ID NO 325
<211> LENGTH: 21
<212> TYPE: DNA
<213> ORGANISM: Artificial Sequence
<220> FEATURE:
<223> OTHER INFORMATION: si-TD

<400> SEQUENCE: 325
gcuauguggu gcugaaaggt t                                              21

<210> SEQ ID NO 326
<211> LENGTH: 21
<212> TYPE: DNA
<213> ORGANISM: Artificial Sequence
<220> FEATURE:
<223> OTHER INFORMATION: si-TD
```

<400> SEQUENCE: 326
ccuuucagca ccacauagct t                                               21

<210> SEQ ID NO 327
<211> LENGTH: 21
<212> TYPE: DNA
<213> ORGANISM: Artificial Sequence
<220> FEATURE:
<223> OTHER INFORMATION: si-TD

<400> SEQUENCE: 327
gagaaggagg uaaaagaugt t                                               21

<210> SEQ ID NO 328
<211> LENGTH: 21
<212> TYPE: DNA
<213> ORGANISM: Artificial Sequence
<220> FEATURE:
<223> OTHER INFORMATION: si-TD

<400> SEQUENCE: 328
caucuuuuac cuccuucuct t                                               21

<210> SEQ ID NO 329
<211> LENGTH: 21
<212> TYPE: DNA
<213> ORGANISM: Artificial Sequence
<220> FEATURE:
<223> OTHER INFORMATION: si-TD

<400> SEQUENCE: 329
agaaggaggu aaaagaugat t                                               21

<210> SEQ ID NO 330
<211> LENGTH: 21
<212> TYPE: DNA
<213> ORGANISM: Artificial Sequence
<220> FEATURE:
<223> OTHER INFORMATION: si-TD

<400> SEQUENCE: 330
ucaucuuuua ccuccuucut t                                               21

<210> SEQ ID NO 331
<211> LENGTH: 21
<212> TYPE: DNA
<213> ORGANISM: Artificial Sequence
<220> FEATURE:
<223> OTHER INFORMATION: si-TD

<400> SEQUENCE: 331
gaaggaggua aaagaugagt t                                               21

<210> SEQ ID NO 332
<211> LENGTH: 21
<212> TYPE: DNA
<213> ORGANISM: Artificial Sequence
<220> FEATURE:
<223> OTHER INFORMATION: si-TD

<400> SEQUENCE: 332
cucaucuuuu accuccuuct t                                               21

-continued

```
<210> SEQ ID NO 333
<211> LENGTH: 21
<212> TYPE: DNA
<213> ORGANISM: Artificial Sequence
<220> FEATURE:
<223> OTHER INFORMATION: si-TD

<400> SEQUENCE: 333
aaggagguaa aagaugagat t                                          21

<210> SEQ ID NO 334
<211> LENGTH: 21
<212> TYPE: DNA
<213> ORGANISM: Artificial Sequence
<220> FEATURE:
<223> OTHER INFORMATION: si-TD

<400> SEQUENCE: 334
ucucaucuuu uaccuccuut t                                          21

<210> SEQ ID NO 335
<211> LENGTH: 21
<212> TYPE: DNA
<213> ORGANISM: Artificial Sequence
<220> FEATURE:
<223> OTHER INFORMATION: si-TD

<400> SEQUENCE: 335
aggagguaaa agaugagaat t                                          21

<210> SEQ ID NO 336
<211> LENGTH: 21
<212> TYPE: DNA
<213> ORGANISM: Artificial Sequence
<220> FEATURE:
<223> OTHER INFORMATION: si-TD

<400> SEQUENCE: 336
uucucaucuu uuaccuccut t                                          21

<210> SEQ ID NO 337
<211> LENGTH: 21
<212> TYPE: DNA
<213> ORGANISM: Artificial Sequence
<220> FEATURE:
<223> OTHER INFORMATION: si-TD

<400> SEQUENCE: 337
ggagguaaaa gaugagaaat t                                          21

<210> SEQ ID NO 338
<211> LENGTH: 21
<212> TYPE: DNA
<213> ORGANISM: Artificial Sequence
<220> FEATURE:
<223> OTHER INFORMATION: si-TD

<400> SEQUENCE: 338
uuucucaucu uuuaccucct t                                          21

<210> SEQ ID NO 339
<211> LENGTH: 21
<212> TYPE: DNA
<213> ORGANISM: Artificial Sequence
<220> FEATURE:
<223> OTHER INFORMATION: si-TD
```

<400> SEQUENCE: 339
gagguaaaag augagaaaat t					21

<210> SEQ ID NO 340
<211> LENGTH: 21
<212> TYPE: DNA
<213> ORGANISM: Artificial Sequence
<220> FEATURE:
<223> OTHER INFORMATION: si-TD

<400> SEQUENCE: 340
uuuucucauc uuuuaccuct t					21

<210> SEQ ID NO 341
<211> LENGTH: 21
<212> TYPE: DNA
<213> ORGANISM: Artificial Sequence
<220> FEATURE:
<223> OTHER INFORMATION: si-TD

<400> SEQUENCE: 341
agguaaaaga ugagaaaaat t					21

<210> SEQ ID NO 342
<211> LENGTH: 21
<212> TYPE: DNA
<213> ORGANISM: Artificial Sequence
<220> FEATURE:
<223> OTHER INFORMATION: si-TD

<400> SEQUENCE: 342
uuuuucucau cuuuuaccut t					21

<210> SEQ ID NO 343
<211> LENGTH: 21
<212> TYPE: DNA
<213> ORGANISM: Artificial Sequence
<220> FEATURE:
<223> OTHER INFORMATION: si-TD

<400> SEQUENCE: 343
ugagugacua ugagaagugt t					21

<210> SEQ ID NO 344
<211> LENGTH: 21
<212> TYPE: DNA
<213> ORGANISM: Artificial Sequence
<220> FEATURE:
<223> OTHER INFORMATION: si-TD

<400> SEQUENCE: 344
cacuucucau agucacucat t					21

<210> SEQ ID NO 345
<211> LENGTH: 21
<212> TYPE: DNA
<213> ORGANISM: Artificial Sequence
<220> FEATURE:
<223> OTHER INFORMATION: si-TD

<400> SEQUENCE: 345
cugagugacu augagaagut t					21

<210> SEQ ID NO 346
<211> LENGTH: 21
<212> TYPE: DNA
<213> ORGANISM: Artificial Sequence
<220> FEATURE:
<223> OTHER INFORMATION: si-TD

<400> SEQUENCE: 346
acuucucaua gucacucagt t                                              21

<210> SEQ ID NO 347
<211> LENGTH: 21
<212> TYPE: DNA
<213> ORGANISM: Artificial Sequence
<220> FEATURE:
<223> OTHER INFORMATION: si-TD

<400> SEQUENCE: 347
accugaguga cuaugagaat t                                              21

<210> SEQ ID NO 348
<211> LENGTH: 21
<212> TYPE: DNA
<213> ORGANISM: Artificial Sequence
<220> FEATURE:
<223> OTHER INFORMATION: si-TD

<400> SEQUENCE: 348
uucucauagu cacucaggut t                                              21

<210> SEQ ID NO 349
<211> LENGTH: 21
<212> TYPE: DNA
<213> ORGANISM: Artificial Sequence
<220> FEATURE:
<223> OTHER INFORMATION: si-TD

<400> SEQUENCE: 349
gaccugagug acuaugagat t                                              21

<210> SEQ ID NO 350
<211> LENGTH: 21
<212> TYPE: DNA
<213> ORGANISM: Artificial Sequence
<220> FEATURE:
<223> OTHER INFORMATION: si-TD

<400> SEQUENCE: 350
ucucauaguc acucagguct t                                              21

<210> SEQ ID NO 351
<211> LENGTH: 21
<212> TYPE: DNA
<213> ORGANISM: Artificial Sequence
<220> FEATURE:
<223> OTHER INFORMATION: si-TD

<400> SEQUENCE: 351
ugaccugagu gacuaugagt t                                              21

<210> SEQ ID NO 352
<211> LENGTH: 21
<212> TYPE: DNA
<213> ORGANISM: Artificial Sequence
<220> FEATURE:
<223> OTHER INFORMATION: si-TD

```
<400> SEQUENCE: 352
cucauaguca cucaggucat t                                              21

<210> SEQ ID NO 353
<211> LENGTH: 21
<212> TYPE: DNA
<213> ORGANISM: Artificial Sequence
<220> FEATURE:
<223> OTHER INFORMATION: si-TD

<400> SEQUENCE: 353
uugaccugag ugacuaugat t                                              21

<210> SEQ ID NO 354
<211> LENGTH: 21
<212> TYPE: DNA
<213> ORGANISM: Artificial Sequence
<220> FEATURE:
<223> OTHER INFORMATION: si-TD

<400> SEQUENCE: 354
ucauagucac ucaggucaat t                                              21

<210> SEQ ID NO 355
<211> LENGTH: 21
<212> TYPE: DNA
<213> ORGANISM: Artificial Sequence
<220> FEATURE:
<223> OTHER INFORMATION: si-TD

<400> SEQUENCE: 355
uuugaccuga gugacuaugt t                                              21

<210> SEQ ID NO 356
<211> LENGTH: 21
<212> TYPE: DNA
<213> ORGANISM: Artificial Sequence
<220> FEATURE:
<223> OTHER INFORMATION: si-TD

<400> SEQUENCE: 356
cauagucacu caggucaaat t                                              21

<210> SEQ ID NO 357
<211> LENGTH: 21
<212> TYPE: DNA
<213> ORGANISM: Artificial Sequence
<220> FEATURE:
<223> OTHER INFORMATION: si-TD

<400> SEQUENCE: 357
gcaggagcaa gaaaaaucat t                                              21

<210> SEQ ID NO 358
<211> LENGTH: 21
<212> TYPE: DNA
<213> ORGANISM: Artificial Sequence
<220> FEATURE:
<223> OTHER INFORMATION: si-TD

<400> SEQUENCE: 358
ugauuuuucu ugcuccugct t                                              21
```

```
<210> SEQ ID NO 359
<211> LENGTH: 21
<212> TYPE: DNA
<213> ORGANISM: Artificial Sequence
<220> FEATURE:
<223> OTHER INFORMATION: si-TD

<400> SEQUENCE: 359
agcaggagca agaaaaauct t                                              21

<210> SEQ ID NO 360
<211> LENGTH: 21
<212> TYPE: DNA
<213> ORGANISM: Artificial Sequence
<220> FEATURE:
<223> OTHER INFORMATION: si-TD

<400> SEQUENCE: 360 gauuuucuu gcuccugcut t                                               21

<210> SEQ ID NO 361
<211> LENGTH: 21
<212> TYPE: DNA
<213> ORGANISM: Artificial Sequence
<220> FEATURE:
<223> OTHER INFORMATION: si-TD

<400> SEQUENCE: 361
gagcaggagc aagaaaaaut t                                              21

<210> SEQ ID NO 362
<211> LENGTH: 21
<212> TYPE: DNA
<213> ORGANISM: Artificial Sequence
<220> FEATURE:
<223> OTHER INFORMATION: si-TD

<400> SEQUENCE: 362 auuuucuug cuccugcuct t                                               21

<210> SEQ ID NO 363
<211> LENGTH: 21
<212> TYPE: DNA
<213> ORGANISM: Artificial Sequence
<220> FEATURE:
<223> OTHER INFORMATION: si-TD

<400> SEQUENCE: 363
agagcaggag caagaaaaat t                                              21

<210> SEQ ID NO 364
<211> LENGTH: 21
<212> TYPE: DNA
<213> ORGANISM: Artificial Sequence
<220> FEATURE:
<223> OTHER INFORMATION: si-TD

<400> SEQUENCE: 364 uuuucuugc uccugcucut t                                               21

<210> SEQ ID NO 365
<211> LENGTH: 21
<212> TYPE: DNA
<213> ORGANISM: Artificial Sequence
<220> FEATURE:
<223> OTHER INFORMATION: si-TD
```

<400> SEQUENCE: 365
aagagcagga gcaagaaaat t					21

<210> SEQ ID NO 366
<211> LENGTH: 21
<212> TYPE: DNA
<213> ORGANISM: Artificial Sequence
<220> FEATURE:
<223> OTHER INFORMATION: si-TD

<400> SEQUENCE: 366 uuucuugcu ccugcucuut t					21

<210> SEQ ID NO 367
<211> LENGTH: 21
<212> TYPE: DNA
<213> ORGANISM: Artificial Sequence
<220> FEATURE:
<223> OTHER INFORMATION: si-TD

<400> SEQUENCE: 367
caagagcagg agcaagaaat t					21

<210> SEQ ID NO 368
<211> LENGTH: 21
<212> TYPE: DNA
<213> ORGANISM: Artificial Sequence
<220> FEATURE:
<223> OTHER INFORMATION: si-TD

<400> SEQUENCE: 368
uuucuugcuc cugcucuugt t					21

<210> SEQ ID NO 369
<211> LENGTH: 21
<212> TYPE: DNA
<213> ORGANISM: Artificial Sequence
<220> FEATURE:
<223> OTHER INFORMATION: si-TD

<400> SEQUENCE: 369
ccaagagcag gagcaagaat t					21

<210> SEQ ID NO 370
<211> LENGTH: 21
<212> TYPE: DNA
<213> ORGANISM: Artificial Sequence
<220> FEATURE:
<223> OTHER INFORMATION: si-TD

<400> SEQUENCE: 370
uucuugcucc ugcucuuggt t					21

<210> SEQ ID NO 371
<211> LENGTH: 21
<212> TYPE: DNA
<213> ORGANISM: Artificial Sequence
<220> FEATURE:
<223> OTHER INFORMATION: si-TD

<400> SEQUENCE: 371
uccaagagca ggagcaagat t					21

```
<210> SEQ ID NO 372
<211> LENGTH: 21
<212> TYPE: DNA
<213> ORGANISM: Artificial Sequence
<220> FEATURE:
<223> OTHER INFORMATION: si-TD

<400> SEQUENCE: 372
ucuugcuccu gcucuuggat t                                              21

<210> SEQ ID NO 373
<211> LENGTH: 21
<212> TYPE: DNA
<213> ORGANISM: Artificial Sequence
<220> FEATURE:
<223> OTHER INFORMATION: si-TD

<400> SEQUENCE: 373
aggacagcua ucuugcccat t                                              21

<210> SEQ ID NO 374
<211> LENGTH: 21
<212> TYPE: DNA
<213> ORGANISM: Artificial Sequence
<220> FEATURE:
<223> OTHER INFORMATION: si-TD

<400> SEQUENCE: 374
ugggcaagau agcuguccut t                                              21

<210> SEQ ID NO 375
<211> LENGTH: 21
<212> TYPE: DNA
<213> ORGANISM: Artificial Sequence
<220> FEATURE:
<223> OTHER INFORMATION: si-TD

<400> SEQUENCE: 375
gaggacagcu aucuugccct t                                              21

<210> SEQ ID NO 376
<211> LENGTH: 21
<212> TYPE: DNA
<213> ORGANISM: Artificial Sequence
<220> FEATURE:
<223> OTHER INFORMATION: si-TD

<400> SEQUENCE: 376
gggcaagaua gcuguccuct t                                              21

<210> SEQ ID NO 377
<211> LENGTH: 21
<212> TYPE: DNA
<213> ORGANISM: Artificial Sequence
<220> FEATURE:
<223> OTHER INFORMATION: si-TD

<400> SEQUENCE: 377
ggaggacagc uaucuugcct t                                              21

<210> SEQ ID NO 378
<211> LENGTH: 21
<212> TYPE: DNA
<213> ORGANISM: Artificial Sequence
<220> FEATURE:
<223> OTHER INFORMATION: si-TD
```

```
<400> SEQUENCE: 378
ggcaagauag cuguccucct t                                              21

<210> SEQ ID NO 379
<211> LENGTH: 21
<212> TYPE: DNA
<213> ORGANISM: Artificial Sequence
<220> FEATURE:
<223> OTHER INFORMATION: si-TD

<400> SEQUENCE: 379
aggaggacag cuaucuugct t                                              21

<210> SEQ ID NO 380
<211> LENGTH: 21
<212> TYPE: DNA
<213> ORGANISM: Artificial Sequence
<220> FEATURE:
<223> OTHER INFORMATION: si-TD

<400> SEQUENCE: 380
gcaagauagc uguccuccut t                                              21

<210> SEQ ID NO 381
<211> LENGTH: 21
<212> TYPE: DNA
<213> ORGANISM: Artificial Sequence
<220> FEATURE:
<223> OTHER INFORMATION: si-TD

<400> SEQUENCE: 381
gaggaggaca gcuaucuugt t                                              21

<210> SEQ ID NO 382
<211> LENGTH: 21
<212> TYPE: DNA
<213> ORGANISM: Artificial Sequence
<220> FEATURE:
<223> OTHER INFORMATION: si-TD

<400> SEQUENCE: 382
caagauagcu guccuccuct t                                              21

<210> SEQ ID NO 383
<211> LENGTH: 21
<212> TYPE: DNA
<213> ORGANISM: Artificial Sequence
<220> FEATURE:
<223> OTHER INFORMATION: si-TD

<400> SEQUENCE: 383
ugaggaggac agcuaucuut t                                              21

<210> SEQ ID NO 384
<211> LENGTH: 21
<212> TYPE: DNA
<213> ORGANISM: Artificial Sequence
<220> FEATURE:
<223> OTHER INFORMATION: si-TD

<400> SEQUENCE: 384
aagauagcug uccuccucat t                                              21
```

<210> SEQ ID NO 385
<211> LENGTH: 21
<212> TYPE: DNA
<213> ORGANISM: Artificial Sequence
<220> FEATURE:
<223> OTHER INFORMATION: si-TD

<400> SEQUENCE: 385
uugaggagga cagcuaucut t                                              21

<210> SEQ ID NO 386
<211> LENGTH: 21
<212> TYPE: DNA
<213> ORGANISM: Artificial Sequence
<220> FEATURE:
<223> OTHER INFORMATION: si-TD

<400> SEQUENCE: 386
agauagcugu ccuccucaat t                                              21

<210> SEQ ID NO 387
<211> LENGTH: 21
<212> TYPE: DNA
<213> ORGANISM: Artificial Sequence
<220> FEATURE:
<223> OTHER INFORMATION: si-TD

<400> SEQUENCE: 387
guugaggagg acagcuauct t                                              21

<210> SEQ ID NO 388
<211> LENGTH: 21
<212> TYPE: DNA
<213> ORGANISM: Artificial Sequence
<220> FEATURE:
<223> OTHER INFORMATION: si-TD

<400> SEQUENCE: 388
gauagcuguc cuccucaact t                                              21

<210> SEQ ID NO 389
<211> LENGTH: 21
<212> TYPE: DNA
<213> ORGANISM: Artificial Sequence
<220> FEATURE:
<223> OTHER INFORMATION: si-TD

<400> SEQUENCE: 389
cguugaggag gacagcuaut t                                              21

<210> SEQ ID NO 390
<211> LENGTH: 21
<212> TYPE: DNA
<213> ORGANISM: Artificial Sequence
<220> FEATURE:
<223> OTHER INFORMATION: si-TD

<400> SEQUENCE: 390
auagcugucc uccucaacgt t                                              21

<210> SEQ ID NO 391
<211> LENGTH: 21
<212> TYPE: DNA
<213> ORGANISM: Artificial Sequence
<220> FEATURE:
<223> OTHER INFORMATION: si-TD

<400> SEQUENCE: 391
ccguugagga ggacagcuat t                                              21

<210> SEQ ID NO 392
<211> LENGTH: 21
<212> TYPE: DNA
<213> ORGANISM: Artificial Sequence
<220> FEATURE:
<223> OTHER INFORMATION: si-TD

<400> SEQUENCE: 392
uagcuguccu ccucaacggt t                                              21

<210> SEQ ID NO 393
<211> LENGTH: 21
<212> TYPE: DNA
<213> ORGANISM: Artificial Sequence
<220> FEATURE:
<223> OTHER INFORMATION: si-TD

<400> SEQUENCE: 393
accguugagg aggacagcut t                                              21

<210> SEQ ID NO 394
<211> LENGTH: 21
<212> TYPE: DNA
<213> ORGANISM: Artificial Sequence
<220> FEATURE:
<223> OTHER INFORMATION: si-TD

<400> SEQUENCE: 394
agcuguccuc cucaacggut t                                              21

<210> SEQ ID NO 395
<211> LENGTH: 21
<212> TYPE: DNA
<213> ORGANISM: Artificial Sequence
<220> FEATURE:
<223> OTHER INFORMATION: si-TD

<400> SEQUENCE: 395
caccguugag gaggacagct t                                              21

<210> SEQ ID NO 396
<211> LENGTH: 21
<212> TYPE: DNA
<213> ORGANISM: Artificial Sequence
<220> FEATURE:
<223> OTHER INFORMATION: si-TD

<400> SEQUENCE: 396
gcuguccucc ucaacggugt t                                              21

<210> SEQ ID NO 397
<211> LENGTH: 21
<212> TYPE: DNA
<213> ORGANISM: Artificial Sequence
<220> FEATURE:
<223> OTHER INFORMATION: si-TD

<400> SEQUENCE: 397
ucaccguuga ggaggacagt t                                              21

```
<210> SEQ ID NO 398
<211> LENGTH: 21
<212> TYPE: DNA
<213> ORGANISM: Artificial Sequence
<220> FEATURE:
<223> OTHER INFORMATION: si-TD

<400> SEQUENCE: 398
cuguccuccu caacggugat t                                              21

<210> SEQ ID NO 399
<211> LENGTH: 21
<212> TYPE: DNA
<213> ORGANISM: Artificial Sequence
<220> FEATURE:
<223> OTHER INFORMATION: si-TD

<400> SEQUENCE: 399
gucaccguug aggaggacat t                                              21

<210> SEQ ID NO 400
<211> LENGTH: 21
<212> TYPE: DNA
<213> ORGANISM: Artificial Sequence
<220> FEATURE:
<223> OTHER INFORMATION: si-TD

<400> SEQUENCE: 400
uguccuccuc aacggugact t                                              21

<210> SEQ ID NO 401
<211> LENGTH: 21
<212> TYPE: DNA
<213> ORGANISM: Artificial Sequence
<220> FEATURE:
<223> OTHER INFORMATION: si-TD

<400> SEQUENCE: 401
ggucaccguu gaggaggact t                                              21

<210> SEQ ID NO 402
<211> LENGTH: 21
<212> TYPE: DNA
<213> ORGANISM: Artificial Sequence
<220> FEATURE:
<223> OTHER INFORMATION: si-TD

<400> SEQUENCE: 402
guccuccuca acggugacct t                                              21

<210> SEQ ID NO 403
<211> LENGTH: 21
<212> TYPE: DNA
<213> ORGANISM: Artificial Sequence
<220> FEATURE:
<223> OTHER INFORMATION: si-TD

<400> SEQUENCE: 403
aggucaccgu ugaggaggat t                                              21

<210> SEQ ID NO 404
<211> LENGTH: 21
<212> TYPE: DNA
<213> ORGANISM: Artificial Sequence
<220> FEATURE:
<223> OTHER INFORMATION: si-TD
```

<400> SEQUENCE: 404
uccuccucaa cggugaccut t		21

<210> SEQ ID NO 405
<211> LENGTH: 21
<212> TYPE: DNA
<213> ORGANISM: Artificial Sequence
<220> FEATURE:
<223> OTHER INFORMATION: si-TD

<400> SEQUENCE: 405
gaggucaccg uugaggaggt t		21

<210> SEQ ID NO 406
<211> LENGTH: 21
<212> TYPE: DNA
<213> ORGANISM: Artificial Sequence
<220> FEATURE:
<223> OTHER INFORMATION: si-TD

<400> SEQUENCE: 406
ccuccucaac ggugaccuct t		21

<210> SEQ ID NO 407
<211> LENGTH: 21
<212> TYPE: DNA
<213> ORGANISM: Artificial Sequence
<220> FEATURE:
<223> OTHER INFORMATION: si-TD

<400> SEQUENCE: 407
ugaggucacc guugaggagt t		21

<210> SEQ ID NO 408
<211> LENGTH: 21
<212> TYPE: DNA
<213> ORGANISM: Artificial Sequence
<220> FEATURE:
<223> OTHER INFORMATION: si-TD

<400> SEQUENCE: 408
cuccucaacg gugaccucat t		21

<210> SEQ ID NO 409
<211> LENGTH: 21
<212> TYPE: DNA
<213> ORGANISM: Artificial Sequence
<220> FEATURE:
<223> OTHER INFORMATION: si-TD

<400> SEQUENCE: 409
augaggucac cguugaggat t		21

<210> SEQ ID NO 410
<211> LENGTH: 21
<212> TYPE: DNA
<213> ORGANISM: Artificial Sequence
<220> FEATURE:
<223> OTHER INFORMATION: si-TD

<400> SEQUENCE: 410
uccucaacgg ugaccucaut t		21

```
<210> SEQ ID NO 411
<211> LENGTH: 21
<212> TYPE: DNA
<213> ORGANISM: Artificial Sequence
<220> FEATURE:
<223> OTHER INFORMATION: si-TD

<400> SEQUENCE: 411
gaugagguca ccguugaggt t                                              21

<210> SEQ ID NO 412
<211> LENGTH: 21
<212> TYPE: DNA
<213> ORGANISM: Artificial Sequence
<220> FEATURE:
<223> OTHER INFORMATION: si-TD

<400> SEQUENCE: 412
ccucaacggu gaccucauct t                                              21

<210> SEQ ID NO 413
<211> LENGTH: 21
<212> TYPE: DNA
<213> ORGANISM: Artificial Sequence
<220> FEATURE:
<223> OTHER INFORMATION: si-TD

<400> SEQUENCE: 413
uggaugaggu caccguugat t                                              21

<210> SEQ ID NO 414
<211> LENGTH: 21
<212> TYPE: DNA
<213> ORGANISM: Artificial Sequence
<220> FEATURE:
<223> OTHER INFORMATION: si-TD

<400> SEQUENCE: 414
ucaacgguga ccucauccat t                                              21

<210> SEQ ID NO 415
<211> LENGTH: 21
<212> TYPE: DNA
<213> ORGANISM: Artificial Sequence
<220> FEATURE:
<223> OTHER INFORMATION: si-TD

<400> SEQUENCE: 415
uuggaugagg ucaccguugt t                                              21

<210> SEQ ID NO 416
<211> LENGTH: 21
<212> TYPE: DNA
<213> ORGANISM: Artificial Sequence
<220> FEATURE:
<223> OTHER INFORMATION: si-TD

<400> SEQUENCE: 416
caacggugac cucauccaat t                                              21

<210> SEQ ID NO 417
<211> LENGTH: 21
<212> TYPE: DNA
<213> ORGANISM: Artificial Sequence
<220> FEATURE:
<223> OTHER INFORMATION: si-TD
```

<400> SEQUENCE: 417
cuuggaugag gucaccguut t            21

<210> SEQ ID NO 418
<211> LENGTH: 21
<212> TYPE: DNA
<213> ORGANISM: Artificial Sequence
<220> FEATURE:
<223> OTHER INFORMATION: si-TD

<400> SEQUENCE: 418
aacggugacc ucauccaagt t            21

<210> SEQ ID NO 419
<211> LENGTH: 21
<212> TYPE: DNA
<213> ORGANISM: Artificial Sequence
<220> FEATURE:
<223> OTHER INFORMATION: si-TD

<400> SEQUENCE: 419
ucuuggauga ggucaccgut t            21

<210> SEQ ID NO 420
<211> LENGTH: 21
<212> TYPE: DNA
<213> ORGANISM: Artificial Sequence
<220> FEATURE:
<223> OTHER INFORMATION: si-TD

<400> SEQUENCE: 420
acggugaccu cauccaagat t            21

<210> SEQ ID NO 421
<211> LENGTH: 21
<212> TYPE: DNA
<213> ORGANISM: Artificial Sequence
<220> FEATURE:
<223> OTHER INFORMATION: si-TD

<400> SEQUENCE: 421
aucuuggaug aggucaccgt t            21

<210> SEQ ID NO 422
<211> LENGTH: 21
<212> TYPE: DNA
<213> ORGANISM: Artificial Sequence
<220> FEATURE:
<223> OTHER INFORMATION: si-TD

<400> SEQUENCE: 422
cggugaccuc auccaagaut t            21

<210> SEQ ID NO 423
<211> LENGTH: 21
<212> TYPE: DNA
<213> ORGANISM: Artificial Sequence
<220> FEATURE:
<223> OTHER INFORMATION: si-TD

<400> SEQUENCE: 423
uaucuuggau gaggucacct t            21

```
<210> SEQ ID NO 424
<211> LENGTH: 21
<212> TYPE: DNA
<213> ORGANISM: Artificial Sequence
<220> FEATURE:
<223> OTHER INFORMATION: si-TD

<400> SEQUENCE: 424
ggugaccuca uccaagauat t                                      21

<210> SEQ ID NO 425
<211> LENGTH: 21
<212> TYPE: DNA
<213> ORGANISM: Artificial Sequence
<220> FEATURE:
<223> OTHER INFORMATION: si-TD

<400> SEQUENCE: 425
guaucuugga ugaggucact t                                      21

<210> SEQ ID NO 426
<211> LENGTH: 21
<212> TYPE: DNA
<213> ORGANISM: Artificial Sequence
<220> FEATURE:
<223> OTHER INFORMATION: si-TD

<400> SEQUENCE: 426
gugaccucau ccaagauact t                                      21

<210> SEQ ID NO 427
<211> LENGTH: 21
<212> TYPE: DNA
<213> ORGANISM: Artificial Sequence
<220> FEATURE:
<223> OTHER INFORMATION: si-TD

<400> SEQUENCE: 427
cguaucuugg augaggucat t                                      21

<210> SEQ ID NO 428
<211> LENGTH: 21
<212> TYPE: DNA
<213> ORGANISM: Artificial Sequence
<220> FEATURE:
<223> OTHER INFORMATION: si-TD

<400> SEQUENCE: 428
ugaccucauc caagauacgt t                                      21

<210> SEQ ID NO 429
<211> LENGTH: 21
<212> TYPE: DNA
<213> ORGANISM: Artificial Sequence
<220> FEATURE:
<223> OTHER INFORMATION: si-TD

<400> SEQUENCE: 429
ccguaucuug gaugagguct t                                      21

<210> SEQ ID NO 430
<211> LENGTH: 21
<212> TYPE: DNA
<213> ORGANISM: Artificial Sequence
<220> FEATURE:
<223> OTHER INFORMATION: si-TD
```

```
<400> SEQUENCE: 430
gaccucaucc aagauacggt t                                              21

<210> SEQ ID NO 431
<211> LENGTH: 21
<212> TYPE: DNA
<213> ORGANISM: Artificial Sequence
<220> FEATURE:
<223> OTHER INFORMATION: si-TD

<400> SEQUENCE: 431
accguaucuu ggaugaggut t                                              21

<210> SEQ ID NO 432
<211> LENGTH: 21
<212> TYPE: DNA
<213> ORGANISM: Artificial Sequence
<220> FEATURE:
<223> OTHER INFORMATION: si-TD

<400> SEQUENCE: 432
accucaucca agauacgguu t                                              21

<210> SEQ ID NO 433
<211> LENGTH: 21
<212> TYPE: DNA
<213> ORGANISM: Artificial Sequence
<220> FEATURE:
<223> OTHER INFORMATION: si-TD

<400> SEQUENCE: 433
aaccguaucu uggaugaggt t                                              21

<210> SEQ ID NO 434
<211> LENGTH: 21
<212> TYPE: DNA
<213> ORGANISM: Artificial Sequence
<220> FEATURE:
<223> OTHER INFORMATION: si-TD

<400> SEQUENCE: 434
ccucauccaa gauacgguut t                                              21

<210> SEQ ID NO 435
<211> LENGTH: 21
<212> TYPE: DNA
<213> ORGANISM: Artificial Sequence
<220> FEATURE:
<223> OTHER INFORMATION: si-TD

<400> SEQUENCE: 435
aagacccuuc cccugaggat t                                              21

<210> SEQ ID NO 436
<211> LENGTH: 21
<212> TYPE: DNA
<213> ORGANISM: Artificial Sequence
<220> FEATURE:
<223> OTHER INFORMATION: si-TD

<400> SEQUENCE: 436
uccucagggg aagggucuut t                                              21
```

```
<210> SEQ ID NO 437
<211> LENGTH: 21
<212> TYPE: DNA
<213> ORGANISM: Artificial Sequence
<220> FEATURE:
<223> OTHER INFORMATION: si-TD

<400> SEQUENCE: 437
gaagacccuu ccccugaggt t                                              21

<210> SEQ ID NO 438
<211> LENGTH: 21
<212> TYPE: DNA
<213> ORGANISM: Artificial Sequence
<220> FEATURE:
<223> OTHER INFORMATION: si-TD

<400> SEQUENCE: 438
ccucagggga agguucuuct t                                              21

<210> SEQ ID NO 439
<211> LENGTH: 21
<212> TYPE: DNA
<213> ORGANISM: Artificial Sequence
<220> FEATURE:
<223> OTHER INFORMATION: si-TD

<400> SEQUENCE: 439
ggaagacccu uccccugagt t                                              21

<210> SEQ ID NO 440
<211> LENGTH: 21
<212> TYPE: DNA
<213> ORGANISM: Artificial Sequence
<220> FEATURE:
<223> OTHER INFORMATION: si-TD

<400> SEQUENCE: 440 cucagggaa gggucuuucct t                                              21

<210> SEQ ID NO 441
<211> LENGTH: 21
<212> TYPE: DNA
<213> ORGANISM: Artificial Sequence
<220> FEATURE:
<223> OTHER INFORMATION: si-TD

<400> SEQUENCE: 441
aggaagaccc uuccccugat t                                              21

<210> SEQ ID NO 442
<211> LENGTH: 21
<212> TYPE: DNA
<213> ORGANISM: Artificial Sequence
<220> FEATURE:
<223> OTHER INFORMATION: si-TD

<400> SEQUENCE: 442
ucaggggaag ggucuuccut t                                              21

<210> SEQ ID NO 443
<211> LENGTH: 21
<212> TYPE: DNA
<213> ORGANISM: Artificial Sequence
<220> FEATURE:
<223> OTHER INFORMATION: si-TD
```

```
<400> SEQUENCE: 443
gaggaagacc cuuccccugt t                                              21

<210> SEQ ID NO 444
<211> LENGTH: 21
<212> TYPE: DNA
<213> ORGANISM: Artificial Sequence
<220> FEATURE:
<223> OTHER INFORMATION: si-TD

<400> SEQUENCE: 444
caggggaagg gucuuccuct t                                              21

<210> SEQ ID NO 445
<211> LENGTH: 21
<212> TYPE: DNA
<213> ORGANISM: Artificial Sequence
<220> FEATURE:
<223> OTHER INFORMATION: si-TD

<400> SEQUENCE: 445
agaggaagac ccuucccout t                                              21

<210> SEQ ID NO 446
<211> LENGTH: 21
<212> TYPE: DNA
<213> ORGANISM: Artificial Sequence
<220> FEATURE:
<223> OTHER INFORMATION: si-TD

<400> SEQUENCE: 446
agggaagggg ucuuccucut t                                              21

<210> SEQ ID NO 447
<211> LENGTH: 21
<212> TYPE: DNA
<213> ORGANISM: Artificial Sequence
<220> FEATURE:
<223> OTHER INFORMATION: si-TD

<400> SEQUENCE: 447
aagaggaaga cccuuccect t                                              21

<210> SEQ ID NO 448
<211> LENGTH: 21
<212> TYPE: DNA
<213> ORGANISM: Artificial Sequence
<220> FEATURE:
<223> OTHER INFORMATION: si-TD

<400> SEQUENCE: 448
ggggaagggu cuuccucuut t                                              21

<210> SEQ ID NO 449
<211> LENGTH: 21
<212> TYPE: DNA
<213> ORGANISM: Artificial Sequence
<220> FEATURE:
<223> OTHER INFORMATION: si-TD

<400> SEQUENCE: 449
caagaggaag acccuucccut t                                             21
```

```
<210> SEQ ID NO 450
<211> LENGTH: 21
<212> TYPE: DNA
<213> ORGANISM: Artificial Sequence
<220> FEATURE:
<223> OTHER INFORMATION: si-TD

<400> SEQUENCE: 450
gggaaggguc uuccucuugt t                                              21

<210> SEQ ID NO 451
<211> LENGTH: 21
<212> TYPE: DNA
<213> ORGANISM: Artificial Sequence
<220> FEATURE:
<223> OTHER INFORMATION: si-TD

<400> SEQUENCE: 451
ccaagaggaa gacccuucct t                                              21

<210> SEQ ID NO 452
<211> LENGTH: 21
<212> TYPE: DNA
<213> ORGANISM: Artificial Sequence
<220> FEATURE:
<223> OTHER INFORMATION: si-TD

<400> SEQUENCE: 452
ggaagggucu uccucuuggt t                                              21

<210> SEQ ID NO 453
<211> LENGTH: 21
<212> TYPE: DNA
<213> ORGANISM: Artificial Sequence
<220> FEATURE:
<223> OTHER INFORMATION: si-TD

<400> SEQUENCE: 453
uccaagagga agacccuuct t                                              21

<210> SEQ ID NO 454
<211> LENGTH: 21
<212> TYPE: DNA
<213> ORGANISM: Artificial Sequence
<220> FEATURE:
<223> OTHER INFORMATION: si-TD

<400> SEQUENCE: 454 gaaggguucuu ccucuuggat t                                             21

<210> SEQ ID NO 455
<211> LENGTH: 21
<212> TYPE: DNA
<213> ORGANISM: Artificial Sequence
<220> FEATURE:
<223> OTHER INFORMATION: si-TD

<400> SEQUENCE: 455
auccaagagg aagacccuut t                                              21

<210> SEQ ID NO 456
<211> LENGTH: 21
<212> TYPE: DNA
<213> ORGANISM: Artificial Sequence
<220> FEATURE:
<223> OTHER INFORMATION: si-TD
```

<400> SEQUENCE: 456
aagggucuuc cucuuggaut t        21

<210> SEQ ID NO 457
<211> LENGTH: 21
<212> TYPE: DNA
<213> ORGANISM: Artificial Sequence
<220> FEATURE:
<223> OTHER INFORMATION: si-TD

<400> SEQUENCE: 457
gauccaagag gaagacccut t        21

<210> SEQ ID NO 458
<211> LENGTH: 21
<212> TYPE: DNA
<213> ORGANISM: Artificial Sequence
<220> FEATURE:
<223> OTHER INFORMATION: si-TD

<400> SEQUENCE: 458
agggucuucc ucuuggauct t        21

<210> SEQ ID NO 459
<211> LENGTH: 21
<212> TYPE: DNA
<213> ORGANISM: Artificial Sequence
<220> FEATURE:
<223> OTHER INFORMATION: si-TD

<400> SEQUENCE: 459
ugauccaaga ggaagaccct t        21

<210> SEQ ID NO 460
<211> LENGTH: 21
<212> TYPE: DNA
<213> ORGANISM: Artificial Sequence
<220> FEATURE:
<223> OTHER INFORMATION: si-TD

<400> SEQUENCE: 460
gggucuuccu cuuggaucat t        21

<210> SEQ ID NO 461
<211> LENGTH: 21
<212> TYPE: DNA
<213> ORGANISM: Artificial Sequence
<220> FEATURE:
<223> OTHER INFORMATION: si-TD

<400> SEQUENCE: 461
ggacaagucu guggcccagt t        21

<210> SEQ ID NO 462
<211> LENGTH: 21
<212> TYPE: DNA
<213> ORGANISM: Artificial Sequence
<220> FEATURE:
<223> OTHER INFORMATION: si-TD

<400> SEQUENCE: 462
cugggccaca gacuugucct t        21

```
<210> SEQ ID NO 463
<211> LENGTH: 21
<212> TYPE: DNA
<213> ORGANISM: Artificial Sequence
<220> FEATURE:
<223> OTHER INFORMATION: si-TD

<400> SEQUENCE: 463
uggacaaguc uguggcccat t                                              21

<210> SEQ ID NO 464
<211> LENGTH: 21
<212> TYPE: DNA
<213> ORGANISM: Artificial Sequence
<220> FEATURE:
<223> OTHER INFORMATION: si-TD

<400> SEQUENCE: 464
ugggccacag acuuguccat t                                              21

<210> SEQ ID NO 465
<211> LENGTH: 21
<212> TYPE: DNA
<213> ORGANISM: Artificial Sequence
<220> FEATURE:
<223> OTHER INFORMATION: si-TD

<400> SEQUENCE: 465
cuggacaagu cuguggccct t                                              21

<210> SEQ ID NO 466
<211> LENGTH: 21
<212> TYPE: DNA
<213> ORGANISM: Artificial Sequence
<220> FEATURE:
<223> OTHER INFORMATION: si-TD

<400> SEQUENCE: 466
gggccacaga cuuguccagt t                                              21

<210> SEQ ID NO 467
<211> LENGTH: 21
<212> TYPE: DNA
<213> ORGANISM: Artificial Sequence
<220> FEATURE:
<223> OTHER INFORMATION: si-TD

<400> SEQUENCE: 467
gccucccugg aggagaucct t                                              21

<210> SEQ ID NO 468
<211> LENGTH: 21
<212> TYPE: DNA
<213> ORGANISM: Artificial Sequence
<220> FEATURE:
<223> OTHER INFORMATION: si-TD

<400> SEQUENCE: 468
ggaucuccuc cagggaggct t                                              21

<210> SEQ ID NO 469
<211> LENGTH: 21
<212> TYPE: DNA
<213> ORGANISM: Artificial Sequence
<220> FEATURE:
<223> OTHER INFORMATION: si-TD
```

```
<400> SEQUENCE: 469
ccucccugga ggagauccut t                                              21

<210> SEQ ID NO 470
<211> LENGTH: 21
<212> TYPE: DNA
<213> ORGANISM: Artificial Sequence
<220> FEATURE:
<223> OTHER INFORMATION: si-TD

<400> SEQUENCE: 470
aggaucuccu ccagggaggt t                                              21

<210> SEQ ID NO 471
<211> LENGTH: 21
<212> TYPE: DNA
<213> ORGANISM: Artificial Sequence
<220> FEATURE:
<223> OTHER INFORMATION: si-TD

<400> SEQUENCE: 471
gguagcaagg aaacuggagt t                                              21

<210> SEQ ID NO 472
<211> LENGTH: 21
<212> TYPE: DNA
<213> ORGANISM: Artificial Sequence
<220> FEATURE:
<223> OTHER INFORMATION: si-TD

<400> SEQUENCE: 472
cuccaguuuc cuugcuacct t                                              21

<210> SEQ ID NO 473
<211> LENGTH: 21
<212> TYPE: DNA
<213> ORGANISM: Artificial Sequence
<220> FEATURE:
<223> OTHER INFORMATION: si-TD

<400> SEQUENCE: 473
ugguagcaag gaaacuggat t                                              21

<210> SEQ ID NO 474
<211> LENGTH: 21
<212> TYPE: DNA
<213> ORGANISM: Artificial Sequence
<220> FEATURE:
<223> OTHER INFORMATION: si-TD

<400> SEQUENCE: 474
uccaguuucc uugcuaccat t                                              21

<210> SEQ ID NO 475
<211> LENGTH: 21
<212> TYPE: DNA
<213> ORGANISM: Artificial Sequence
<220> FEATURE:
<223> OTHER INFORMATION: si-TD

<400> SEQUENCE: 475
cugguagcaa ggaaacuggt t                                              21
```

```
<210> SEQ ID NO 476
<211> LENGTH: 21
<212> TYPE: DNA
<213> ORGANISM: Artificial Sequence
<220> FEATURE:
<223> OTHER INFORMATION: si-TD

<400> SEQUENCE: 476
ccaguuuccu ugcuaccagt t                                              21

<210> SEQ ID NO 477
<211> LENGTH: 21
<212> TYPE: DNA
<213> ORGANISM: Artificial Sequence
<220> FEATURE:
<223> OTHER INFORMATION: si-TD607

<400> SEQUENCE: 477
ccugguagca aggaaacugt t                                              21

<210> SEQ ID NO 478
<211> LENGTH: 21
<212> TYPE: DNA
<213> ORGANISM: Artificial Sequence
<220> FEATURE:
<223> OTHER INFORMATION: si-TD607

<400> SEQUENCE: 478
caguuuccuu gcuaccaggt t                                              21

<210> SEQ ID NO 479
<211> LENGTH: 21
<212> TYPE: DNA
<213> ORGANISM: Artificial Sequence
<220> FEATURE:
<223> OTHER INFORMATION: si-TD606

<400> SEQUENCE: 479
accugguagc aaggaaacut t                                              21

<210> SEQ ID NO 480
<211> LENGTH: 21
<212> TYPE: DNA
<213> ORGANISM: Artificial Sequence
<220> FEATURE:
<223> OTHER INFORMATION: si-TD606

<400> SEQUENCE: 480
aguuuccuug cuaccaggut t                                              21

<210> SEQ ID NO 481
<211> LENGTH: 21
<212> TYPE: DNA
<213> ORGANISM: Artificial Sequence
<220> FEATURE:
<223> OTHER INFORMATION: si-TD605

<400> SEQUENCE: 481
gaccugguag caaggaaact t                                              21

<210> SEQ ID NO 482
<211> LENGTH: 21
<212> TYPE: DNA
<213> ORGANISM: Artificial Sequence
<220> FEATURE:
<223> OTHER INFORMATION: si-TD605
```

<400> SEQUENCE: 482
guuuccuugc uaccagguct t                                              21

<210> SEQ ID NO 483
<211> LENGTH: 21
<212> TYPE: DNA
<213> ORGANISM: Artificial Sequence
<220> FEATURE:
<223> OTHER INFORMATION: si-TD604

<400> SEQUENCE: 483
aggaccuggu agcaaggaat t                                              21

<210> SEQ ID NO 484
<211> LENGTH: 21
<212> TYPE: DNA
<213> ORGANISM: Artificial Sequence
<220> FEATURE:
<223> OTHER INFORMATION: si-TD604

<400> SEQUENCE: 484
uuccuugcua ccagguccut t                                              21

<210> SEQ ID NO 485
<211> LENGTH: 21
<212> TYPE: DNA
<213> ORGANISM: Artificial Sequence
<220> FEATURE:
<223> OTHER INFORMATION: si-TD603

<400> SEQUENCE: 485
caggaccugg uagcaaggat t                                              21

<210> SEQ ID NO 486
<211> LENGTH: 21
<212> TYPE: DNA
<213> ORGANISM: Artificial Sequence
<220> FEATURE:
<223> OTHER INFORMATION: si-TD603

<400> SEQUENCE: 486
uccuugcuac cagguccugt t                                              21

<210> SEQ ID NO 487
<211> LENGTH: 21
<212> TYPE: DNA
<213> ORGANISM: Artificial Sequence
<220> FEATURE:
<223> OTHER INFORMATION: si-TD602

<400> SEQUENCE: 487
ccaggaccug guagcaaggt t                                              21

<210> SEQ ID NO 488
<211> LENGTH: 21
<212> TYPE: DNA
<213> ORGANISM: Artificial Sequence
<220> FEATURE:
<223> OTHER INFORMATION: si-TD602

<400> SEQUENCE: 488
ccuugcuacc agguccuggt t                                              21

```
<210> SEQ ID NO 489
<211> LENGTH: 21
<212> TYPE: DNA
<213> ORGANISM: Artificial Sequence
<220> FEATURE:
<223> OTHER INFORMATION: si-TD601

<400> SEQUENCE: 489
uccaggaccu gguagcaagt t                                              21

<210> SEQ ID NO 490
<211> LENGTH: 21
<212> TYPE: DNA
<213> ORGANISM: Artificial Sequence
<220> FEATURE:
<223> OTHER INFORMATION: si-TD601

<400> SEQUENCE: 490
cuugcuacca gguccuggat t                                              21

<210> SEQ ID NO 491
<211> LENGTH: 21
<212> TYPE: DNA
<213> ORGANISM: Artificial Sequence
<220> FEATURE:
<223> OTHER INFORMATION: si-TD600

<400> SEQUENCE: 491
auccaggacc ugguagcaat t                                              21

<210> SEQ ID NO 492
<211> LENGTH: 21
<212> TYPE: DNA
<213> ORGANISM: Artificial Sequence
<220> FEATURE:
<223> OTHER INFORMATION: si-TD600

<400> SEQUENCE: 492
uugcuaccag guccuggaut t                                              21

<210> SEQ ID NO 493
<211> LENGTH: 21
<212> TYPE: DNA
<213> ORGANISM: Artificial Sequence
<220> FEATURE:
<223> OTHER INFORMATION: si-TD599

<400> SEQUENCE: 493
gauccaggac cugguagcat t                                              21

<210> SEQ ID NO 494
<211> LENGTH: 21
<212> TYPE: DNA
<213> ORGANISM: Artificial Sequence
<220> FEATURE:
<223> OTHER INFORMATION: si-TD599

<400> SEQUENCE: 494
ugcuaccagg uccuggauct t                                              21

<210> SEQ ID NO 495
<211> LENGTH: 21
<212> TYPE: DNA
<213> ORGANISM: Artificial Sequence
<220> FEATURE:
<223> OTHER INFORMATION: si-TD598
```

```
<400> SEQUENCE: 495
ggauccagga ccugguagct t                                              21

<210> SEQ ID NO 496
<211> LENGTH: 21
<212> TYPE: DNA
<213> ORGANISM: Artificial Sequence
<220> FEATURE:
<223> OTHER INFORMATION: si-TD598

<400> SEQUENCE: 496
gcuaccaggu ccuggaucct t                                              21

<210> SEQ ID NO 497
<211> LENGTH: 21
<212> TYPE: DNA
<213> ORGANISM: Artificial Sequence
<220> FEATURE:
<223> OTHER INFORMATION: si-TD597

<400> SEQUENCE: 497
cggauccagg accugguagt t                                              21

<210> SEQ ID NO 498
<211> LENGTH: 21
<212> TYPE: DNA
<213> ORGANISM: Artificial Sequence
<220> FEATURE:
<223> OTHER INFORMATION: si-TD597

<400> SEQUENCE: 498
cuaccagguc cuggauccgt t                                              21

<210> SEQ ID NO 499
<211> LENGTH: 21
<212> TYPE: DNA
<213> ORGANISM: Artificial Sequence
<220> FEATURE:
<223> OTHER INFORMATION: si-TD596

<400> SEQUENCE: 499
ccggauccag gaccugguat t                                              21

<210> SEQ ID NO 500
<211> LENGTH: 21
<212> TYPE: DNA
<213> ORGANISM: Artificial Sequence
<220> FEATURE:
<223> OTHER INFORMATION: si-TD596

<400> SEQUENCE: 500
uaccaggucc uggauccggt t                                              21

<210> SEQ ID NO 501
<211> LENGTH: 21
<212> TYPE: DNA
<213> ORGANISM: Artificial Sequence
<220> FEATURE:
<223> OTHER INFORMATION: si-TD595

<400> SEQUENCE: 501
cccggaucca ggaccuggut t                                              21
```

```
<210> SEQ ID NO 502
<211> LENGTH: 21
<212> TYPE: DNA
<213> ORGANISM: Artificial Sequence
<220> FEATURE:
<223> OTHER INFORMATION: si-TD595

<400> SEQUENCE: 502
accagguccu ggauccgggt t                                              21

<210> SEQ ID NO 503
<211> LENGTH: 21
<212> TYPE: DNA
<213> ORGANISM: Artificial Sequence
<220> FEATURE:
<223> OTHER INFORMATION: si-TD594

<400> SEQUENCE: 503
ucccggaucc aggaccuggt t                                              21

<210> SEQ ID NO 504
<211> LENGTH: 21
<212> TYPE: DNA
<213> ORGANISM: Artificial Sequence
<220> FEATURE:
<223> OTHER INFORMATION: si-TD594

<400> SEQUENCE: 504
ccagguccug gauccgggat t                                              21

<210> SEQ ID NO 505
<211> LENGTH: 21
<212> TYPE: DNA
<213> ORGANISM: Artificial Sequence
<220> FEATURE:
<223> OTHER INFORMATION: si-TD593

<400> SEQUENCE: 505
gucccggauc caggaccugt t                                              21

<210> SEQ ID NO 506
<211> LENGTH: 21
<212> TYPE: DNA
<213> ORGANISM: Artificial Sequence
<220> FEATURE:
<223> OTHER INFORMATION: si-TD593

<400> SEQUENCE: 506
cagguccugg auccgggact t                                              21

<210> SEQ ID NO 507
<211> LENGTH: 21
<212> TYPE: DNA
<213> ORGANISM: Artificial Sequence
<220> FEATURE:
<223> OTHER INFORMATION: si-TD592

<400> SEQUENCE: 507
ugucccggau ccaggaccut t                                              21

<210> SEQ ID NO 508
<211> LENGTH: 21
<212> TYPE: DNA
<213> ORGANISM: Artificial Sequence
<220> FEATURE:
<223> OTHER INFORMATION: si-TD592
```

<400> SEQUENCE: 508
agguccugga uccgggacat t                                              21

<210> SEQ ID NO 509
<211> LENGTH: 21
<212> TYPE: DNA
<213> ORGANISM: Artificial Sequence
<220> FEATURE:
<223> OTHER INFORMATION: si-TD591

<400> SEQUENCE: 509
cugucccgga uccaggacct t                                              21

<210> SEQ ID NO 510
<211> LENGTH: 21
<212> TYPE: DNA
<213> ORGANISM: Artificial Sequence
<220> FEATURE:
<223> OTHER INFORMATION: si-TD591

<400> SEQUENCE: 510
gguccuggau ccgggacagt t                                              21

<210> SEQ ID NO 511
<211> LENGTH: 21
<212> TYPE: DNA
<213> ORGANISM: Artificial Sequence
<220> FEATURE:
<223> OTHER INFORMATION: si-TD590

<400> SEQUENCE: 511
gcugucccgg auccaggact t                                              21

<210> SEQ ID NO 512
<211> LENGTH: 21
<212> TYPE: DNA
<213> ORGANISM: Artificial Sequence
<220> FEATURE:
<223> OTHER INFORMATION: si-TD590

<400> SEQUENCE: 512
guccuggauc cgggacagct t                                              21

<210> SEQ ID NO 513
<211> LENGTH: 21
<212> TYPE: DNA
<213> ORGANISM: Artificial Sequence
<220> FEATURE:
<223> OTHER INFORMATION: si-TD589

<400> SEQUENCE: 513
agcugucccg gauccaggat t                                              21

<210> SEQ ID NO 514
<211> LENGTH: 21
<212> TYPE: DNA
<213> ORGANISM: Artificial Sequence
<220> FEATURE:
<223> OTHER INFORMATION: si-TD589

<400> SEQUENCE: 514
uccuggaucc gggacagcut t                                              21

```
<210> SEQ ID NO 515
<211> LENGTH: 21
<212> TYPE: DNA
<213> ORGANISM: Artificial Sequence
<220> FEATURE:
<223> OTHER INFORMATION: si-TD588

<400> SEQUENCE: 515
cagcuguccc ggauccaggt t                                              21

<210> SEQ ID NO 516
<211> LENGTH: 21
<212> TYPE: DNA
<213> ORGANISM: Artificial Sequence
<220> FEATURE:
<223> OTHER INFORMATION: si-TD588

<400> SEQUENCE: 516
ccuggauccg ggacagcugt t                                              21

<210> SEQ ID NO 517
<211> LENGTH: 21
<212> TYPE: DNA
<213> ORGANISM: Artificial Sequence
<220> FEATURE:
<223> OTHER INFORMATION: si-TD587

<400> SEQUENCE: 517
gcagcugucc cggauccagt t                                              21

<210> SEQ ID NO 518
<211> LENGTH: 21
<212> TYPE: DNA
<213> ORGANISM: Artificial Sequence
<220> FEATURE:
<223> OTHER INFORMATION: si-TD587

<400> SEQUENCE: 518
cuggauccgg gacagcugct t                                              21

<210> SEQ ID NO 519
<211> LENGTH: 21
<212> TYPE: DNA
<213> ORGANISM: Artificial Sequence
<220> FEATURE:
<223> OTHER INFORMATION: si-TD586

<400> SEQUENCE: 519
ggcagcuguc ccggauccat t                                              21

<210> SEQ ID NO 520
<211> LENGTH: 21
<212> TYPE: DNA
<213> ORGANISM: Artificial Sequence
<220> FEATURE:
<223> OTHER INFORMATION: si-TD586

<400> SEQUENCE: 520
uggauccggg acagcugcct t                                              21

<210> SEQ ID NO 521
<211> LENGTH: 21
<212> TYPE: DNA
<213> ORGANISM: Artificial Sequence
<220> FEATURE:
<223> OTHER INFORMATION: si-TD585
```

<400> SEQUENCE: 521
gggcagcugu cccggauccu t                    21

<210> SEQ ID NO 522
<211> LENGTH: 21
<212> TYPE: DNA
<213> ORGANISM: Artificial Sequence
<220> FEATURE:
<223> OTHER INFORMATION: si-TD585

<400> SEQUENCE: 522
ggauccggga cagcugccct t                    21

<210> SEQ ID NO 523
<211> LENGTH: 21
<212> TYPE: DNA
<213> ORGANISM: Artificial Sequence
<220> FEATURE:
<223> OTHER INFORMATION: si-TD721

<400> SEQUENCE: 523
agcugagaga ccuguacagt t                    21

<210> SEQ ID NO 524
<211> LENGTH: 21
<212> TYPE: DNA
<213> ORGANISM: Artificial Sequence
<220> FEATURE:
<223> OTHER INFORMATION: si-TD721

<400> SEQUENCE: 524
cuguacaggu cucucagcut t                    21

<210> SEQ ID NO 525
<211> LENGTH: 21
<212> TYPE: DNA
<213> ORGANISM: Artificial Sequence
<220> FEATURE:
<223> OTHER INFORMATION: si-TD720

<400> SEQUENCE: 525
gagcugagag accuguacat t                    21

<210> SEQ ID NO 526
<211> LENGTH: 21
<212> TYPE: DNA
<213> ORGANISM: Artificial Sequence
<220> FEATURE:
<223> OTHER INFORMATION: si-TD720

<400> SEQUENCE: 526
uguacagguc ucucagcuct t                    21

<210> SEQ ID NO 527
<211> LENGTH: 21
<212> TYPE: DNA
<213> ORGANISM: Artificial Sequence
<220> FEATURE:
<223> OTHER INFORMATION: si-TD719

<400> SEQUENCE: 527
ggagcugaga gaccuguact t                    21

```
<210> SEQ ID NO 528
<211> LENGTH: 21
<212> TYPE: DNA
<213> ORGANISM: Artificial Sequence
<220> FEATURE:
<223> OTHER INFORMATION: si-TD719

<400> SEQUENCE: 528
guacaggucu cucagcucct t                                              21

<210> SEQ ID NO 529
<211> LENGTH: 21
<212> TYPE: DNA
<213> ORGANISM: Artificial Sequence
<220> FEATURE:
<223> OTHER INFORMATION: si-TD718

<400> SEQUENCE: 529
gggagcugag agaccuguat t                                              21

<210> SEQ ID NO 530
<211> LENGTH: 21
<212> TYPE: DNA
<213> ORGANISM: Artificial Sequence
<220> FEATURE:
<223> OTHER INFORMATION: si-TD718

<400> SEQUENCE: 530
uacaggucuc ucagcuccct t                                              21

<210> SEQ ID NO 531
<211> LENGTH: 21
<212> TYPE: DNA
<213> ORGANISM: Artificial Sequence
<220> FEATURE:
<223> OTHER INFORMATION: si-TD742

<400> SEQUENCE: 531
agauggaccu gcagacccct t                                              21

<210> SEQ ID NO 532
<211> LENGTH: 21
<212> TYPE: DNA
<213> ORGANISM: Artificial Sequence
<220> FEATURE:
<223> OTHER INFORMATION: si-TD742

<400> SEQUENCE: 532
ggggucugca gguccaucut t                                              21

<210> SEQ ID NO 533
<211> LENGTH: 21
<212> TYPE: DNA
<213> ORGANISM: Artificial Sequence
<220> FEATURE:
<223> OTHER INFORMATION: si-TD741

<400> SEQUENCE: 533
cagauggacc ugcagaccct t                                              21

<210> SEQ ID NO 534
<211> LENGTH: 21
<212> TYPE: DNA
<213> ORGANISM: Artificial Sequence
<220> FEATURE:
<223> OTHER INFORMATION: si-TD741
```

```
<400> SEQUENCE: 534
gggucugcag guccaucugt t                                              21

<210> SEQ ID NO 535
<211> LENGTH: 21
<212> TYPE: DNA
<213> ORGANISM: Artificial Sequence
<220> FEATURE:
<223> OTHER INFORMATION: si-TD744

<400> SEQUENCE: 535
acucccaccu cagacagact t                                              21

<210> SEQ ID NO 536
<211> LENGTH: 21
<212> TYPE: DNA
<213> ORGANISM: Artificial Sequence
<220> FEATURE:
<223> OTHER INFORMATION: si-TD744

<400> SEQUENCE: 536
gucugucuga ggugggagut t                                              21

<210> SEQ ID NO 537
<211> LENGTH: 21
<212> TYPE: DNA
<213> ORGANISM: Artificial Sequence
<220> FEATURE:
<223> OTHER INFORMATION: si-TD743

<400> SEQUENCE: 537
gacucccacc ucagacagat t                                              21

<210> SEQ ID NO 538
<211> LENGTH: 21
<212> TYPE: DNA
<213> ORGANISM: Artificial Sequence
<220> FEATURE:
<223> OTHER INFORMATION: si-TD743

<400> SEQUENCE: 538
ucugucugag guggggaguct t                                             21

<210> SEQ ID NO 539
<211> LENGTH: 21
<212> TYPE: DNA
<213> ORGANISM: Artificial Sequence
<220> FEATURE:
<223> OTHER INFORMATION: si-TD144

<400> SEQUENCE: 539
gguaaaagau gagaaaaaut t                                              21

<210> SEQ ID NO 540
<211> LENGTH: 21
<212> TYPE: DNA
<213> ORGANISM: Artificial Sequence
<220> FEATURE:
<223> OTHER INFORMATION: si-TD144

<400> SEQUENCE: 540
auuuuucuca ucuuuuacct t                                              21
```

<210> SEQ ID NO 541
<211> LENGTH: 21
<212> TYPE: DNA
<213> ORGANISM: Artificial Sequence
<220> FEATURE:
<223> OTHER INFORMATION: si-TD145

<400> SEQUENCE: 541
guaaaagaug agaaaaauat t                                              21

<210> SEQ ID NO 542
<211> LENGTH: 21
<212> TYPE: DNA
<213> ORGANISM: Artificial Sequence
<220> FEATURE:
<223> OTHER INFORMATION: si-TD145

<400> SEQUENCE: 542
uauuuuucuc aucuuuuact t                                              21

<210> SEQ ID NO 543
<211> LENGTH: 21
<212> TYPE: DNA
<213> ORGANISM: Artificial Sequence
<220> FEATURE:
<223> OTHER INFORMATION: si-TD479

<400> SEQUENCE: 543
cucuugugcu gagagcuuut t                                              21

<210> SEQ ID NO 544
<211> LENGTH: 21
<212> TYPE: DNA
<213> ORGANISM: Artificial Sequence
<220> FEATURE:
<223> OTHER INFORMATION: si-TD479

<400> SEQUENCE: 544
aaagcucuca gcacaagagt t                                              21

<210> SEQ ID NO 545
<211> LENGTH: 21
<212> TYPE: DNA
<213> ORGANISM: Artificial Sequence
<220> FEATURE:
<223> OTHER INFORMATION: si-TD480

<400> SEQUENCE: 545
ucuugugcug agagcuuuct t                                              21

<210> SEQ ID NO 546
<211> LENGTH: 21
<212> TYPE: DNA
<213> ORGANISM: Artificial Sequence
<220> FEATURE:
<223> OTHER INFORMATION: si-TD480

<400> SEQUENCE: 546
gaaagcucuc agcacaagat t                                              21

<210> SEQ ID NO 547
<211> LENGTH: 21
<212> TYPE: DNA
<213> ORGANISM: Artificial Sequence
<220> FEATURE:
<223> OTHER INFORMATION: si-TD481

```
<400> SEQUENCE: 547
cuugugcuga gagcuuucgt t                                              21

<210> SEQ ID NO 548
<211> LENGTH: 21
<212> TYPE: DNA
<213> ORGANISM: Artificial Sequence
<220> FEATURE:
<223> OTHER INFORMATION: si-TD481

<400> SEQUENCE: 548
cgaaagcucu cagcacaagt t                                              21

<210> SEQ ID NO 549
<211> LENGTH: 21
<212> TYPE: DNA
<213> ORGANISM: Artificial Sequence
<220> FEATURE:
<223> OTHER INFORMATION: si-TD482-F

<400> SEQUENCE: 549
uugugcugag agcuuucggt t                                              21

<210> SEQ ID NO 550
<211> LENGTH: 21
<212> TYPE: DNA
<213> ORGANISM: Artificial Sequence
<220> FEATURE:
<223> OTHER INFORMATION: si-TD482-R

<400> SEQUENCE: 550
ccgaaagcuc ucagcacaat t                                              21

<210> SEQ ID NO 551
<211> LENGTH: 21
<212> TYPE: DNA
<213> ORGANISM: Artificial Sequence
<220> FEATURE:
<223> OTHER INFORMATION: si-TD483-F

<400> SEQUENCE: 551
ugugcugaga gcuuucgggt t                                              21

<210> SEQ ID NO 552
<211> LENGTH: 21
<212> TYPE: DNA
<213> ORGANISM: Artificial Sequence
<220> FEATURE:
<223> OTHER INFORMATION: si-TD483-R

<400> SEQUENCE: 552
cccgaaagcu cucagcacat t                                              21

<210> SEQ ID NO 553
<211> LENGTH: 21
<212> TYPE: DNA
<213> ORGANISM: Artificial Sequence
<220> FEATURE:
<223> OTHER INFORMATION: si-TD584-F

<400> SEQUENCE: 553
ggggcagcug ucccggauct t                                              21
```

<210> SEQ ID NO 554
<211> LENGTH: 21
<212> TYPE: DNA
<213> ORGANISM: Artificial Sequence
<220> FEATURE:
<223> OTHER INFORMATION: si-TD584-R

<400> SEQUENCE: 554
gauccgggac agcugcccct t                                              21

<210> SEQ ID NO 555
<211> LENGTH: 21
<212> TYPE: DNA
<213> ORGANISM: Artificial Sequence
<220> FEATURE:
<223> OTHER INFORMATION: si-TD583-F

<400> SEQUENCE: 555
cggggcagcu gucccggaut t                                              21

<210> SEQ ID NO 556
<211> LENGTH: 21
<212> TYPE: DNA
<213> ORGANISM: Artificial Sequence
<220> FEATURE:
<223> OTHER INFORMATION: si-TD583-R

<400> SEQUENCE: 556
auccgggaca gcugccccgt t                                              21

<210> SEQ ID NO 557
<211> LENGTH: 21
<212> TYPE: DNA
<213> ORGANISM: Artificial Sequence
<220> FEATURE:
<223> OTHER INFORMATION: si-TD582-F

<400> SEQUENCE: 557
ccggggcagc ugucccggat t                                              21

<210> SEQ ID NO 558
<211> LENGTH: 21
<212> TYPE: DNA
<213> ORGANISM: Artificial Sequence
<220> FEATURE:
<223> OTHER INFORMATION: si-TD582-R

<400> SEQUENCE: 558
uccgggacag cugccccggt t                                              21

<210> SEQ ID NO 559
<211> LENGTH: 21
<212> TYPE: DNA
<213> ORGANISM: Artificial Sequence
<220> FEATURE:
<223> OTHER INFORMATION: si-TD740-F

<400> SEQUENCE: 559
acagauggac cugcagacct t                                              21

<210> SEQ ID NO 560
<211> LENGTH: 21
<212> TYPE: DNA
<213> ORGANISM: Artificial Sequence
<220> FEATURE:
<223> OTHER INFORMATION: si-TD740-R

<400> SEQUENCE: 560
ggucugcagg uccaucugut t                                              21

<210> SEQ ID NO 561
<211> LENGTH: 21
<212> TYPE: DNA
<213> ORGANISM: Artificial Sequence
<220> FEATURE:
<223> OTHER INFORMATION: si-TD739-F

<400> SEQUENCE: 561
gacagaugga ccugcagact t                                              21

<210> SEQ ID NO 562
<211> LENGTH: 21
<212> TYPE: DNA
<213> ORGANISM: Artificial Sequence
<220> FEATURE:
<223> OTHER INFORMATION: si-TD739-R

<400> SEQUENCE: 562
gucugcaggu ccaucuguct t                                              21

<210> SEQ ID NO 563
<211> LENGTH: 21
<212> TYPE: DNA
<213> ORGANISM: Artificial Sequence
<220> FEATURE:
<223> OTHER INFORMATION: si-TD738-F

<400> SEQUENCE: 563
agacagaugg accugcagat t                                              21

<210> SEQ ID NO 564
<211> LENGTH: 21
<212> TYPE: DNA
<213> ORGANISM: Artificial Sequence
<220> FEATURE:
<223> OTHER INFORMATION: si-TD738-R

<400> SEQUENCE: 564
ucugcagguc caucugucut t                                              21

<210> SEQ ID NO 565
<211> LENGTH: 21
<212> TYPE: DNA
<213> ORGANISM: Artificial Sequence
<220> FEATURE:
<223> OTHER INFORMATION: si-TD737-F

<400> SEQUENCE: 565
cagacagaug gaccugcagt t                                              21

<210> SEQ ID NO 566
<211> LENGTH: 21
<212> TYPE: DNA
<213> ORGANISM: Artificial Sequence
<220> FEATURE:
<223> OTHER INFORMATION: si-TD737-R

<400> SEQUENCE: 566
cugcaggucc aucugucugt t                                              21

-continued

```
<210> SEQ ID NO 567
<211> LENGTH: 21
<212> TYPE: DNA
<213> ORGANISM: Artificial Sequence
<220> FEATURE:
<223> OTHER INFORMATION: si-TD736-F

<400> SEQUENCE: 567
acagacagau ggaccugcat t                                          21

<210> SEQ ID NO 568
<211> LENGTH: 21
<212> TYPE: DNA
<213> ORGANISM: Artificial Sequence
<220> FEATURE:
<223> OTHER INFORMATION: si-TD736-R

<400> SEQUENCE: 568
ugcaggucca ucugucugut t                                          21

<210> SEQ ID NO 569
<211> LENGTH: 21
<212> TYPE: DNA
<213> ORGANISM: Artificial Sequence
<220> FEATURE:
<223> OTHER INFORMATION: si-TD735-F

<400> SEQUENCE: 569
uacagacaga uggaccugct t                                          21

<210> SEQ ID NO 570
<211> LENGTH: 21
<212> TYPE: DNA
<213> ORGANISM: Artificial Sequence
<220> FEATURE:
<223> OTHER INFORMATION: si-TD735-R

<400> SEQUENCE: 570
gcagguccau cugucuguat t                                          21

<210> SEQ ID NO 571
<211> LENGTH: 21
<212> TYPE: DNA
<213> ORGANISM: Artificial Sequence
<220> FEATURE:
<223> OTHER INFORMATION: si-TD734-F

<400> SEQUENCE: 571
guacagacag auggaccugt t                                          21

<210> SEQ ID NO 572
<211> LENGTH: 21
<212> TYPE: DNA
<213> ORGANISM: Artificial Sequence
<220> FEATURE:
<223> OTHER INFORMATION: si-TD734-R

<400> SEQUENCE: 572
cagguccauc ugucuguact t                                          21

<210> SEQ ID NO 573
<211> LENGTH: 21
<212> TYPE: DNA
<213> ORGANISM: Artificial Sequence
<220> FEATURE:
<223> OTHER INFORMATION: si-TD733-F
```

```
<400> SEQUENCE: 573
uguacagaca gauggaccut t                                              21

<210> SEQ ID NO 574
<211> LENGTH: 21
<212> TYPE: DNA
<213> ORGANISM: Artificial Sequence
<220> FEATURE:
<223> OTHER INFORMATION: si-TD733-R

<400> SEQUENCE: 574
agguccaucu gucuguacat t                                              21

<210> SEQ ID NO 575
<211> LENGTH: 21
<212> TYPE: DNA
<213> ORGANISM: Artificial Sequence
<220> FEATURE:
<223> OTHER INFORMATION: si-TD732-F

<400> SEQUENCE: 575
cuguacagac agauggacct t                                              21

<210> SEQ ID NO 576
<211> LENGTH: 21
<212> TYPE: DNA
<213> ORGANISM: Artificial Sequence
<220> FEATURE:
<223> OTHER INFORMATION: si-TD732-R

<400> SEQUENCE: 576
gguccaucug ucuguacagt t                                              21

<210> SEQ ID NO 577
<211> LENGTH: 21
<212> TYPE: DNA
<213> ORGANISM: Artificial Sequence
<220> FEATURE:
<223> OTHER INFORMATION: si-TD731-F

<400> SEQUENCE: 577
ccuguacaga cagauggact t                                              21

<210> SEQ ID NO 578
<211> LENGTH: 21
<212> TYPE: DNA
<213> ORGANISM: Artificial Sequence
<220> FEATURE:
<223> OTHER INFORMATION: si-TD731-R

<400> SEQUENCE: 578
guccaucugu cuguacaggt t                                              21

<210> SEQ ID NO 579
<211> LENGTH: 21
<212> TYPE: DNA
<213> ORGANISM: Artificial Sequence
<220> FEATURE:
<223> OTHER INFORMATION: si-TD730-F

<400> SEQUENCE: 579
accuguacag acagauggat t                                              21
```

```
<210> SEQ ID NO 580
<211> LENGTH: 21
<212> TYPE: DNA
<213> ORGANISM: Artificial Sequence
<220> FEATURE:
<223> OTHER INFORMATION: si-TD730-R

<400> SEQUENCE: 580
uccaucuguc uguacaggut t                                              21

<210> SEQ ID NO 581
<211> LENGTH: 21
<212> TYPE: DNA
<213> ORGANISM: Artificial Sequence
<220> FEATURE:
<223> OTHER INFORMATION: si-TD729-F

<400> SEQUENCE: 581
gaccuguaca gacagauggt t                                              21

<210> SEQ ID NO 582
<211> LENGTH: 21
<212> TYPE: DNA
<213> ORGANISM: Artificial Sequence
<220> FEATURE:
<223> OTHER INFORMATION: si-TD729-R

<400> SEQUENCE: 582
ccaucugucu guacagguct t                                              21

<210> SEQ ID NO 583
<211> LENGTH: 21
<212> TYPE: DNA
<213> ORGANISM: Artificial Sequence
<220> FEATURE:
<223> OTHER INFORMATION: si-TD728-F

<400> SEQUENCE: 583
agaccuguac agacagaugt t                                              21

<210> SEQ ID NO 584
<211> LENGTH: 21
<212> TYPE: DNA
<213> ORGANISM: Artificial Sequence
<220> FEATURE:
<223> OTHER INFORMATION: si-TD728-R

<400> SEQUENCE: 584
caucugucug uacaggucut t                                              21

<210> SEQ ID NO 585
<211> LENGTH: 21
<212> TYPE: DNA
<213> ORGANISM: Artificial Sequence
<220> FEATURE:
<223> OTHER INFORMATION: si-TD727-F

<400> SEQUENCE: 585
gagaccugua cagacagaut t                                              21

<210> SEQ ID NO 586
<211> LENGTH: 21
<212> TYPE: DNA
<213> ORGANISM: Artificial Sequence
<220> FEATURE:
<223> OTHER INFORMATION: si-TD727-R
```

```
<400> SEQUENCE: 586
aucugucugu acaggucuct t                                              21

<210> SEQ ID NO 587
<211> LENGTH: 21
<212> TYPE: DNA
<213> ORGANISM: Artificial Sequence
<220> FEATURE:
<223> OTHER INFORMATION: si-TD726-F

<400> SEQUENCE: 587
agagaccugu acagacagat t                                              21

<210> SEQ ID NO 588
<211> LENGTH: 21
<212> TYPE: DNA
<213> ORGANISM: Artificial Sequence
<220> FEATURE:
<223> OTHER INFORMATION: si-TD726-R

<400> SEQUENCE: 588
ucugucugua caggucucut t                                              21

<210> SEQ ID NO 589
<211> LENGTH: 21
<212> TYPE: DNA
<213> ORGANISM: Artificial Sequence
<220> FEATURE:
<223> OTHER INFORMATION: si-TD725-F

<400> SEQUENCE: 589
gagagaccug uacagacagt t                                              21

<210> SEQ ID NO 590
<211> LENGTH: 21
<212> TYPE: DNA
<213> ORGANISM: Artificial Sequence
<220> FEATURE:
<223> OTHER INFORMATION: si-TD725-R

<400> SEQUENCE: 590
cugucuguac aggucucuct t                                              21

<210> SEQ ID NO 591
<211> LENGTH: 21
<212> TYPE: DNA
<213> ORGANISM: Artificial Sequence
<220> FEATURE:
<223> OTHER INFORMATION: si-TD723-F

<400> SEQUENCE: 591
cugagagacc uguacagact t                                              21

<210> SEQ ID NO 592
<211> LENGTH: 21
<212> TYPE: DNA
<213> ORGANISM: Artificial Sequence
<220> FEATURE:
<223> OTHER INFORMATION: si-TD723-R

<400> SEQUENCE: 592
gucuguacag gucucucagt t                                              21
```

```
<210> SEQ ID NO 593
<211> LENGTH: 21
<212> TYPE: DNA
<213> ORGANISM: Artificial Sequence
<220> FEATURE:
<223> OTHER INFORMATION: si-TD722-F

<400> SEQUENCE: 593
gcugagagac cuguacagat t                                          21

<210> SEQ ID NO 594
<211> LENGTH: 21
<212> TYPE: DNA
<213> ORGANISM: Artificial Sequence
<220> FEATURE:
<223> OTHER INFORMATION: si-TD722-R

<400> SEQUENCE: 594
ucuguacagg ucucucagct t                                          21

<210> SEQ ID NO 595
<211> LENGTH: 21
<212> TYPE: DNA
<213> ORGANISM: Artificial Sequence
<220> FEATURE:
<223> OTHER INFORMATION: si-TD717-F

<400> SEQUENCE: 595
agggagcuga gagaccugut t                                          21

<210> SEQ ID NO 596
<211> LENGTH: 21
<212> TYPE: DNA
<213> ORGANISM: Artificial Sequence
<220> FEATURE:
<223> OTHER INFORMATION: si-TD717-R

<400> SEQUENCE: 596
acaggucucu cagcucccut t                                          21

<210> SEQ ID NO 597
<211> LENGTH: 21
<212> TYPE: DNA
<213> ORGANISM: Artificial Sequence
<220> FEATURE:
<223> OTHER INFORMATION: si-TD716-F

<400> SEQUENCE: 597
cagggagcug agagaccugt t                                          21

<210> SEQ ID NO 598
<211> LENGTH: 21
<212> TYPE: DNA
<213> ORGANISM: Artificial Sequence
<220> FEATURE:
<223> OTHER INFORMATION: si-TD716-R

<400> SEQUENCE: 598
caggucucuc agcucccugt t                                          21

<210> SEQ ID NO 599
<211> LENGTH: 21
<212> TYPE: DNA
<213> ORGANISM: Artificial Sequence
<220> FEATURE:
<223> OTHER INFORMATION: si-TD715-F
```

<400> SEQUENCE: 599
ucagggagcu gagagaccut t          21

<210> SEQ ID NO 600
<211> LENGTH: 21
<212> TYPE: DNA
<213> ORGANISM: Artificial Sequence
<220> FEATURE:
<223> OTHER INFORMATION: si-TD715-R

<400> SEQUENCE: 600
aggucucuca gcucccugat t          21

<210> SEQ ID NO 601
<211> LENGTH: 21
<212> TYPE: DNA
<213> ORGANISM: Artificial Sequence
<220> FEATURE:
<223> OTHER INFORMATION: si-TD714-F

<400> SEQUENCE: 601
gucagggagc ugagagacct t          21

<210> SEQ ID NO 602
<211> LENGTH: 21
<212> TYPE: DNA
<213> ORGANISM: Artificial Sequence
<220> FEATURE:
<223> OTHER INFORMATION: si-TD714-R

<400> SEQUENCE: 602
ggucucucag cucccugact t          21

<210> SEQ ID NO 603
<211> LENGTH: 21
<212> TYPE: DNA
<213> ORGANISM: Artificial Sequence
<220> FEATURE:
<223> OTHER INFORMATION: si-7-F

<400> SEQUENCE: 603
ugggagaugg gaagcgaaat t          21

<210> SEQ ID NO 604
<211> LENGTH: 21
<212> TYPE: DNA
<213> ORGANISM: Artificial Sequence
<220> FEATURE:
<223> OTHER INFORMATION: si-7-R

<400> SEQUENCE: 604
uuucgcuucc caucucccat t          21

<210> SEQ ID NO 605
<211> LENGTH: 21
<212> TYPE: DNA
<213> ORGANISM: Artificial Sequence
<220> FEATURE:
<223> OTHER INFORMATION: si-10-F

<400> SEQUENCE: 605
cagacaaagg ggccaccuat t          21

```
<210> SEQ ID NO 606
<211> LENGTH: 21
<212> TYPE: DNA
<213> ORGANISM: Artificial Sequence
<220> FEATURE:
<223> OTHER INFORMATION: si-10-R

<400> SEQUENCE: 606
uagguggccc cuuugucugt t                                              21

<210> SEQ ID NO 607
<211> LENGTH: 21
<212> TYPE: DNA
<213> ORGANISM: Artificial Sequence
<220> FEATURE:
<223> OTHER INFORMATION: si-1-F

<400> SEQUENCE: 607
ggaccuggua gcaaggaaat t                                              21

<210> SEQ ID NO 608
<211> LENGTH: 21
<212> TYPE: DNA
<213> ORGANISM: Artificial Sequence
<220> FEATURE:
<223> OTHER INFORMATION: si-1-R

<400> SEQUENCE: 608
uuuccuugcu accaggucct t                                              21

<210> SEQ ID NO 609
<211> LENGTH: 21
<212> TYPE: DNA
<213> ORGANISM: Artificial Sequence
<220> FEATURE:
<223> OTHER INFORMATION: NC-1-F

<400> SEQUENCE: 609
gaaagauaga gaagguagat t                                              21

<210> SEQ ID NO 610
<211> LENGTH: 21
<212> TYPE: DNA
<213> ORGANISM: Artificial Sequence
<220> FEATURE:
<223> OTHER INFORMATION: NC-1-R

<400> SEQUENCE: 610
ucuaccuucu cuaucuuuct t                                              21

<210> SEQ ID NO 611
<211> LENGTH: 21
<212> TYPE: DNA
<213> ORGANISM: Artificial Sequence
<220> FEATURE:
<223> OTHER INFORMATION: NC-2-F

<400> SEQUENCE: 611
gcaacagccg augaaguuat t                                              21

<210> SEQ ID NO 612
<211> LENGTH: 21
<212> TYPE: DNA
<213> ORGANISM: Artificial Sequence
<220> FEATURE:
<223> OTHER INFORMATION: NC-2-R
```

<400> SEQUENCE: 612
uaacuucauc ggcuguugct t                                              21

<210> SEQ ID NO 613
<211> LENGTH: 21
<212> TYPE: DNA
<213> ORGANISM: Artificial Sequence
<220> FEATURE:
<223> OTHER INFORMATION: NC-3-F

<400> SEQUENCE: 613
ggccgagcaa cgaaugucat t                                              21

<210> SEQ ID NO 614
<211> LENGTH: 21
<212> TYPE: DNA
<213> ORGANISM: Artificial Sequence
<220> FEATURE:
<223> OTHER INFORMATION: NC-3-R

<400> SEQUENCE: 614
ugacauucgu ugcucggcct t                                              21

<210> SEQ ID NO 615
<211> LENGTH: 21
<212> TYPE: DNA
<213> ORGANISM: Artificial Sequence
<220> FEATURE:
<223> OTHER INFORMATION: NC-4-F

<400> SEQUENCE: 615
ggacaucgaa cgaagugcut t                                              21

<210> SEQ ID NO 616
<211> LENGTH: 21
<212> TYPE: DNA
<213> ORGANISM: Artificial Sequence
<220> FEATURE:
<223> OTHER INFORMATION: NC-4-R

<400> SEQUENCE: 616
agcacuucgu ucgaugucct t                                              21

<210> SEQ ID NO 617
<211> LENGTH: 21
<212> TYPE: DNA
<213> ORGANISM: Artificial Sequence
<220> FEATURE:
<223> OTHER INFORMATION: NC-5-F

<400> SEQUENCE: 617
gcggucccug cgacguacat t                                              21

<210> SEQ ID NO 618
<211> LENGTH: 21
<212> TYPE: DNA
<213> ORGANISM: Artificial Sequence
<220> FEATURE:
<223> OTHER INFORMATION: NC-5-R

<400> SEQUENCE: 618
uguacgucgc agggaccgct t                                              21

```
<210> SEQ ID NO 619
<211> LENGTH: 21
<212> TYPE: DNA
<213> ORGANISM: Artificial Sequence
<220> FEATURE:
<223> OTHER INFORMATION: NC-6-F

<400> SEQUENCE: 619
gcugcgcgaa cccaucaaat t                                              21

<210> SEQ ID NO 620
<211> LENGTH: 21
<212> TYPE: DNA
<213> ORGANISM: Artificial Sequence
<220> FEATURE:
<223> OTHER INFORMATION: NC-6-R

<400> SEQUENCE: 620
uuugaugggu ucgcgcagct t                                              21

<210> SEQ ID NO 621
<211> LENGTH: 21
<212> TYPE: DNA
<213> ORGANISM: Artificial Sequence
<220> FEATURE:
<223> OTHER INFORMATION: NC-7-F

<400> SEQUENCE: 621
uucuccgaac gugucacgut t                                              21

<210> SEQ ID NO 622
<211> LENGTH: 21
<212> TYPE: DNA
<213> ORGANISM: Artificial Sequence
<220> FEATURE:
<223> OTHER INFORMATION: NC-7-R

<400> SEQUENCE: 622
acgugacacg uucggagaat t                                              21

<210> SEQ ID NO 623
<211> LENGTH: 21
<212> TYPE: DNA
<213> ORGANISM: Artificial Sequence
<220> FEATURE:
<223> OTHER INFORMATION: NC-8-F

<400> SEQUENCE: 623
gcgacgaucu gccuaagaut t                                              21

<210> SEQ ID NO 624
<211> LENGTH: 21
<212> TYPE: DNA
<213> ORGANISM: Artificial Sequence
<220> FEATURE:
<223> OTHER INFORMATION: NC-8-R

<400> SEQUENCE: 624
aucuuaggca gaucgucgct t                                              21

<210> SEQ ID NO 625
<211> LENGTH: 70
<212> TYPE: DNA
<213> ORGANISM: Artificial Sequence
<220> FEATURE:
<223> OTHER INFORMATION: multiple cloning site (MCS) of the pGP-miRGLO
      vector
```

```
<400> SEQUENCE: 625
gcaagatcgc cgtgtaattc tagttgttta aacgagctcg ctagcctcga gtctagagtc    60
gacctgcagg                                                           70
```

DOUBLE-STRANDED RNA MOLECULE TARGETING CKIP-1 AND USE THEREOF

CROSS-REFERENCE TO RELATED APPLICATIONS

This application is a divisional of U.S. patent application Ser. No. 16/644,977, which has a 371(c) Date of Mar. 6, 2020, which is a U.S. 371 Nat'l Stage Appl. of Int'l Appl. No. PCT/CN2018/104552, filed Sep. 7, 2018, which claims priority to Int'l Appl. Nos. PCT/CN2017/100863, filed Sep. 7, 2017, PCT/CN2017/100864, filed Sep. 7, 2017, PCT/CN2017/100865, filed Sep. 7, 2017, PCT/CN2017/100866, filed Sep. 7, 2017, and PCT/CN2017/100867, filed Sep. 7, 2017, all of which are incorporated herein by reference.

FIELD OF THE INVENTION

The present invention relates to the field of biomedicine, particularly to double-stranded RNA molecules targeting CKIP-1 and uses thereof, particularly to use of the double-stranded RNA molecules for the treatment of inflammatory diseases such as arthritis, particularly rheumatoid arthritis.

REFERENCE TO THE SEQUENCE LISTING

This application includes as part of its disclosure a biological sequence listing which is being concurrently submitted through EFS-Web. Said biological sequence listing is contained in a file named "115849800001802.txt" which was created on Dec. 4, 2023, and has a size of 115,053 bytes, and is hereby incorporated by reference in its entirety.

BACKGROUND OF THE INVENTION

Casein Kinase Interacting Protein 1 (CKIP-1) is a bone formation inhibiting gene that specifically regulates bone formation rather than bone resorption. CKIP-1 is highly expressed in bone tissue of patients with osteoporosis. Targeted inhibition of CKIP-1 expression has been proven to be useful in the treatment of osteoporosis or other pathological bone destruction. However, CKIP-1 has not been associated with inflammation in the art.

TNF-α and IL-6 are two important pro-inflammatory cytokines and play an important role in the inflammatory response of the body. The levels of TNF-α and IL-6 are low in human bodies under physiological conditions. However, under pathological conditions, increased secretion of TNF-α and IL-6, and the resulting cascade of various pro-inflammatory factors, can lead to an inflammatory response, and thus tissue damage. Inflammatory diseases have been treated in the art by targeted inhibition of TNF-α and IL-6. For example, a number of inhibitors targeting TNF-α have been marketed, including Infliximab, Etanercept, Adalimumab, Golimumab, and Certolizumab. In addition, IL-6 blockers have been marketed for clinical use, such as tolizumab. In a large randomized, double-blind clinical trial, tolizumab has a good therapeutic effect in patients who do not respond to TNF-α mAb.

Rheumatoid arthritis (RA) is a chronic systemic autoimmune disease characterized by multi-joint synovitis. Prolonged recurrent episodes of synovitis can lead to destruction of intra-articular cartilage and bone, joint dysfunction, and even disability. Rheumatoid arthritis has a high incidence in adults, about 20-40% per 100,000 adults. Studies have shown that 70-75% of rheumatoid arthritis patients have bone destruction within 3 years of onset, 10% of them have severe dysfunction within 2 years of onset, and about 50% of them lose their ability to work after 10 years of onset, resulting in serious economic burden to both patients and society. At present, the drugs for treating RA mainly comprise non-steroidal anti-inflammatory drugs, hormones, anti-rheumatic drugs and the like, and are mainly used for relieving pain, relieving inflammation but are not effective in preventing joint and bone destruction. In recent years, some new biological agents can alleviate and inhibit the occurrence of bone destruction, but cannot repair the existing bone injury. There is currently a clinical lack of RA therapeutics that both reduce inflammation and promote bone repair.

SUMMARY OF THE INVENTION

In a first aspect, the present invention provides a double-stranded RNA (dsRNA) molecule comprising a sense strand and an antisense strand which are selected from the group consisting of:
1) a sense strand shown in SEQ ID NO: 63 and an antisense strand shown in SEQ ID NO: 64;
2) a sense strand shown in SEQ ID NO: 71 and an antisense strand shown in SEQ ID NO: 72;
3) a sense strand shown in SEQ ID NO: 83 and an antisense strand shown in SEQ ID NO: 84; and
4) a sense strand shown in SEQ ID NO: 161 and an antisense strand shown in SEQ ID NO: 162.

In some embodiments, the sense and/or antisense strand additionally has an overhang of at least one nucleotide at the 3' end. In some embodiments, the sense and/or antisense strand additionally has an overhang of 2 nucleotides at the 3' end, preferably the overhang is TT.

In some embodiments, the sense and antisense strands comprise 1 or 2 nucleotide substitutions located within the 6, 5, 4, 3, or 2 nucleotides from the 5' and/or 3' end. In some embodiments, the sense and antisense strands comprise 1 nucleotide substitution located at the last nucleotide of the 3' end of the sense strand and correspondingly at the first nucleotide of the 5' end of the antisense strand.

In some embodiments, the dsRNA comprises at least one modified nucleotide. In some embodiments, the modified nucleotide is selected from the group consisting of: 2'-O-methyl modified nucleotides, 2'-F modified nucleotides, nucleotides containing 5'-phosphorothioate groups and end nucleotides linked to cholesteryl derivatives or dodecanoic acid bisdecylamide groups, 2'-deoxy-2'-fluoro modified nucleotides, 2'-deoxy-modified nucleotides, locked nucleotides, abasic nucleotides, 2'-amino-modified nucleotides, 2'-alkyl-modified nucleotides, morpholino nucleotides, phosphoramidates and nucleotides containing non-natural bases. In some embodiments, the 2' hydroxyl groups of all nucleotides with uracil or cytosine bases in the sense and/or antisense strands of the dsRNA are modified with methoxy groups.

In some embodiments, the dsRNA molecule is an siRNA or shRNA. In some embodiments, the dsRNA molecule inhibits CKIP-1 expression by at least 50%, preferably by at least 70%. In some embodiments, the dsRNA molecule inhibits expression of a pro-inflammatory cytokine such as IL-6, TNF-α, and/or IL-17A.

In a second aspect, the invention also provides an expression vector comprising a nucleotide sequence encoding the dsRNA molecule of the invention, and the nucleotide sequence is operably linked to a transcription regulation element.

In a third aspect, the invention also provides a pharmaceutical composition comprising the dsRNA molecule of the invention or the expression vector of the invention, and a pharmaceutically acceptable carrier.

In a fourth aspect, the invention provides a method of treating arthritis, particularly rheumatoid arthritis, in a subject in need thereof, comprising administering to the subject a therapeutically effective amount of the dsRNA molecule of the invention or the expression vector of the invention or the pharmaceutical composition of the invention. In some embodiments, the method further comprises administering to the subject an additional therapeutic agent for treating arthritis, particularly rheumatoid arthritis.

In a fifth aspect, the invention provides the use of the dsRNA molecule of the invention or the expression vector of the invention or the pharmaceutical composition of the invention for the manufacture of a medicament for the treatment of arthritis, in particular rheumatoid arthritis, in a subject in need thereof.

In a sixth aspect, the invention provides a method of treating an inflammatory disease in a subject in need thereof, comprising administering to the subject a therapeutically effective amount of the dsRNA molecule of the invention or the expression vector of the invention or the pharmaceutical composition of the invention. In some embodiments, the method further comprises administering to the subject an additional therapeutic agent for treating an inflammatory disease.

In a seventh aspect, the invention provides the use of the dsRNA molecule of the invention or the expression vector of the invention or the pharmaceutical composition of the invention in the preparation of a medicament for treating an inflammatory disease in a subject in need thereof.

In an eighth aspect, the present invention provides a method of treating a bone metabolism-related disorder in a subject in need thereof, comprising administering to the subject a therapeutically effective amount of the dsRNA molecule of the present invention or the expression vector of the present invention or the pharmaceutical composition of the present invention. In some embodiments, the method further comprises administering to the subject an additional therapeutic agent for treating a bone metabolism-related disorder.

In a ninth aspect, the invention provides the use of the dsRNA molecule of the invention or the expression vector of the invention or the pharmaceutical composition of the invention in the preparation of a medicament for treating a bone metabolism-related disorder in a subject in need thereof.

In various aspects of the invention, the subject is a human.

BRIEF DESCRIPTION OF THE DRAWINGS

FIGS. 1A-1E show a pool of candidate siRNA sequences, and the TT at the 3' end of each sequence is the overhang which is not complementary to the target sequence.

FIG. 1 shows a pool of candidate siRNA sequences, and the TT at the 3' end of each sequence is the overhang which is not complementary to the target sequence.

DETAILED DESCRIPTION OF THE INVENTION

I. Definition

Figure 2:
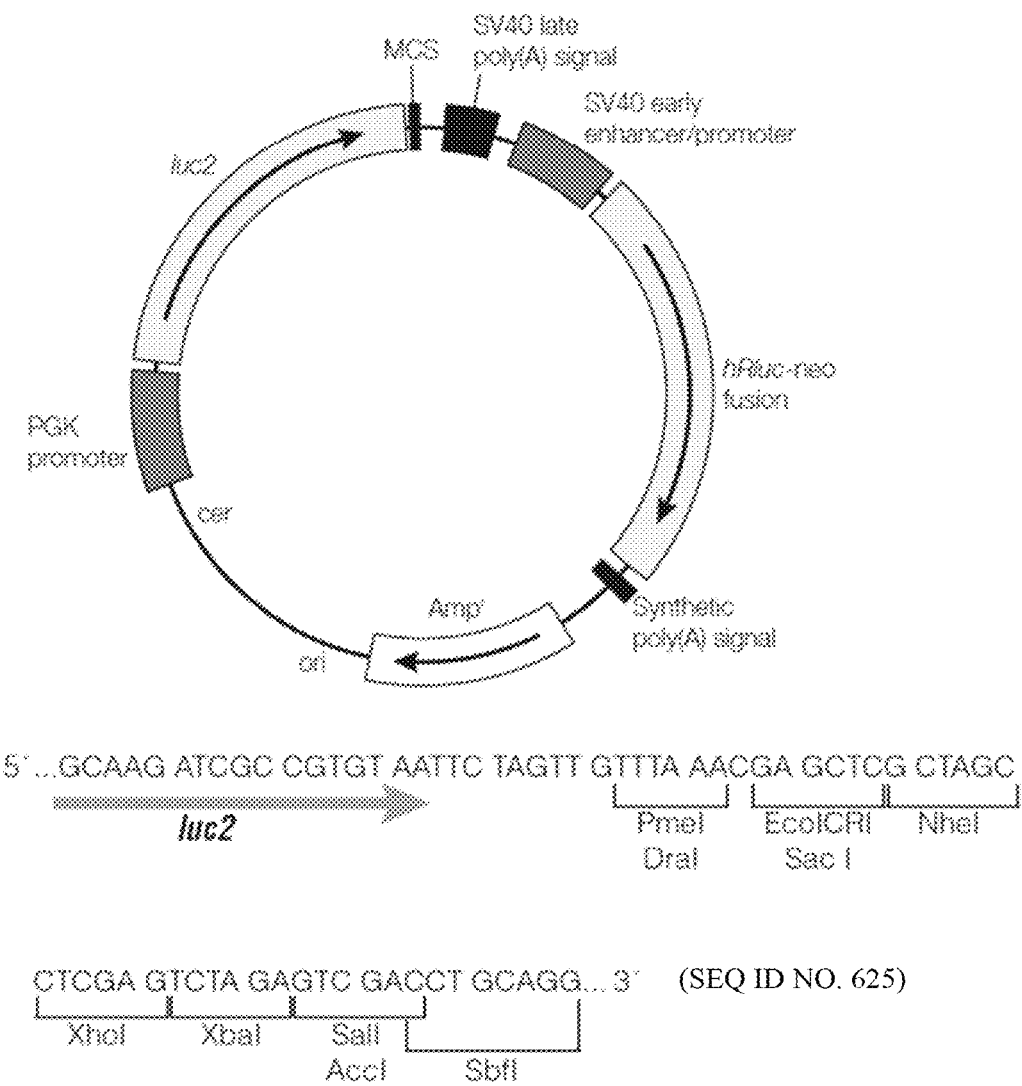
FIG. 2 shows the map of an overexpression vector for dual luciferase assay.
Figure 3:
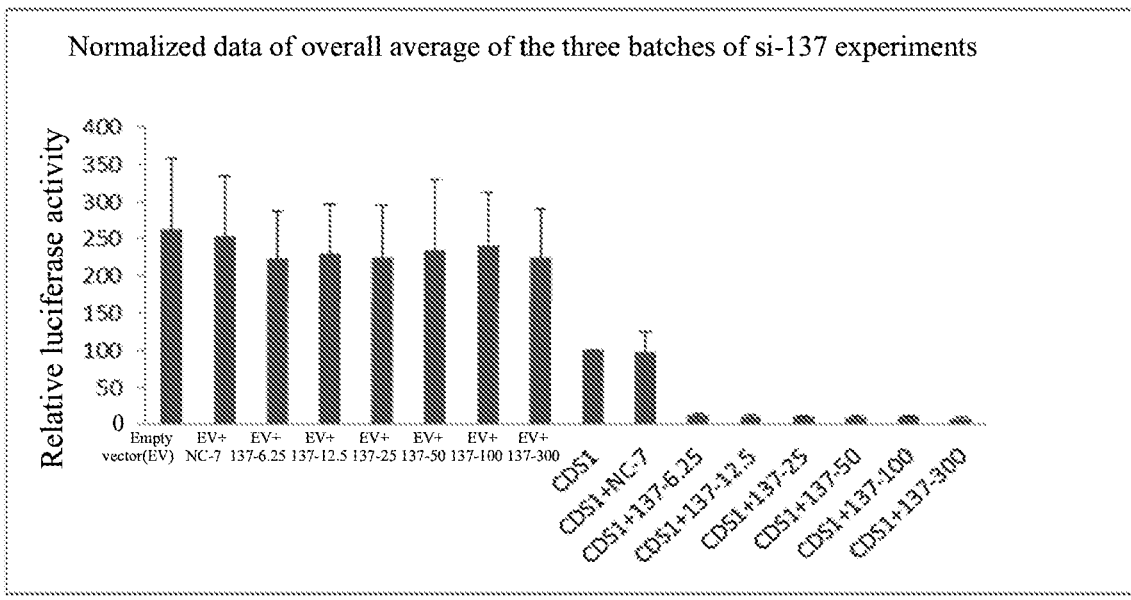
FIG. 3 shows the inhibitory effect of si-TD137 on CKIP-1 expression in a dual luciferase assay.
Figure 4:
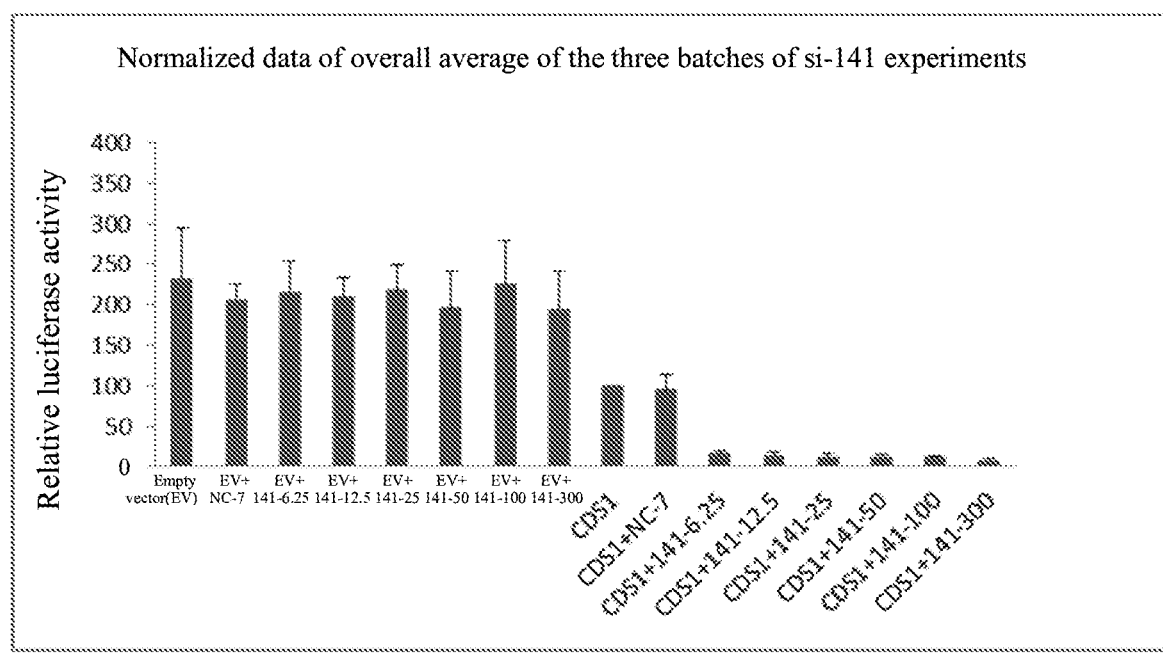
FIG. 4 shows the inhibitory effect of si-TD141 on CKIP-1 expression in a dual luciferase assay.
Figure 5:
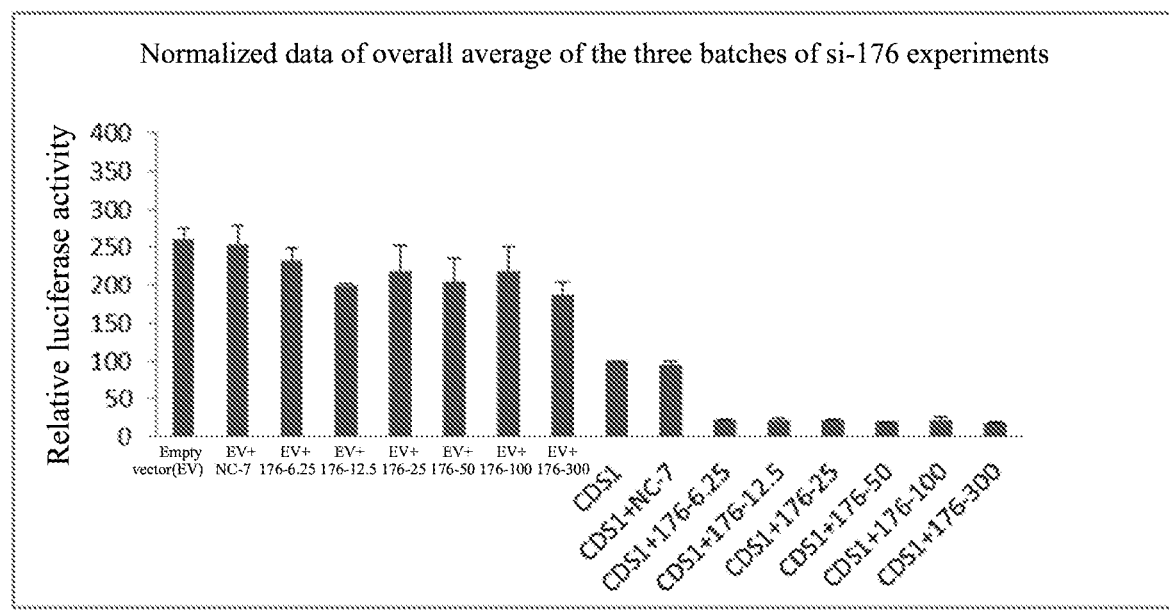
FIG. 5 shows the inhibitory effect of si-TD176 on CKIP-1 expression in a dual luciferase assay.
Figure 6:
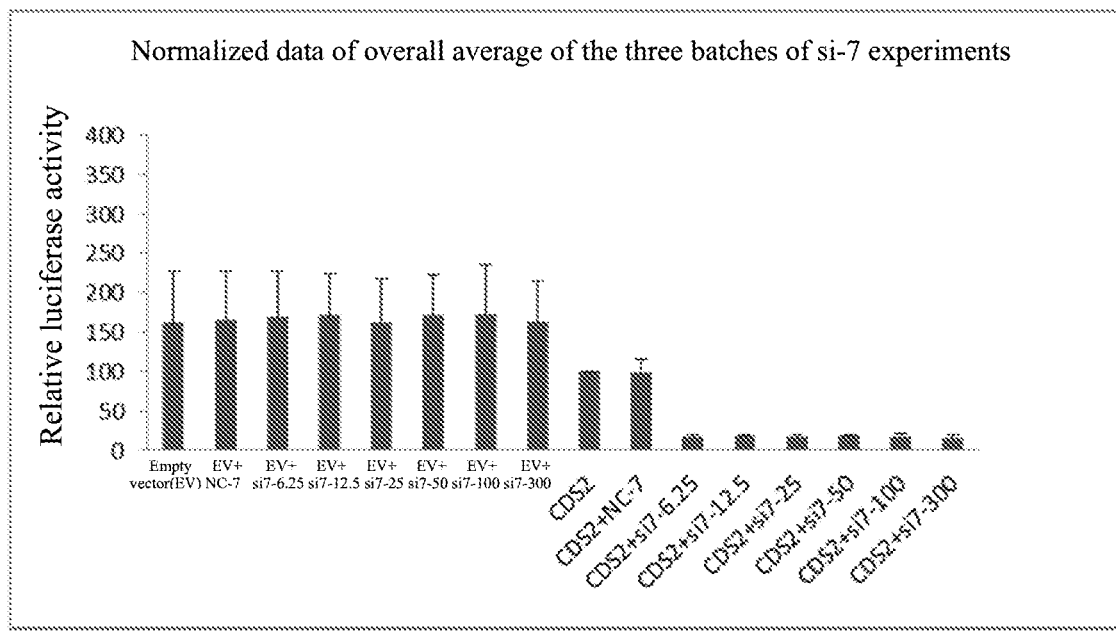
FIG. 6 shows the inhibitory effect of si-7 on CKIP-1 expression in a dual luciferase assay.

In the present invention, unless otherwise indicated, scientific and technical terms used herein have the meaning commonly understood by those skilled in the art. Moreover, the terms related to protein and nucleic acid chemistry, molecular biology, cell and tissue culture, microbiology, immunology, and laboratory procedures and routine procedures used herein are terms and procedures widely used in the relevant fields. Meanwhile, in order to better understand the present invention, definitions and explanations of related terms are provided below.

Unless otherwise indicated, the nucleic acid sequences recited herein are written in a direction from 5' to 3'. The term "nucleic acid" refers to DNA or RNA or modified forms thereof comprising purine or pyrimidine bases present in DNA (adenine "A", cytosine "C", guanine "G", thymine "T") or purine or pyrimidine bases present in RNA (adenine "A", cytosine "C", guanine "G", uracil "U"). The double-stranded RNA nucleic acid molecules provided herein may also comprise a "T" base at the 3' end, even if the "T" base is not naturally present in an RNA. In some cases, these bases may be denoted as "dT" to distinguish deoxyribonucleotides present in the ribonucleotide chain.

When a nucleic acid molecule selectively reduces or inhibits the expression of a gene, the gene is "targeted" by the nucleic acid molecule described herein. Alternatively, when a nucleic acid molecule hybridizes under stringent conditions to a transcript of a gene (i.e., mRNA thereof), the nucleic acid molecule targets the gene. Being capable of hybridizing "under stringent conditions" means annealing to the target mRNA region under standard conditions that tend to be detrimental to hybridization, e.g., high temperature and/or low salt content. Suitable processes, including 0.1× SSC, 68° C., 2 hours, are described in Molecular Cloning: A Laboratory Manual, Cold Spring Harbor Laboratory, 1982.

As used herein, "CKIP-1" refers to the CKIP-1 gene or protein (also known as PLEKHO1). Examples of the sequences of CKIP-1 include, but are not limited to: human: Genbank number NM_016274.4; mouse: Genbank number NM_023320.2; rat: Genbank number NM_001025119.1 and cynomolgus monkey: Genbank numbers XM001098879 and XM001098774.

As used herein, "target sequence" refers to a contiguous portion of the nucleotide sequence of an mRNA molecule formed during transcription of a CKIP-1 gene, including mRNA as an RNA processing product of a primary transcript.

As used herein and unless otherwise indicated, the term "complementary", when used to describe a relationship between a first nucleotide sequence and a second nucleotide sequence, refers to the ability of an oligonucleotide or polynucleotide comprising the first nucleotide sequence to hybridize under specific conditions to an oligonucleotide or polynucleotide comprising the second nucleotide sequence and form a duplex structure, as will be understood by those skilled in the art. For example, such conditions can be stringent conditions, wherein the stringent conditions can include: 400 mM NaCl, 40 mM PIPES pH 6.4, 1 mM EDTA at 50° C. or 70° C. for 12-16 hours followed by washing. Other conditions may also be used, such as physiologically relevant conditions that may be encountered in an organism. Those skilled in the art will be able to determine the set of conditions most appropriate for a test of complementarity of two sequences in accordance with the ultimate application of the hybridized nucleotides.

This includes base pairing of an oligonucleotide or polynucleotide comprising the first nucleotide sequence with an oligonucleotide or polynucleotide comprising the second nucleotide sequence over the full length of the first and second nucleotide sequences. These sequences may be referred to herein as being "completely complementary" to each other. However, when reference is made herein to the first sequence being "substantially complementary" to the second sequence, the two sequences may be completely complementary or form one or more, but typically no more than 4, 3 or 2, mismatched base pairs upon hybridization, while retaining the ability to hybridize under the conditions most relevant to their ultimate application. However, when two oligonucleotides are designed to form one or more single stranded overhangs upon hybridization, such overhangs should not be considered mismatches when referring to the definition of complementarity. For example, in a dsRNA comprising one oligonucleotide of 19 nucleotides in length and another oligonucleotide of 21 nucleotides in length, the longer oligonucleotide comprises a sequence of 19 nucleotides that is fully complementary to the shorter oligonucleotide, which may also be referred to as being "completely complementary".

"Complementary" sequences, as used herein, may also comprise or be entirely formed from non-Watson-Crick base pairs and/or base pairs formed from non-natural and modified nucleotides, as long as the above requirements regarding their ability to hybridize are met. These non-Watson-Crick base pairs include, but are not limited to, G:U Wobble or Hoogstein base pairing.

As used herein for base matching between the sense strand and the antisense strand of a dsRNA, or base matching between the antisense strand of a dsRNA and the target sequence, the terms "complementary", "fully complementary" and "substantially complementary" may be used, which are to be understood in accordance with the context.

As used herein, a polynucleotide that is "substantially complementary to at least a portion of" a messenger RNA (mRNA) refers to a polynucleotide that is substantially complementary to a contiguous portion of a target mRNA (e.g., an mRNA encoding CKIP-1) that includes a 5' UTR, an open reading frame (ORF), or a 3' UTR. For example, a polynucleotide is complementary to at least a portion of CKIP-1 if its sequence is substantially complementary to a non-interrupted portion of an mRNA encoding CKIP-1.

Recently, it has been found that double-stranded RNA molecules (dsRNA) block gene expression through a highly conserved regulatory mechanism known as RNA interference (RNAi). WO 99/32619 (Fire et al.) discloses the use of dsRNA of at least 25 nucleotides in length to inhibit *C. elegans* gene expression. dsRNA has also been found to degrade target RNA in other organisms including plants (see, e.g., WO 99/53050, Waterhouse et al., and WO 99/61631, Heifetz et al.), *Drosophila* (see, e.g., Yang, D., et al., Curr. Biol. (2000) 10: 1191-1200), and mammals (see WO 00/44895, Limmer and DE 10100586.5, Kreutzer et al.). This natural mechanism has become a hot spot in the development of new drugs for the treatment of diseases caused by abnormal or harmful regulation of genes.

As used herein, the term "double-stranded RNA" or "dsRNA" refers to a duplex structure comprising two antiparallel and substantially complementary nucleic acid strands as described above. Typically, the majority of the nucleotides of each strand are ribonucleotides, but as detailed herein, each strand or both strands may also comprise at least one non-ribonucleotide, such as a deoxyribonucleotide and/or a modified nucleotide. In addition, "dsRNA" as used in this specification may include chemical modifications to ribonucleotides, including modifications at multiple nucleotides, and includes all types of modifications disclosed herein or known in the art.

The two strands forming the duplex structure may be different portions of the same larger RNA molecule, or they may be separate RNA molecules. If the two strands are separate RNA molecules, such dsRNA is often referred to in the literature as siRNA ("short interfering RNA"). If the two strands are parts of a larger molecule and are joined by a non-interrupted nucleotide strand between the 3'-end of one strand and the 5'-end of the other strand forming the duplex structure, the joined RNA strand is referred to as a "hairpin loop", a "short hairpin RNA", or a "shRNA". If the two strands are covalently linked by means other than a non-interrupted strand between the 3'-end of one strand and the 5'-end of the other strand forming a duplex structure, the linkage structure is referred to as a "linker". The RNA strands may have the same or different number of nucleotides. In addition to the duplex structure, the dsRNA may comprise overhangs of one or more nucleotides. Typically, most of the nucleotides of each strand are ribonucleotides, but as described in detail herein, each strand or both strands may also comprise at least one non-ribonucleotide, for example, a deoxyribonucleotide and/or a modified nucleotide.

As used herein, "overhang" refers to one or more unpaired nucleotides that protrude from the duplex structure of a dsRNA when the 3' end of one strand of the dsRNA extends beyond the 5' end of the other strand or vice versa. "Blunt end" or "blunt-ended" means that there are no unpaired nucleotides at the end of the dsRNA, i.e., there are no nucleotide overhangs. A "blunt-ended" dsRNA refers to a dsRNA that is double-stranded over its entire length, i.e., without nucleotide overhang at either end of the molecule. For clarity, chemical caps or non-nucleotide chemical moieties coupled to the 3'- or 5'-ends of the dsRNA are not considered in determining whether the dsRNA has overhangs or blunt ends.

The term "antisense strand" refers to a strand of dsRNA comprising a region substantially complementary to a target sequence. As used herein, the term "complementary region" refers to a region of the antisense strand that is substantially complementary to a sequence as defined herein (e.g., a target sequence). If the complementary region is not fully complementary to the target sequence, the mismatch may be located in an internal or end region of the molecule. Typically, the most tolerable mismatch is located within the terminal regions (excluding overhangs described herein), e.g., within 6, 5, 4, 3 or 2 nucleotides from the 5' and/or 3' ends, or the last 1 nucleotide at the 5' and/or 3' ends.

As used herein, the term "sense strand" refers to a strand of dsRNA comprising a region substantially complementary to the region of the antisense strand.

The term "subject" or "individual" as used herein means a mammal, particularly a primate, particularly a human.

As used herein, "treating" an individual suffering from a disease or disease condition means that the individual's symptoms are partially or completely alleviated, or remain unchanged after treatment. Thus, treatment includes prevention, treatment and/or cure. Prevention refers to prevention of a potential disease and/or prevention of worsening of symptoms or disease progression. Treatment also includes any pharmaceutical uses of any dsRNA, expression vector, and composition provided herein.

As used herein, "therapeutic effect" means an effect resulting from treatment of an individual that alters, generally ameliorates or alleviates the symptoms of the disease or disease condition, or cures the disease or disease condition.

As used herein, "therapeutically effective amount" or "therapeutically effective dose" refers to an amount of a substance, compound, material, or composition comprising a compound that is at least sufficient to produce a therapeutic effect after administration to a subject. Thus, it is the amount necessary to prevent, cure, ameliorate, arrest or partially arrest the symptoms of the disease or condition. For example, if a given clinical treatment that decreases a measurable parameter associated with a disease or condition by at least 25% is considered to be an effective treatment, a therapeutically effective amount of the drug used to treat the disease or condition is the amount necessary to decrease the parameter by at least 25%.

The term "pharmaceutically acceptable carrier" refers to a carrier used to administer a therapeutic agent (e.g., dsRNA). Such carriers include, but are not limited to, saline, buffered saline solution, glucose, water, glycerol, ethanol, and combinations thereof.

As used herein, an "expression vector" includes a vector capable of expressing a nucleotide sequence of interest operably linked to regulatory sequences, such as promoter regions, capable of affecting expression of such nucleotide sequence. Such additional fragments may include promoter and terminator sequences, and optionally may include one or more origins of replication, one or more selectable markers, enhancers, polyadenylation signals, and the like.

As used herein, "operably linked" with respect to a nucleic acid sequence, region, element, or domain means that the nucleic acid regions are functionally related to each other. For example, a promoter may be operably linked to a nucleotide sequence encoding a dsRNA such that the promoter regulates or mediates transcription of the nucleotide sequence.

II. Nucleic Acid Molecules Targeting CKIP-1

The present inventors designed, synthesized and screened out dsRNA molecules capable of significantly inhibiting CKIP-1 expression. Surprisingly, the dsRNA molecules as obtained can both reduce inflammation and promote bone repair, and thus can be effectively used for treating arthritis, such as rheumatoid arthritis (RA).

In one aspect, the invention provides a nucleic acid molecule targeting CKIP-1, such as a dsRNA molecule, which comprises a sense strand and a corresponding complementary antisense strand selected from Table 1.

In some preferred embodiments, the CKIP-1-targeting nucleic acid molecule comprises a sense and an antisense strand corresponding to si-TD060, si-TD062, si-TD066, si-TD068, si-TD070, si-TD074, si-TD080, si-TD082, si-TD089, si-TD096, si-TD137, si-TD140, si-TD141, si-TD143, si-TD176, si-TD178, si-TD181, si-TD362, si-TD364, si-TD378, si-TD726, si-TD730, si-7, si-10 in Table 1.

In some more preferred embodiments, the nucleic acid molecule targeting CKIP-1 comprises a sense strand and an antisense strand corresponding to si-TD137, si-TD141, si-TD176, si-7 in Table 1.

In some embodiments, the sense strand and/or the antisense strand of the nucleic acid molecule additionally has an overhang of at least one nucleotide at the 3' end. For example, the sense and/or antisense strand additionally has an overhang of 1, 2 or 3 nucleotides at the 3' end.

For example, in some embodiments, the overhang is TT (i.e., dTdT). In some embodiments, the sense and antisense strands of the nucleic acid molecule comprise an additional overhang TT at the 3' end.

In some embodiments, the sense strand and/or the antisense strand in the nucleic acid molecule comprises at least 1, e.g., 1 or 2 nucleotide substitutions. For example, the substitution is located within 6, 5, 4, 3 or 2 nucleotides from the 5' and/or 3' ends. In some embodiments, the sense and antisense strands of the nucleic acid molecule comprise 1 nucleotide substitution at the 3' last nucleotide position of the sense strand and correspondingly at the 5' first nucleotide position of the antisense strand. Such substitutions may result in mismatches with the target sequence, however mismatches as defined herein are tolerated, without significantly affecting or without affecting the activity of the dsRNA.

In some embodiments, the dsRNA of the present invention comprises at least one modified nucleotide. The modified nucleotide may comprise modification of the phosphate group, the ribose group and/or the base group.

For example, modification of the phosphate group in a nucleotide includes modification of the oxygen in the phosphate group, such as phosphorothioate modification and boranophosphate modification. The oxygen in the phosphate group is substituted with sulfur and borane, respectively, as shown in the following formula. Both modifications stabilize the nucleic acid structure and maintain high specificity and affinity for base pairing.

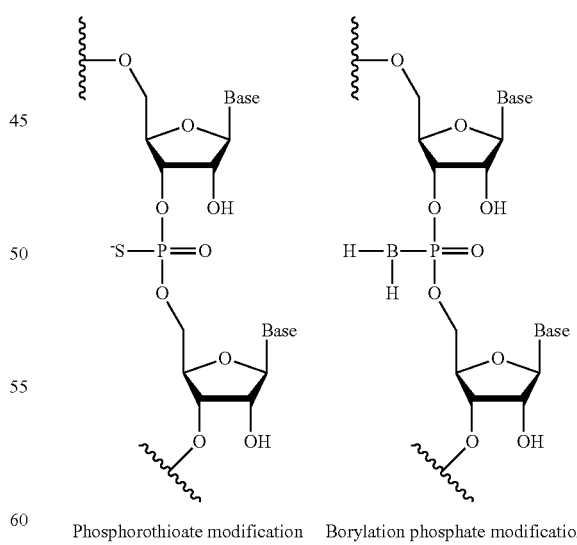

Phosphorothioate modification    Borylation phosphate modification

Modification of the ribose group in a nucleotide includes modification of the 2'-hydroxyl group (2'-OH) in the ribose group. During RNA hydrolysis, under the catalysis of RNase, 2'-OH first attacks the phosphate group, forms a cyclic phosphodiester while breaking a phosphate ester bond, and then forms the hydrolysates under the action of alkali. If certain substituents such as methoxy group or fluorine group are introduced into the 2'-hydroxyl position of the ribose group, the nucleic acid such as siRNA may have stronger nuclease hydrolysis resistance, and the stability of the nucleic acid is improved. Modifications to the 2'-hydroxyl group of the nucleotide pentose include, but are not limited to, 2'-fluoro modification, 2'-methoxy modification (2'-OME), 2'-methoxyethyl modification (2'-MOE), 2'-2,4-dinitrophenol modification (2'-DNP modification), Locked nucleic acid modification (LNA modification), 2'-Amino modification, 2'-Deoxy modification, 3'-Cholesterol modification, 4'-thiothymidine modification, and the like. Examples of structures for such modifications are as follows:

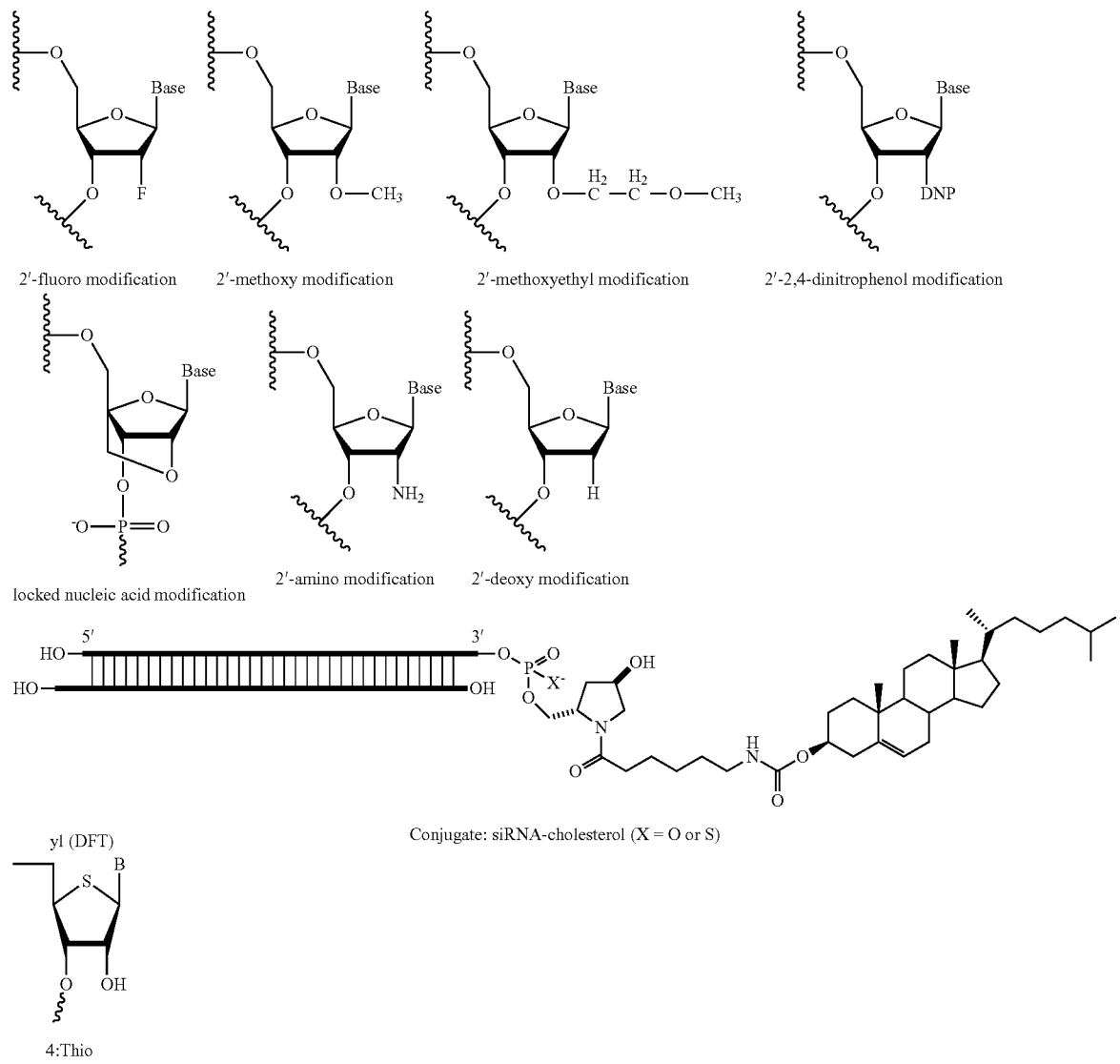

The modification of the base group in the nucleotide refers to modifying the base in the nucleotide group to enhance the interaction between bases, so as to improve the effect on the target mRNA. For example, 5'-bromouracil and 5'-iodouracil modifications, which introduce bromine or iodine at the 5' position of uracil, are commonly used base modifications. Other modifications include N3-methyl-uracil modification, 2,6-diaminopurine modification, etc.

In some embodiments, the dsRNA of the present invention comprises at least one modified nucleotide selected from the group consisting of: 2'-O-methyl modified nucleotides, 2'-F modified nucleotides, nucleotides comprising a 5'-phosphorothioate group, and end nucleotides linked to a cholesteryl derivative or dodecanoic acid bisdecylamide group, and/or, for example, the modified nucleotides are selected from the group consisting of: 2'-deoxy-2'-fluoro modified nucleotides, 2'-deoxy-modified nucleotides, locked nucleotides, abasic nucleotides, 2'-amino-modified nucleotides, 2'-alkyl-modified nucleotides, morpholino nucleotides, phosphoramidates, and nucleotides containing unnatural bases. The at least one modified nucleotide may, for example, enhance the stability of the dsRNA and/or reduce the immunogenic effect of the dsRNA. The modified nucleotides may be on the sense strand and/or on the antisense strand.

In some embodiments, the dsRNA comprises at least one 2'-O-methyl modified ribonucleotide and/or at least one nucleotide comprising a 5'-phosphorothioate group.

In some specific embodiments, the 2' hydroxyl groups of all nucleotides with uracil or cytosine bases in the sense and/or antisense strands of the dsRNA of the present invention are modified with methoxy groups.

In some embodiments, the 2' hydroxyl groups of all nucleotides with uracil or cytosine bases in the sense strand of the dsRNA of the present invention are modified with methoxy groups.

In some embodiments, the 2' hydroxyl groups of all nucleotides in the sense and/or antisense strands of the dsRNA of the present invention are modified with methoxy groups.

In some embodiments, the 2' hydroxyl groups of all nucleotides in the sense strand of the dsRNA of the invention are modified with methoxy groups.

In some embodiments, the 5' end of the sense strand and/or the antisense strand of the dsRNA of the invention is phosphorylated.

In some embodiments, the sense strand and/or the antisense strand of the dsRNA of the present invention comprises a 3' cholesterol modification.

In some embodiments, the 2' hydroxyl groups of all the nucleotides with uracil bases or cytosine bases in the sense strand of the dsRNA of the present invention are modified with fluorine (F).

In some embodiments, the dsRNA of the invention comprises a locked nucleic acid modification in the sense strand.

In some embodiments, all nucleotides in the sense strand and/or antisense strand of the dsRNA of the invention comprise phosphorothioate modifications.

In some embodiments, the dsRNA molecule is an siRNA.

In still other embodiments, the dsRNA molecule is shRNA (short hairpin RNA). It is within the ability of those skilled in the art to design suitable shRNAs based on siRNA sequences.

The dsRNA of the present invention may be obtained by conventional techniques in the art such as solid phase synthesis or liquid phase synthesis. Modified nucleotides can be introduced by using modified nucleotide monomers during the synthesis.

In yet another aspect, the invention provides an expression vector comprising a nucleotide sequence encoding a nucleic acid molecule of the invention, such as dsRNA, wherein the nucleotide sequence is operably linked to a transcription regulatory element, such as a promoter or the like. Recombinant vector capable of expressing a dsRNA molecule can be delivered to and permanently present in the target cells. Alternatively, a vector providing transient expression of the nucleic acid molecule may be used. If desired, the vector may be administered repeatedly. Once expressed, the dsRNA molecule interacts with the target mRNA and generates an RNA interference response. In general, shRNAs are particularly suitable for being produced in this manner.

The expression vector may be a linear construct, a circular plasmid vector, or a viral vector (including but not limited to adenovirus, adeno-associated virus, lentiviral vector, etc.). In the case of siRNA, individual strands of siRNA can be transcribed from promoters on two separate expression vectors; alternatively, individual strands of siRNA may be transcribed from promoters both located on the same expression plasmid. In the case of shRNA, the shRNA strand is transcribed from a single expression vector.

The promoter driving dsRNA expression in the expression vector of the present invention may be eukaryotic RNA polymerase I promoter (e.g., ribosomal RNA promoter), RNA polymerase II promoter (e.g., CMV early promoter or actin promoter or U1snRNA promoter) or generally RNA polymerase III promoter (e.g., U6snRNA or 7SKRNA promoter) or prokaryotic promoter (e.g., T7 promoter, provided that the expression vector also encodes the T7 RNA polymerase required for transcription from the T7 promoter).

The dsRNA of the present invention can significantly inhibit the expression of CKIP-1 in cells. In some embodiments, expression of CKIP-1 is inhibited by at least 50%, at least 55%, at least 60%, at least 65%, at least 70%, at least 75%, at least 80%, at least 85%, at least 90%, at least 95%, or even 100%. Preferably, the dsRNA of the present invention is capable of inhibiting CKIP-1 expression by at least 50%. More preferably, the dsRNA of the present invention is capable of inhibiting CKIP-1 expression by at least 70%.

When the terms "inhibit the expression of", "downregulate the expression of", "suppress the expression of", and the like are used in reference to a CKIP-1 gene, they refer herein to the at least partial inhibition of the expression of the CKIIP-1 gene, as manifested by a decrease in the level of CKIP-1 expression in a first cell or group of cells in which the CKIP-1 gene is transcribed and which has or have been treated such that the expression of the CKIIP-1 gene is inhibited, as compared to a second cell or group of cells substantially identical to the first cell or group of cells but which has or have not been so treated (control cells). The degree of inhibition is usually expressed in the following way:

(CKISP-1 expression level in control cells—CKP-1 expression level in treated cells) CKIP-1 expression level in control cells×10000.

The expression level may be an mRNA level or a protein level. It is clear to those skilled in the art how to determine the mRNA level or the corresponding protein level of a particular gene.

Surprisingly, the dsRNA of the present invention may also inhibit the expression of the pro-inflammatory cytokines IL-6, TNF-αL and/or IL-17A. In particular, the dsRNA of the present invention can significantly inhibit the expression of the pro-inflammatory cytokine IL-6.

In some embodiments, expression of the pro-inflammatory cytokines IL-6, TNF-αL, and/or IL-17A is inhibited by at least 10%, at least 20%, at least 30%, at least 40%, at least 50%, at least 60%, at least 7000, at least 80%, at least 90%, or even 100%. In some preferred embodiments, the expression of IL-6 is inhibited by at least 50%, more preferably by at least 80%.

TABLE 1 dsRNA inhibiting CKIP-1 expression

| SIRNA | | Sequence (5'-3') | SEQ ID NO |
|---|---|---|---|
| si-TD037 | Sense strand | AAGGUCGGCUGGGUCCGGA | 1 |
| | Antisense strand | UCCGGACCCAGCCGACCUU | 2 |
| si-TD040 | Sense strand | GUCGGCUGGGUCCGGAAAU | 3 |
| | Antisense strand | AUUUCCGGACCCAGCCGAC | 4 |
| si-TD042 | Sense strand | CGGCUGGGUCCGGAAAUUC | 5 |
| | Antisense strand | GAAUUUCCGGACCCAGCCG | 6 |
| si-TD044 | Sense strand | GCUGGGUCCGGAAAUUCUG | 7 |
| | Antisense strand | CAGAAUUUCCGGACCCAGC | 8 |
| si-TD050 | Sense strand | UCCGGAAAUUCUGCGGGAA | 9 |
| | Antisense strand | UUCCCGCAGAAUUUCCGGA | 10 |
| si-TD057 | Sense strand | AUUCUGCGGGAAAGGGAUU | 11 |
| | Antisense strand | AAUCCCUUUCCCGCAGAAU | 12 |
| si-TD058 | Sense strand | UUCUGCGGGAAAGGGAUUU | 13 |
| | Antisense strand | AAAUCCCUUUCCCGCAGAA | 14 |
| si-TD060 | Sense strand | CUGCGGGAAAGGGAUUUUC | 15 |
| | Antisense strand | GAAAAUCCCUUUCCCGCAG | 16 |
| si-TD061 | Sense strand | UGCGGGAAAGGGAUUUUCA | 17 |
| | Antisense strand | UGAAAAUCCCUUUCCCGCA | 18 |
| si-TD062 | Sense strand | GCGGGAAAGGGAUUUUCAG | 19 |
| | Antisense strand | CUGAAAAUCCCUUUCCCGC | 20 |
| si-TD064 | Sense strand | GGGAAAGGGAUUUUCAGGG | 21 |
| | Antisense strand | CCCUGAAAAUCCCUUUCCC | 22 |
| si-TD065 | Sense strand | GGAAAGGGAUUUUCAGGGA | 23 |
| | Antisense strand | UCCCUGAAAAUCCCUUUCC | 24 |
| si-TD066 | Sense strand | GAAAGGGAUUUUCAGGGAG | 25 |
| | Antisense strand | CUCCCUGAAAAUCCCUUUC | 26 |
| si-TD067 | Sense strand | AAAGGGAUUUUCAGGGAGA | 27 |
| | Antisense strand | UCUCCCUGAAAAUCCCUUU | 28 |
| si-TD068 | Sense strand | AAGGGAUUUUCAGGGAGAU | 29 |
| | Antisense strand | AUCUCCCUGAAAAUCCCUU | 30 |
| si-TD070 | Sense strand | GGGAUUUUCAGGGAGAUUU | 31 |
| | Antisense strand | AAAUCUCCCUGAAAAUCCC | 32 |
| si-TD072 | Sense strand | GAUUUUCAGGGAGAUUUGG | 33 |
| | Antisense strand | CCAAAUCUCCCUGAAAAUC | 34 |
| si-TD074 | Sense strand | UUUUCAGGGAGAUUUGGAA | 35 |
| | Antisense strand | UUCCAAAUCUCCCUGAAAA | 36 |
| si-TD076 | Sense strand | UUCAGGGAGAUUUGGAAAA | 37 |
| | Antisense strand | UUUUCCAAAUCUCCCUGAA | 38 |
| si-TD078 | Sense strand | CAGGGAGAUUUGGAAAAAC | 39 |
| | Antisense strand | GUUUUCCAAAUCUCCCUG | 40 |
| si-TD080 | Sense strand | GGGAGAUUUGGAAAAACCG | 41 |
| | Antisense strand | CGGUUUUUCCAAAUCUCCC | 42 |
| si-TD082 | Sense strand | GAGAUUUGGAAAAACCGCU | 43 |
| | Antisense strand | AGCGGUUUUUCCAAAUCUC | 44 |
| si-TD084 | Sense strand | GAUUUGGAAAAACCGCUAU | 45 |
| | Antisense strand | AUAGCGGUUUUUCCAAAUC | 46 |
| si-TD087 | Sense strand | UUGGAAAAACCGCUAUGUG | 47 |
| | Antisense strand | CACAUAGCGGUUUUUCCAA | 48 |
| si-TD089 | Sense strand | GGAAAAACCGCUAUGUGGU | 49 |
| | Antisense strand | ACCACAUAGCGGUUUUUCC | 50 |

TABLE 1-continued dsRNA inhibiting CKIP-1 expression

| SIRNA | | Sequence (5'-3') | SEQ ID NO |
|---|---|---|---|
| si-TD093 | Sense strand | AAACCGCUAUGUGGUGCUG | 51 |
| | Antisense strand | CAGCACCACAUAGCGGUUU | 52 |
| si-TD094 | Sense strand | AACCGCUAUGUGGUGCUGA | 53 |
| | Antisense strand | UCAGCACCACAUAGCGGUU | 54 |
| si-TD096 | Sense strand | CCGCUAUGUGGUGCUGAAA | 55 |
| | Antisense strand | UUUCAGCACCACAUAGCGG | 56 |
| si-TD097 | Sense strand | CGCUAUGUGGUGCUGAAAG | 57 |
| | Antisense strand | CUUUCAGCACCACAUAGCG | 58 |
| si-TD098 | Sense strand | GCUAUGUGGUGCUGAAAGG | 59 |
| | Antisense strand | CCUUUCAGCACCACAUAGC | 60 |
| si-TD136 | Sense strand | GAGAAGGAGGUAAAAGAUG | 61 |
| | Antisense strand | CAUCUUUUACCUCCUUCUC | 62 |
| si-TD137 | Sense strand | AGAAGGAGGUAAAAGAUGA | 63 |
| | Antisense strand | UCAUCUUUUACCUCCUUCU | 64 |
| si-TD138 | Sense strand | GAAGGAGGUAAAAGAUGAG | 65 |
| | Antisense strand | CUCAUCUUUUACCUCCUUC | 66 |
| si-TD139 | Sense strand | AAGGAGGUAAAAGAUGAGA | 67 |
| | Antisense strand | UCUCAUCUUUUACCUCCUU | 68 |
| si-TD140 | Sense strand | AGGAGGUAAAAGAUGAGAA | 69 |
| | Antisense strand | UUCUCAUCUUUUACCUCCU | 70 |
| si-TD141 | Sense strand | GGAGGUAAAAGAUGAGAAA | 71 |
| | Antisense strand | UUUCUCAUCUUUUACCUCC | 72 |
| si-TD143 | Sense strand | AGGUAAAAGAUGAGAAAAA | 73 |
| | Antisense strand | UUUUUCUCAUCUUUUACCU | 74 |
| si-TD181 | Sense strand | CUGAGUGACUAUGAGAAGU | 75 |
| | Antisense strand | ACUUCUCAUAGUCACUCAG | 76 |
| si-TD179 | Sense strand | ACCUGAGUGACUAUGAGAA | 77 |
| | Antisense strand | UUCUCAUAGUCACUCAGGU | 78 |
| si-TD178 | Sense strand | GACCUGAGUGACUAUGAGA | 79 |
| | Antisense strand | UCUCAUAGUCACUCAGGUC | 80 |
| si-TD177 | Sense strand | UGACCUGAGUGACUAUGAG | 81 |
| | Antisense strand | CUCAUAGUCACUCAGGUCA | 82 |
| si-TD176 | Sense strand | UUGACCUGAGUGACUAUGA | 83 |
| | Antisense strand | UCAUAGUCACUCAGGUCAA | 84 |
| si-TD224 | Sense strand | GCAGGAGCAAGAAAAAUCA | 85 |
| | Antisense strand | UGAUUUUUCUUGCUCCUGC | 86 |
| si-TD221 | Sense strand | AGAGCAGGAGCAAGAAAAA | 87 |
| | Antisense strand | UUUUUCUUGCUCCUGCUCU | 88 |
| si-TD217 | Sense strand | UCCAAGAGCAGGAGCAAGA | 89 |
| | Antisense strand | UCUUGCUCCUGCUCUUGGA | 90 |
| si-TD380 | Sense strand | UGAGGAGGACAGCUAUCUU | 91 |
| | Antisense strand | AAGAUAGCUGUCCUCCUCA | 92 |
| si-TD378 | Sense strand | GUUGAGGAGGACAGCUAUC | 93 |
| | Antisense strand | GAUAGCUGUCCUCCUCAAC | 94 |
| si-TD376 | Sense strand | CCGUUGAGGAGGACAGCUA | 95 |
| | Antisense strand | UAGCUGUCCUCCUCAACGG | 96 |
| si-TD372 | Sense strand | GUCACCGUUGAGGAGGACA | 97 |
| | Antisense strand | UGUCCUCCUCAACGGUGAC | 98 |
| si-TD370 | Sense strand | AGGUCACCGUUGAGGAGGA | 99 |
| | Antisense strand | UCCUCCUCAACGGUGACCU | 100 |

TABLE 1-continued dsRNA inhibiting CKIP-1 expression

| SIRNA | | Sequence (5'-3') | SEQ ID NO |
|---|---|---|---|
| si-TD364 | Sense strand | UGGAUGAGGUCACCGUUGA | 101 |
| | Antisense strand | UCAACGGUGACCUCAUCCA | 102 |
| si-TD362 | Sense strand | CUUGGAUGAGGUCACCGUU | 103 |
| | Antisense strand | AACGGUGACCUCAUCCAAG | 104 |
| si-TD358 | Sense strand | GUAUCUUGGAUGAGGUCAC | 105 |
| | Antisense strand | GUGACCUCAUCCAAGAUAC | 106 |
| si-TD451 | Sense strand | AGGAAGACCCUUCCCCUGA | 107 |
| | Antisense strand | UCAGGGGAAGGGUCUUCCU | 108 |
| si-TD443 | Sense strand | GAUCCAAGAGGAAGACCCU | 109 |
| | Antisense strand | AGGGUCUUCCUCUUGGAUC | 110 |
| si-TD509 | Sense strand | GGACAAGUCUGUGGCCCAG | 111 |
| | Antisense strand | CUGGGCCACAGACUUGUCC | 112 |
| si-TD508 | Sense strand | UGGACAAGUCUGUGGCCCA | 113 |
| | Antisense strand | UGGGCCACAGACUUGUCCA | 114 |
| si-TD577 | Sense strand | GCCUCCCUGGAGGAGAUCC | 115 |
| | Antisense strand | GGAUCUCCUCCAGGGAGGC | 116 |
| si-TD611 | Sense strand | GGUAGCAAGGAAACUGGAG | 117 |
| | Antisense strand | CUCCAGUUUCCUUGCUACC | 118 |
| si-TD609 | Sense strand | CUGGUAGCAAGGAAACUGG | 119 |
| | Antisense strand | CCAGUUUCCUUGCUACCAG | 120 |
| si-TD607 | Sense strand | ACCUGGUAGCAAGGAAACU | 121 |
| | Antisense strand | AGUUUCCUUGCUACCAGGU | 122 |
| si-TD604 | Sense strand | AGGACCUGGUAGCAAGGAA | 123 |
| | Antisense strand | UUCCUUGCUACCAGGUCCU | 124 |
| si-TD600 | Sense strand | AUCCAGGACCUGGUAGCAA | 125 |
| | Antisense strand | UUGCUACCAGGUCCUGGAU | 126 |
| si-TD598 | Sense strand | GGAUCCAGGACCUGGUAGC | 127 |
| | Antisense strand | GCUACCAGGUCCUGGAUCC | 128 |
| si-TD596 | Sense strand | CCGGAUCCAGGACCUGGUA | 129 |
| | Antisense strand | UACCAGGUCCUGGAUCCGG | 130 |
| si-TD588 | Sense strand | CAGCUGUCCCGGAUCCAGG | 131 |
| | Antisense strand | CCUGGAUCCGGGACAGCUG | 132 |
| si-TD587 | Sense strand | GCAGCUGUCCCGGAUCCAG | 133 |
| | Antisense strand | CUGGAUCCGGGACAGCUGC | 134 |
| si-TD585 | Sense strand | GGGCAGCUGUCCCGGAUCC | 135 |
| | Antisense strand | GGAUCCGGGACAGCUGCCC | 136 |
| si-TD720 | Sense strand | GAGCUGAGAGACCUGUACA | 137 |
| | Antisense strand | UGUACAGGUCUCUCAGCUC | 138 |
| si-TD718 | Sense strand | GGGAGCUGAGAGACCUGUA | 139 |
| | Antisense strand | UACAGGUCUCUCAGCUCCC | 140 |
| si-TD743 | Sense strand | GACUCCCACCUCAGACAGA | 141 |
| | Antisense strand | UCUGUCUGAGGUGGGAGUC | 142 |
| si-TD145 | Sense strand | GUAAAGAUGAGAAAAAUA | 143 |
| | Antisense strand | UAUUUUUCUCAUCUUUUAC | 144 |
| si-TD480 | Sense strand | UCUUGUGCUGAGAGCUUUC | 145 |
| | Antisense strand | GAAAGCUCUCAGCACAAGA | 146 |
| si-TD483 | Sense strand | UGUGCUGAGAGCUUUCGGG | 147 |
| | Antisense strand | CCCGAAAGCUCUCAGCACA | 148 |
| si-TD736 | Sense strand | ACAGACAGGUGGACCUGCA | 149 |
| | Antisense strand | UGCAGGUCCAUCUGUCUGU | 150 |
| si-TD734 | Sense strand | GUACAGACAGAUGGACCUG | 151 |
| | Antisense strand | CAGGUCCAUCUGUCUGUAC | 152 |
| si-TD730 | Sense strand | ACCUGUACAGACAGAUGGA | 153 |
| | Antisense strand | UCCAUCUGUCUGUACAGGU | 154 |
| si-TD726 | Sense strand | AGAGACCUGUACAGACAGA | 155 |
| | Antisense strand | UCUGUCUGUACAGGUCUCU | 156 |
| si-TD723 | Sense strand | CUGAGAGACCUGUACAGAC | 157 |
| | Antisense strand | GUCUGUACAGGUCUCUCAG | 158 |
| si-TD717 | Sense strand | AGGGAGCUGAGAGACCUGU | 159 |
| | Antisense strand | ACAGGUCUCUCAGCUCCCU | 160 |
| si-7 | Sense strand | UGGGAGAUGGGAAGCGAAA | 161 |
| | Antisense strand | UUUCGCUUCCCAUCUCCCA | 162 |
| si-10 | Sense strand | CAGACAAAGGGGCCACCUA | 163 |
| | Antisense strand | UAGGUGGCCCCUUUGUCUG | 164 |
| si-1 | Sense strand | GGACCUGGUAGCAAGGAAA | 165 |
| | Antisense strand | UUUCCUUGCUACCAGGUCC | 166 |

III. Pharmaceutical Compositions

In yet another aspect, the present invention provides a pharmaceutical composition comprising at least one dsRNA of the present invention or expression vector comprising a nucleotide sequence encoding the dsRNA, and a pharmaceutically acceptable carrier. In some embodiments, the pharmaceutical compositions are used for treating inflammatory diseases, such as arthritis, particularly rheumatoid arthritis (RA).

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal, intraarticular or epidermal administration (e.g., by injection or infusion). Depending on the route of administration, the active compound, i.e., the dsRNA molecule, can be encapsulated in a material, such as a liposome, to protect the compound from acids and other natural conditions that inactivate the compound. In some embodiments, the dsRNA of the present invention may be delivered by a cationic liposome delivery system.

The pharmaceutical compositions of the present invention may also contain pharmaceutically acceptable antioxidants. Examples of pharmaceutically acceptable antioxidants include: (1) Water-soluble antioxidants such as ascorbic acid, cysteine hydrochloride, sodium bisulfate, sodium metabisulfite, sodium sulfite and the like; (2) Oil-soluble antioxidants such as ascorbyl palmitate, butylated hydroxyanisole (BHA), butylated hydroxytoluene (BHT), lecithin, propyl gallate, α-tocopherol and the like; and (3) metal chelating agents such as citric acid, ethylenediaminetetraacetic acid (EDTA), sorbitol, tartaric acid, phosphoric acid and the like.

Such compositions may also contain, for example, preservatives, wetting agents, emulsifying agents and dispersing agents.

Prevention of the presence of microorganisms can be ensured by sterilization procedures or by the inclusion of various antibacterial and antifungal agents such as parabens, chlorobutanol, phenol sorbic acid, and the like. In many cases, it is preferred to include isotonic agents, for example, sugars, polyalcohols such as mannitol, sorbitol, or sodium oxide in the composition. Prolonged absorption of the injectable pharmaceutical can be realized by adding to the composition of absorption delaying agents, for example, monostearate salts and gelatin.

Pharmaceutically acceptable carriers include sterile aqueous solutions or dispersions and powders for the extemporaneous preparation of sterile injectable solutions or dispersions. The use of such media and agents for pharmaceutically active substances is well known in the art. Conventional media or agents, other than any range incompatible with the active compound, may be present in the pharmaceutical composition of the present invention. Additional active compounds may also be incorporated into the compositions.

Generally, therapeutic compositions must be sterile and stable under the conditions of manufacture and storage. The compositions may be formulated as solutions, microemulsions, liposomes or other ordered structures suitable for high drug concentrations. The carrier can be a solvent or dispersion containing, for example, water, ethanol, polyol (for example, glycerol, propylene glycol, and liquid polyethylene glycol, and the like), and suitable mixtures thereof. Proper fluidity can be maintained, for example, by the use of a coating such as lecithin, by the maintenance of the required particle size in the case of dispersion and by the use of surfactants.

Sterile injectable solutions can be prepared by incorporating the active compound in the required amount in a suitable solvent with one or a combination of ingredients enumerated above, as required, followed by sterile microfiltration. Generally, dispersions are prepared by incorporating the active compound into a sterile carrier which contains a basic dispersion medium and the other required ingredients from those enumerated above. For sterile powders for the preparation of sterile injectable solutions, the preferred methods of preparation are drying under vacuum and freeze-drying (lyophilization) which yields a powder of the active ingredient plus any additional desired ingredient from a previously sterile-filtered solution thereof.

The amount of active ingredient that can be combined with the carrier materials to produce a single dosage form will vary depending upon the subject being treated and the particular mode of administration. The amount of active ingredient that can be combined with the carrier materials to produce a single dosage form will generally be that amount of the composition which produces a therapeutic effect. Typically, this amount ranges from about 0.01% to about 99% active ingredient, e.g., from about 0.1% to about 70%, e.g., from about 1% to about 30% active ingredient, on a 100% basis, in combination with a pharmaceutically acceptable carrier.

The dosage regimen can be adjusted to provide the optimal desired response (e.g., therapeutic response). For example, a single bolus may be administered, several divided doses may be administered over time, or the dose may be proportionally reduced or increased as required by the exigencies of the therapeutic situation. It is particularly advantageous to formulate parenteral compositions in dosage unit form for ease of administration and uniformity of dosage. Dosage unit form as used herein refers to physically discrete units suited as unitary dosages for the subject to be treated; each unit contains a predetermined amount of active compound calculated to produce the desired therapeutic effect in combination with the required pharmaceutical carrier. The specific description of the dosage unit forms of the invention are dictated by and directly dependent on (a) the unique characteristics of the active compound and the particular therapeutic effect to be achieved, and (b) the limitations inherent in the art for formulating such active compounds for the treatment of sensitivity in individuals.

For administration of the dsRNA molecules of the present invention, the dosage may range from about 0.0000001 to 100 mg/kg body weight of the recipient. An exemplary treatment regimen may be once a week, once every two weeks, once every three weeks, once every four weeks, once a month, once every two months, once every three months, once every four months, once every five months, once every six months, once every seven months, once every eight months, once every nine months, once every 10 months, once every 11 months, even once every 12 months, or with a short administration interval at the beginning (such as once per week to once every three weeks), and then an extended interval later (such as once a month to even once every 12 months).

Actual dosage levels of the active ingredients in the pharmaceutical compositions of this invention may be varied so as to obtain an amount of the active ingredient that is effective to achieve the desired therapeutic response for a particular patient, composition, and mode of administration without being toxic to the patient. The selected dosage level will depend upon a variety of pharmacokinetic factors, including the activity of the particular composition of the invention employed, way of administration, the time of administration, the rate of excretion of the particular compound employed, the duration of the treatment, other drugs, compounds and/or materials used in combination with the particular composition employed, the age, sex, weight, condition, general health, and medical history of the patient being treated, and similar factors known in the medical field.

IV. Disease Treatment

The present inventors designed more than 200 siRNA molecules directed against CKIP-1 gene, from which siRNA molecules capable of significantly inhibiting CKIP-1 expression were screened (Examples 1-3). Experiments show that the CKIP-1 targeting molecule of the present invention can significantly inhibit the expression of CKIP-1 protein in human osteoblasts (Example 5), and administration of the dsRNA can promote the expression of phenotypic genes of human osteoblasts, thereby promoting osteoblast differentiation (Examples 6 and 7). In mouse and cynomolgus monkey models, administration of dsRNA of the invention significantly alleviates arthritis progression (Examples 8 and 9).

Even more surprisingly, the present inventors have found that the dsRNA of the present invention is capable of inhibiting the expression of pro-inflammatory cytokines IL-6, TNF-α and/or IL-17A (Examples 4 and 8). In particular, the dsRNA of the present invention can significantly inhibit the expression of the pro-inflammatory cytokine IL-6. TNF-α is mainly expressed by macrophages of inflamed joints, synovial lining cells and activated T cells. In RA inflamed joints, TNF-α is one of the most prominent pro-inflammatory cytokines capable of inducing the production of other pro-inflammatory factors such as IL-1 $, IL-6 and IL-8. IL-6 receptor neutralizing antibodies completely abolish the inflammatory response during the induction of CIA, suggesting that IL-6 plays an important role in the initiation of arthritis.

While previous pharmaceutical studies on CKIP-1 have been focused primarily on inhibiting bone destruction or repairing bone damage, the present invention for the first time discovered that dsRNA targeting CKIP-1 of the present invention can inhibit the expression of pro-inflammatory cytokines, and thus can be used to treat inflammation. The dsRNA targeting CKIP-1 of the present invention capable of inhibiting inflammation is particularly advantageous in the treatment of arthritis, particularly rheumatoid arthritis, because in RA, the main early symptoms are joint inflammation, while bone destruction only occurs after several years (referred to as "late stage bone destruction"). The dsRNA targeting CKIP-1 of the present invention can inhibit inflammation and also repair bone damage, and thus can be advantageously used in various stages of RA treatment, without being limited to late stage bone destruction.

Accordingly, in another aspect, the present invention provides a method of treating arthritis, particularly rheumatoid arthritis, in a subject in need thereof, comprising administering to the subject a therapeutically effective amount of a dsRNA molecule of the present invention or an expression vector of the present invention or a pharmaceutical composition of the present invention.

In yet another aspect, the invention also provides the use of a dsRNA of the invention or an expression vector of the invention or a pharmaceutical composition of the invention in the preparation of a medicament for treating arthritis, particularly rheumatoid arthritis, in a subject in need thereof.

Arthritis that can be treated by the dsRNA molecules of the invention or expression vectors of the invention or pharmaceutical compositions of the invention include, but are not limited to, rheumatoid arthritis, osteoarthritis, idiopathic arthritis, ankylosing spondylitis, psoriatic arthritis, infectious arthritis, Juvenile arthritis, reactive arthritis, gouty arthritis, and the like.

The dsRNA of the invention or the expression vector of the invention or the pharmaceutical composition of the invention may also be used in combination with an additional therapeutic agent for the treatment of arthritis, in particular rheumatoid arthritis. Such additional therapeutic agents include, but are not limited to, non-steroidal anti-inflammatory drugs, hormones, anti-rheumatic drugs, and the like.

In yet another aspect, the invention provides a method of treating an inflammatory disease associated with a pro-inflammatory cytokine (e.g., IL-6, TNF-α and/or IL-17A) in a subject in need thereof, comprising administering to the subject a therapeutically effective amount of a dsRNA molecule of the invention or an expression vector of the invention or a pharmaceutical composition of the invention.

In yet another aspect, the invention also provides the use of a dsRNA of the invention or an expression vector of the invention or a pharmaceutical composition of the invention in the preparation of a medicament for the treatment of an inflammatory disease associated with a pro-inflammatory cytokine (e.g., IL-6, TNF-α and/or IL-17A) in a subject in need thereof.

Inflammatory diseases associated with such pro-inflammatory cytokines (e.g., IL-6, TNF-α, and/or IL-17A) include, but are not limited to, inflammatory bowel disease, inflammation caused by infection, inflammation caused by injury, inflammation of the respiratory system, inflammation associated with cancer, and the like. Inflammatory diseases associated with such pro-inflammatory cytokines (e.g., IL-6, TNF-α and/or IL-17A) also include arthritis, such as those listed above, particularly rheumatoid arthritis.

Other inflammatory diseases associated with pro-inflammatory cytokines (e.g., IL-6, TNF-α, and/or IL-17A) that can be treated by dsRNA molecules of the invention or expression vectors of the invention or pharmaceutical compositions of the invention include, but are not limited to, systemic lupus erythematosus, Crohn's disease, psoriasis, colitis, ileitis, glomerulonephritis, asthma, dermatitis (including contact dermatitis and atopic dermatitis), vasculitis, chronic bronchitis, chronic prostatitis, appendicitis, pancreatitis, pelvic inflammation, polymyositis, chronic obstructive pulmonary disease and the like.

The dsRNA of the invention or the expression vector of the invention or the pharmaceutical composition of the invention may also be used in combination with additional therapeutic agents for the treatment of inflammatory diseases, in particular inflammatory diseases associated with pro-inflammatory cytokines such as IL-6, TNF-α and/or IL-17A. Such additional therapeutic agents are, for example, inhibitors that target TNF-α, including but not limited to Infliximab, Etanercept, Adalimumab, Golimumab, and Certolizumab; IL-6 blockers, including but not limited to, Tocilizumab; IL-17A blockers, including but not limited to Secukinumab.

In yet another aspect, the invention provides a method of treating a bone metabolism-related disorder in a subject in need thereof, comprising administering to the subject a therapeutically effective amount of a dsRNA molecule of the invention or an expression vector of the invention or a pharmaceutical composition of the invention.

In yet another aspect, the invention also provides the use of a dsRNA of the invention or an expression vector of the invention or a pharmaceutical composition of the invention in the preparation of a medicament for a bone metabolism-related disorder in a subject in need thereof.

Such bone metabolism related diseases include, but are not limited to, osteomalacia, bone deficiency, osteolytic bone disease, renal bone disease, osteogenesis imperfecta, bone destruction caused by cancer bone metastases, and the like.

The dsRNA of the present invention or the expression vector of the present invention or the pharmaceutical composition of the present invention may also be used in combination with additional therapeutic agents for the treatment of bone metabolism-related disorder.

In yet another aspect, the invention provides a method of reducing the level of a pro-inflammatory cytokine (e.g., IL-6, TNF-α and/or IL-17A) in a subject in need thereof, comprising administering to the subject a therapeutically effective amount of a dsRNA molecule of the invention or an expression vector of the invention or a pharmaceutical composition of the invention.

Preferably, in the above aspects of the invention, the subject is human.

In some embodiments, the dsRNA of the invention or the expression vector of the invention or the pharmaceutical composition of the invention is administered intra-particularly. In some embodiments, the dsRNA of the invention or the expression vector of the invention or the pharmaceutical composition of the invention is administered systemically.

EXAMPLES

A further understanding of the present invention may be obtained by reference to specific examples set forth herein which are presented for purposes of illustration only and are not intended to limit the scope of the invention in any way. It will be evident that various modifications and changes may be made thereto without departing from the spirit of the invention, and accordingly, such modifications and changes are intended to be within the scope of the appended claims.

Example 1. Sequence Design and Synthesis of siRNA Targeting CKIP-1

Candidate siRNAs were designed according to homologous regions of human CKIP-1 mRNA and monkey CKIP-1 mRNA sequences to obtain a candidate siRNA sequence pool. Off-target effects were comprehensively analyzed for the candidate siRNA sequence pool, and candidate siRNA sequences with high off-target scores were removed. By combining a seed region matching score, 208 siRNA candidate sequences against CKIP-1 were finally obtained and synthesized. Eight unrelated NC sequences were also designed and synthesized as negative controls in the screening assay. The synthesized 208 gene siRNA sequences, as well as 8 NC sequences, are as shown in FIG. 1.

Example 2. Real-time Quantitative PCR Screening for SiRNAs that Inhibit CIKP-1 Expression HFOB cells (human osteoblast strain commercially available from the Chinese Academy of Sciences) were seeded in 96-well cell culture plates, and siRNA transfection was performed at a cell density of about 70%. 0.5 μl of Lipofectamine2000 was diluted in 25 μl of opti-MEM without serum and antibiotics and mixed well. 15 pmol of RNA was diluted in 25 μl of opti-MEM without serum and antibiotics and mixed slightly. The Lipofectamine2000 dilution was added to the RNA dilution and mixed well. It was left at room temperature for 20 min. A mixture of 50 μl Lipofectamine2000 and RNA was added to a 96-well cell plate seeded with cells, slightly shaken to mix well, and the solution was changed after 5 h. RNA was extracted 48 hours later (TIANGEN micro RNA extraction kit), and qPCR detection (TransGen qPCR kit) was performed after reverse transcription (Takara reverse transcription kit). The relative expression of CIKP-1 was determined using GADPH gene as internal reference. The corresponding CIKP-1 relative expression values of the obtained siRNAs were normalized to the blank treatment group. Each NC sequence was also used as a negative control. The primer sequence is as follows:

CIKP1-F: gGAACCAACCTCTTGTGCTG
CIKP1-R: gTCAACTTCTTGGGTGCCTG
GADPH-F: cATGAGAAGTATGACAACAGCCT
GADPH-R: aGTCCTTCCACGATACCAAAGT

The results showed that 82 sequences with an interference efficiency of 50% and above were selected from 208 siRNA sequences (see Table 2), and 22 sequences have an interference efficiency of 70% and above (shown in bold italics in Table 2). These sequences were used as candidates for further screening.

TABLE 2 siRNA with interference efficiency of 50% and above

| SIRNA Sequence | Normalized target gene relative expression value |
|---|---|
| si-TD037 | 0.472339 |
| si-TD040 | 0.457801 |
| si-TD042 | 0.422001 |
| si-TD044 | 0.398672 |
| si-TD050 | 0.307432 |
| si-TD057 | 0.417976 |
| si-TD058 | 0.412397 |
| *si-TD060* | *0.250549* |
| si-TD061 | 0.314191 |
| *si-TD062* | *0.198302* |
| si-TD064 | 0.46957 |
| si-TD065 | 0.4389 |
| *si-TD066* | *0.30317* |
| si-TD067 | 0.411764 |
| *si-TD068* | *0.252114* |
| *si-TD070* | *0.281898* |
| si-TD072 | 0.401834 |
| *si-TD074* | *0.220171* |
| si-TD076 | 0.334746 |
| si-TD078 | 0.318811 |
| *si-TD080* | *0.23612* |
| *si-TD082* | *0.297076* |
| si-TD084 | 0.356374 |
| si-TD087 | 0.32098 |
| *si-TD089* | *0.238577* |
| si-TD093 | 0.367916 |
| si-TD094 | 0.410962 |
| *si-TD096* | *0.17883* |
| si-TD097 | 0.409968 |
| si-TD098 | 0.431926 |
| si-TD136 | 0.356366 |
| *si-TD137* | *0.118522* |
| si-TD138 | 0.387089 |
| si-TD139 | 0.335127 |
| *si-TD140* | *0.235433* |
| *si-TD141* | *0.287318* |
| *si-TD143* | *0.169164* |
| si-TD145 | 0.346415 |
| *si-TD176* | *0.223003* |
| si-TD177 | 0.410735 |
| *si-TD178* | *0.172067* |
| si-TD179 | 0.469953 |
| *si-TD181* | *0.224999* |
| si-TD217 | 0.414913 |
| si-TD221 | 0.462056 |
| si-TD224 | 0.490381 |
| si-TD358 | 0.387057 |
| *si-TD362* | *0.288363* |
| *si-TD364* | *0.275357* |
| si-TD370 | 0.445778 |
| si-TD372 | 0.459658 |
| si-TD376 | 0.387624 |
| *si-TD378* | *0.295441* |
| si-TD380 | 0.400417 |
| si-TD443 | 0.396858 |
| si-TD451 | 0.311861 |
| si-TD480 | 0.460598 |
| si-TD483 | 0.377209 |
| si-TD508 | 0.476182 |
| si-TD509 | 0.468754 |
| si-TD577 | 0.424962 |
| si-TD585 | 0.448536 |
| si-TD587 | 0.410307 |
| si-TD588 | 0.441516 |
| si-TD596 | 0.497351 |
| si-TD598 | 0.422082 |
| si-TD600 | 0.487359 |
| si-TD604 | 0.401307 |
| si-TD607 | 0.375209 |
| si-TD609 | 0.476541 |
| si-TD611 | 0.457187 |
| si-TD717 | 0.467227 |
| si-TD718 | 0.450869 |
| si-TD720 | 0.335688 |
| si-TD723 | 0.411798 |
| *si-TD726* | *0.270674* |

TABLE 2-continued siRNA with interference efficiency of 50% and above

| SIRNA Sequence | Normalized target gene relative expression value |
|---|---|
| *si-TD730* | *0.252773* |
| si-TD734 | 0.48745 |
| si-TD736 | 0.416718 |
| si-TD743 | 0.471836 |
| si-1 | 0.506191 |
| si-7 | 0.373945 |

Example 3. Identification of Candidate siRNA by Dual Luciferase Assay

In this example, candidate siRNA sequences obtained in Example 2 were further identified by a dual luciferase assay.

1. Constructing Target Gene CKIIP-1 Overexpression Vector

The sequence fragment of CKIP-1 CDS 1-652 was amplified by PCR using upstream and downstream primers with SadI and XhoJ restriction enzyme cutting sites and protective bases, respectively. The amplification product was digested by SadI and XhoJ and then inserted into a pGP-miRGLO overexpression vector (see FIG. 2) which was also digested by SadI and XhoJ to obtain the pmirGlo-CDS1 carrier overexpressing the sequence of the first segment (1-652) of the CDS region of CKIP-1 gene.

The sequence fragment of CKIP-1 CDS 653-1230 was amplified by PCR using upstream and downstream primers with SadI and XhoJ restriction enzyme cutting sites and protective bases, respectively. The amplification product was digested by SadI and XhoJ and then inserted into a pGP-miRGLO overexpression vector (see FIG. 2) which was also digested by SadI and XhoJ to obtain the pmirGlo-CDS2 carrier overexpressing the sequence of the second segment (653-1230) of the CDS region of CKIP-1 gene.

2. Cell Culture 293T cells were regularly cultured in DMEM medium (Gibco) containing 10% FBS (Gibco) (containing 1.5 mM L-glutamine, 100 U/ml penicillin, 100 μg/ml streptomycin) in an incubator with 5% CO2 saturated humidity under 37° C.

3. Transfection of Cells

When 293T cells were cultured until 80-90% confluence in a 10 cm dish, the medium was decanted, and the cells were washed twice with 3 ml PBS. 1 ml of Trypsin-EDTA solution was added, mixed well, carefully aspirated the pancreatin solution and placed at 37° C. for 2-3 minutes. 2 ml complete medium was added and the cells were pippeted to form a single cell suspension. The cells were counted and seeded in 24-well plates at approximately 1×10$^5$ cells per well.

150 μl of Opti-MEMI (50 l/well*3) was added to a 1.5 ml EP tube, followed by adding 30 ng of the corresponding plasmid (10 ng per well) and the corresponding amount of siRNA (each siRNA final concentration setting gradient: 6.25, 12.5, 25, 50, 100, 300 nM, the final concentration of the negative control NC-7 is 25 nM), and mixing well; another 1.5 ml EP tube was filled with 150 μl of Opti-MEMI (50 μl/well*3) and 6 μl of transfection reagent Lipo2000, mixed well, left standstill for 5 min and then mixed well in a volume of 300 ul for 20 min at room temperature. The culture medium was removed from the 24-well plate prepared on the previous day, and 400 μl/well culture medium was added; after being left standstill for 20 min, the transfection mixture was added to the above 24-well plate by 100 μl/well, with each 3 replicates, Blank wells and Mock wells were set, the plates were shaken well and incubated in an incubator for 6 hours. The transfection liquid was removed, rinsed with PBS, culture medium was added in for continuous culture, and photos of the wells transfected with NC-FAM were taken to observe the transfection efficiency. Cells were collected 24 h after transfection for dual luciferase assay.

4. Dual Luciferase Assay

Experimental materials and reagents: Dual-Luciferase Reporter Assay System (Promega, E1960); PBS; 96-well white plate (corning cat. #3912); Multilabel Microplate Detector (PerkinElmer EnSpire).

Experimental steps: the medium was removed from the cell plates to be examined, the cultured cells were washed with PBS, and the PBS was aspirated and discarded. 1×PLB was added by 100 μl/well, and the plates were slightly shaken at room temperature and lysed for 15 min. The cell lysate was moved into a small centrifuge tube for centrifugation at 3000 rpm for 3 min, cell debris were removed, 30 μl of supernatant was taken, added to a 96-well white plate, and a substrate was added for detection according to the recommended operation steps of the specification.

Results:

Four siRNAs have good inhibition effects on CKIP-1 expression in a dual luciferase assay: si-TD137, si-TD141, si-TD176, and si-7. The results are shown in Tables 3-6 and FIGS. 3-6, respectively.

TABLE 3

Dual luciferase assay results for si-TD137

| | Total mean value of normalized dual luciferase relative activity | Standard deviation | P-value compared with NC7 group |
|---|---|---|---|
| empty vector | 261.5710548 | 96.3502 | |
| empty vector + NC-7 | 252.5532524 | 80.68784 | |
| empty vector + 137-6.25 | 222.8452964 | 63.83427 | |
| empty vector + 137-12.5 | 228.8008311 | 67.97434 | |
| empty vector + 137-25 | 224.1443386 | 70.3993 | |
| empty vector + 137-50 | 233.7895134 | 96.01054 | |
| empty vector + 137-100 | 240.7744442 | 70.31852 | |
| empty vector + 137-300 | 224.4435964 | 65.32518 | |
| CDS1 | 100 | 0 | |
| CDS1 + NC-7 | 97.47065705 | 27.59265 | |
| CDS1 + 137-6.25 | 12.30603204 | 2.139099 | 0.005965 |
| CDS1 + 137-12.5 | 10.86442887 | 2.108049 | 0.005615 |
| CDS1 + 137-25 | 10.28528737 | 1.054173 | 0.005438 |
| CDS1 + 137-50 | 9.281597349 | 2.315117 | 0.005271 |
| CDS1 + 137-100 | 10.82386854 | 1.645889 | 0.005582 |
| CDS1 + 137-300 | 7.593906894 | 3.041176 | 0.004967 |

TABLE 4

Dual luciferase assay results for si-TD141

| | Total mean value of normalized dual luciferase relative activity | Standard deviation | P-value compared with NC7 group |
|---|---|---|---|
| empty vector | 232.9723364 | 61.66293 | |
| empty vector + NC-7 | 205.4147266 | 20.38412 | |
| empty vector + 141-6.25 | 215.5570016 | 37.7184 | |
| empty vector + 141-12.5 | 210.1388575 | 23.7144 | |
| empty vector + 141-25 | 217.6250075 | 31.30451 | |
| empty vector + 141-50 | 195.7261375 | 45.5828 | |
| empty vector + 141-100 | 225.8556173 | 53.21314 | |
| empty vector + 141-300 | 194.396959 | 47.47294 | |
| CDS1 | 100 | 0 | |
| CDS1 + NC-7 | 95.13464683 | 19.17207 | |
| CDS1 + 141-6.25 | 16.98508418 | 2.229641 | 0.002177 |
| CDS1 + 141-12.5 | 14.2576769 | 3.90799 | 0.002015 |
| CDS1 + 141-25 | 12.61787894 | 3.959899 | 0.001872 |
| CDS1 + 141-50 | 12.64749866 | 2.563133 | 0.001791 |
| CDS1 + 141-100 | 12.05755431 | 0.886328 | 0.001693 |
| CDS1 + 141-300 | 8.134042105 | 2.163326 | 0.00145 |

TABLE 5

Dual luciferase assay results for si-TD176

| | Total mean value of normalized dual luciferase relative activity | Standard deviation | P-value compared with NC7 group |
|---|---|---|---|
| empty vector | 259.3844179 | 14.91878 | |
| empty vector + NC-7 | 253.6837275 | 24.80359 | |
| empty vector + 176-6.25 | 232.3986339 | 17.01937 | |
| empty vector + 176-12.5 | 199.7533446 | 2.950685 | |
| empty vector + 176-25 | 218.9236568 | 32.63606 | |
| empty vector + 176-50 | 203.8520998 | 31.30066 | |
| empty vector + 176-100 | 219.0134189 | 30.88615 | |
| empty vector + 176-300 | 186.6665828 | 16.72755 | |
| CDS1 | 100 | 0 | |
| CDS1 + NC-7 | 94.53375651 | 4.874274 | |
| CDS1 + 176-6.25 | 21.31523373 | 1.321383 | 1.49E-05 |
| CDS1 + 176-12.5 | 21.95335577 | 2.282599 | 1.99E-05 |
| CDS1 + 176-25 | 20.89875168 | 1.167482 | 1.42E-05 |
| CDS1 + 176-50 | 19.27982377 | 0.247705 | 1.17E-05 |
| CDS1 + 176-100 | 21.66118398 | 3.755765 | 3.34E-05 |
| CDS1 + 176-300 | 18.16630661 | 1.603929 | 1.35E-05 |

TABLE 6

Dual luciferase assay results for si-7

| | Total mean value of normalized dual luciferase relative activity | Standard deviation | P-value compared with NC7 group |
|---|---|---|---|
| empty vector | 161.0586219 | 66.14465 | |
| empty vector + NC-7 | 164.50757 | 62.34558 | |
| empty vector + si7-6.25 | 169.6545487 | 57.58843 | |
| empty vector + si7-12.5 | 170.6842599 | 53.23935 | |
| empty vector + si7-25 | 162.2483155 | 54.75665 | |
| empty vector + si7-50 | 171.4671143 | 51.29689 | |
| empty vector + si7-100 | 172.0681778 | 62.19204 | |
| empty vector + si7-300 | 163.0764404 | 51.25441 | |
| CDS2 | 100 | 0 | |
| CDS2 + NC-7 | 99.61211154 | 15.69399 | |
| CDS2 + si7-6.25 | 17.29806814 | 2.382198 | 0.00085 |
| CDS2 + si7-12.5 | 18.13340456 | 1.80696 | 0.000868 |
| CDS2 + si7-25 | 17.09295528 | 1.84478 | 0.000828 |
| CDS2 + si7-50 | 18.07601932 | 0.777867 | 0.000848 |
| CDS2 + si7-100 | 17.5441839 | 3.941363 | 0.000926 |
| CDS2 + si7-300 | 15.54928456 | 3.365782 | 0.000819 |

Example 4. siRNA Targeting CKIP-1 Inhibits Expression of Pro-Inflammatory Cytokine RAW264.7 mouse peritoneal macrophage cell line (purchased from Cell Bank of Chinese Academy of Sciences, Shanghai) was cultured in complete DMEM medium containing 10% fetal bovine serum, 100 U penicillin and streptomycin, and cultured overnight in an incubator under 37° C. constant temperature carbon dioxide (5%) until cell confluence reached 70-80%.

In vitro, mouse macrophages transfected with the small interfering RNAs against CKIP-1 prepared as described above or their modified forms having methoxy group modification on sense strand were used as a drug treatment group (RNAi group), and the cells treated with the transfection reagent X-TremeGENE siRNA transfection reagent alone (commercially available from Roche, article number 4476093001) were used as a transfection reagent group (MOCK group), 3 in each group in parallel, at least three times for each experiment. For transfection of mouse macrophages, the final concentration of small interfering RNA was 30 nM. 24 hours after transfection, LPS (commercially available from Sigma, Cat. No. L2630-10MG) was added to stimulate for 6 hours, supernatants of cells of each group were collected, secretion of proinflammatory cytokines was detected, and mRNA expression levels of proinflammatory cytokines were detected by collecting cells of each group.

1. Determination of TNF-α and IL-6 Protein Secretion Inhibition Efficiency by siRNA Inhibition efficiency of the secretion levels of TNF-α and IL-6 in the cell supernatant was determined by an ELISA method, specifically: Mouse TNF alpha ELISA Ready-SET-Go!® (eBioscience, Cat. No. 88-7324-88) and Mouse IL-6 ELISA Ready-SET-Go! (eBioscience, Cat. No. 88-7064-88) kits were used according to the instructions, and the concentrations of TNF-α and IL-6 were calculated by plotting standard curves.

Cytokine inhibition efficiency was calculated as follows:

Cytokine inhibition efficiency=[($LPS$ group-treated group)/($LPS$ group-blank control group)]×100%.

The results of the determination are shown in Tables 7 and 8 below:

TABLE 7

|  |  | Inhibition (%) of TNFα secretion | Inhibition of IL-6 secretion (%) |
|---|---|---|---|
| MOCK group | Transfection reagent | 3.71 | 29.81 |
| RNAi group | si-7 | 32.23 | 77.13* |
|  | si-137 | 25.95 | 55.58* |
|  | si-141 | 21.49 | 65.30* |
|  | si-176 | 17.75 | 56.69* |

Note:
*P < 0.05, compared with MOCK group, there was statistically significant difference.

TABLE 8

|  |  | Inhibition (%) of TNFα secretion | Inhibition of IL-6 secretion (%) |
|---|---|---|---|
| MOCK group | Transfection reagent | 1.28 | 21.62 |
| RNAi group | si-7-Ome | 35.51 | 89.75* |
|  | si-137-Ome | 26.30 | 84.51* |
|  | si-141-Ome | 27.95 | 87.85* |
|  | si-176-Ome | 21.10 | 80.12* |

Notes:
*P < 0.05, compared with MOCK group, there was statistically significant difference.

As can be seen from the above table, each candidate siRNA and its methylation modified form inhibited LPS-induced IL-6 and TNF-α secretion from RAW264.7 mouse macrophages, and the inhibition of IL-6 secretion reached a significant level.

2. Determination of TNF-α and IL-6 mRNA Expression Inhibition Efficiency by siRNA TNF-α and IL-6 mRNA levels in the collected RAW264.7 cells were detected by a real-time fluorescence quantitative PCR (real-time PCR) method, specifically: total cellular RNA was extracted using TRIzol reagent (Invitrogen, article number 15596018), cDNA was synthesized by reverse transcription using TransScriptAll-in-One First-Strand cDNA Synthesis SuperMixforq PCR (One-Step DNA Removal) (TransGen, article number AT341-02) kit, and the inhibitory efficiency of siRNA on LPS-induced IL-6 and TNF-α expression in murine peritoneal macrophages was detected by fluorescence quantitative PCR.

The GAPDH gene was used as an internal reference gene in the Real-time PCR method, and the primer sequences were shown in Table 9

TABLE 9

|  | Forward (5'-3') | Reverse (5'-3') |
|---|---|---|
| Mice TNF-α | TCAGCGAGGACAGCAAGG | AGTGAGTGAAAGGGACAGAACC |
| Mice IL-6 | CCTTCTTGGGACTGATGCTG | TTGGGAGTGGTATCCTCTGTGA |
| Mice GAPDH | CCTTCATTGACCTCAACTACATGG | CTCGCTCCTGGAAGATGGTG |

In the fluorescence quantitative PCR method, the nucleic acid inhibition efficiency is calculated according to the following equation:

siRNA inhibition efficiency=[(LPS group cytokine gene copy number/LPS group GAPDH gene copy number-treatment group cytokine gene copy number/treatment group GAPDH gene copy number)/(LPS group cytokine gene copy number/LPS group GAPDH gene copy number-blank control group cytokine gene copy number/blank control group GAPDH gene copy number)]×100%

The results are shown in Table 10:

TABLE 10

|  |  | Inhibition (%) of TNFα secretion | Inhibition of IL-6 secretion (%) |
|---|---|---|---|
| MOCK group | Transfection reagent | 11.13 | 11.96 |
| RNAi group | si-7 | −4.6 | 70.75* |
|  | si-137 | 6.64 | 40.78* |
|  | si-141 | −1.58 | 54.53* |
|  | si-176 | 6.80 | 45.76* |

Notes:
*P < 0.05, compared with MOCK group, there was statistically significant difference.

As can be seen from Table 10, each candidate siRNA significantly inhibited LPS-induced IL-6 mRNA expression in mouse macrophages; there was no significant inhibitory effect on TNF-α mRNA expression.

It can be seen that the CKIP-1 targeting siRNAs of the present invention can inhibit the levels of the pro-inflammatory cytokines IL-6 and TNF-α, particularly IL-6, thereby inhibiting inflammation, particularly inflammation associated with IL-6 and/or TNF-α, such as inflammation in RA.

Example 5. Inhibitory Effect of siRNA Targeting CKIP-1 on CKIP-1 Protein Expression Human osteoblast cell line hFOB1.19 purchased from the Chinese Academy of Sciences cell bank was cultured in DMEM-F12 medium containing 10% fetal bovine serum (purchased from Gibco). Human osteoblast hFOB1.19 was transferred to 24-well plates for overnight culture for adhesion. Human osteoblast hFOB1.19 transfected with siRNA targeting CKIP-1 was used as treatment group, and the cells transfected with non-specific nucleic acid were used as negative control group (NC group). Each group with 2 duplicates was repeated at least 3 times. Human osteoblast cells were transfected with a final nucleic acid concentration of 20 μM. After 72 hours of transfection, cells were collected and assayed for CKIP-1 protein expression.

The content of CKIP-1 protein in osteoblast cells was detected by immunoblotting according to the method in the literature (Molecular Cloning A Laboratory Manual, Science Press, 2005). The CKIP-1 antibody used for immunoblotting was purchased from Santa Cruz Biotechnology (Cat. No. sc-376355) and the internal reference antibody was GADPH (purchased from Santa Cruz Biotechnology, Cat. No. sc-166574).

In immunoblotting, nucleic acid inhibitory activity was calculated as follows: nucleic acid inhibitory activity=[1−(light intensity value of CKIP-1 Western blot band of treatment group/light intensity value of GAPDH Western blot band of treatment group)/(light intensity value of CKIP-1 Western blot band of control group/light intensity value of GAPDH Western blot band of control group)]×100%.

Result: the expression of CKIP-1 in hFOB1.19 cells was significantly inhibited by si-7. Compared with control NC, there was significant difference (P<0.05). The determined results are shown in Table 11.

TABLE 11

|  | Inhibition rate (%) of CKIP-1 protein expression |
|---|---|
| NC | 0.0 |
| si-7 | 74.5* |

Example 6. Effect of siRNA Targeting CKIP-1 on Osteoblast Differentiation

Similar to Example 5, CKIP-1 siRNA was tested for mRNA expression levels of human osteoblast hFOB1.19 phenotypic gene alkaline phosphatase (ALP), type I collagen (COL1), osteopontin (OPN), bone sialoprotein (BSP) and osteocalcin (OC) over time using primers as shown in Table 12. The determined results are shown in Table 13.

TABLE 12

| Gene | Primer sequence (5'-3') Forward | Reverse | Product Size | Tm | Genbank No. |
|---|---|---|---|---|---|
| HumanALP | GTCAGCTCCACC ACAACCCT | GCCCTCATTGGC CTTCACCC | 155 | 60 | NM_000478.3 |
| HumanCOL1 | CACTGGTGATGC TGGTCCTG | CGAGGTCACGG TCACGAAC | 179 | 60 | NM_000088.3 |
| HumanOPN | GTACCCTGATGC TACAGACG | TTCATAACTGTC CTTCCCAC | 139 | 60 | NM_001040060.1 |
| HumanBSP | GGCACCTCGAA GACAACAAC | GCCCGTGTATTC GTACTCCC | 135 | 60 | NM_004967.3 |
| HumanOC | AGGGCAGCGAG GTAGTGAAG | TGTGGTCAGCC AACTCGTCA | 138 | 60 | NM_199173.3 |
| HumanGAPDH | GGCATGGACTGT GGTCATGAG | TGCACCACCAA CTGCTTAGC | 87 | 60 | NM_002046.3 |

TABLE 13

|  | Increasing rate of ALP mRNA (%) | Increasing rate of COL1 mRNA (%) | Increasing rate of OPN mRNA (%) | Increasing rate of BSP mRNA (%) | Increasing rate of OC mRNA (%) |
|---|---|---|---|---|---|
| NC | 0 | 0 | 0 | 0 | 0 |
| si-7 | 86.5* | 70.2* | 93.0* | 171.6* | 85.11* |

*P < 0.05, compared with NC group, there was statistical difference.

Result: ALP, COL1A1 and OPN begin to express at the early stage of osteoblast differentiation, while BSP and OC begin to express at the mature stage of osteoblast. After 72 hours of action, the expression of ALP, COL 1, OPN, BSP and OC in si-7 group were significantly higher than that in NC group.

The experimental results show that the siRNA targeting CKIP-1 can increase the expression of the phenotypic genes of the human osteoblast cell line hFOB1.19, thereby promoting osteoblast differentiation.

Example 7. Effect of siRNA Targeting CKIP-1 on Bone Matrix Mineralization Deposition Rate Calcium deposition is a key functional mineralization marker for mature osteoblasts during osteoblast formation in vitro. As described above, the human osteoblast cell line hFOB1.19 transfected with siRNA targeting CKIP-1 was used as a treatment group, and the cells transfected with non-specific nucleic acid were used as a negative control group (NC group). The final nucleic acid concentration for transfection was 20 PM. The frequency of interval transfection was once a week, with 4 duplicates per group in parallel. Calcium deposition in human osteoblast cell line hFOB1.19 was determined by calcium staining 7, 14 and 21 days after the first transfection.

The results are shown in Table 14. 21 days after the first transfection of the human osteoblast cells, the calcium deposition of the treatment group is obviously higher than that of the NC group, which at the functional level verifies that the siRNA can promote the differentiation of human preosteoblasts into mature osteoblasts.

TABLE 14

|  |  | Calcium deposition in human osteoblasts (ng/μg protein) |
|---|---|---|
| NC Group | Non-specific nucleic acid | 0.00 |
| Treatment group | si-7 | 64.81* |

*P < 0.05: compared with NC group, there was statistical difference.

Example 8. Assessment of siRNA Activity In Vivo Using a Mice CIA Model

Collagen-induced arthritis (CIA) model was established in 8-10 week old male DBA mice by subcutaneous injection of type II collagen at the root of the tail. The specific method is as follows: a proper amount of bovine type II collagen with a concentration of 2 mg/mL was mixed with an equivalent amount of incomplete Freund's adjuvant, fully emulsified, and the emulsified mixture was injected subcutaneously at the root of the tail with 100 μg of type II collagen/mouse. After 21 days, 50 μg of type II collagen was injected subcutaneously once at the root of the tail for boost.

5-grade semi-quantitative evaluation standard was taken as the evaluation standard of arthritis clinical severity: 0: no red swelling; 1: erythema accompanied with moderate swelling and confined to the midfoot or ankle; 2: moderate swelling extended from the ankle to the midfoot; 3: moderate swelling extended from the ankle joint to the metatarsal joint; 4: severe swelling of ankle, foot and toes.

The animals were randomly grouped if the severity of the double hindlimbs of each group of animals was scored about 1 through visual evaluation: carrier group, ankle joint cavity was injected with blank liposome; NC (negative control) group, liposomes loaded with negative control sequences were injected into the ankle joint cavity; the treatment group, liposomes loaded with Si-7, Si-137, Si-141 or Si-176 were injected into ankle joint cavity; the positive control group was administered with the positive drug Etanercept (purchased from Shanghai CP Guojian Pharmaceutical Co., Ltd., each containing 12.5 mg of active ingredient).

The animals in each group were administered by injecting into the bilateral ankle joint cavities of the hind limbs at a dose of 4 μg siRNA/5 μl liposome/ankle joint, six times on day 0, day 7, day 14, day 21, day 28 and day 35. The positive drug was administered by subcutaneous injection at a dose of 7.5 mg/kg body weight.

1. Effect of siRNA Treatment on Clinical Score and Body Weight of CIA Mice

Figure 7:
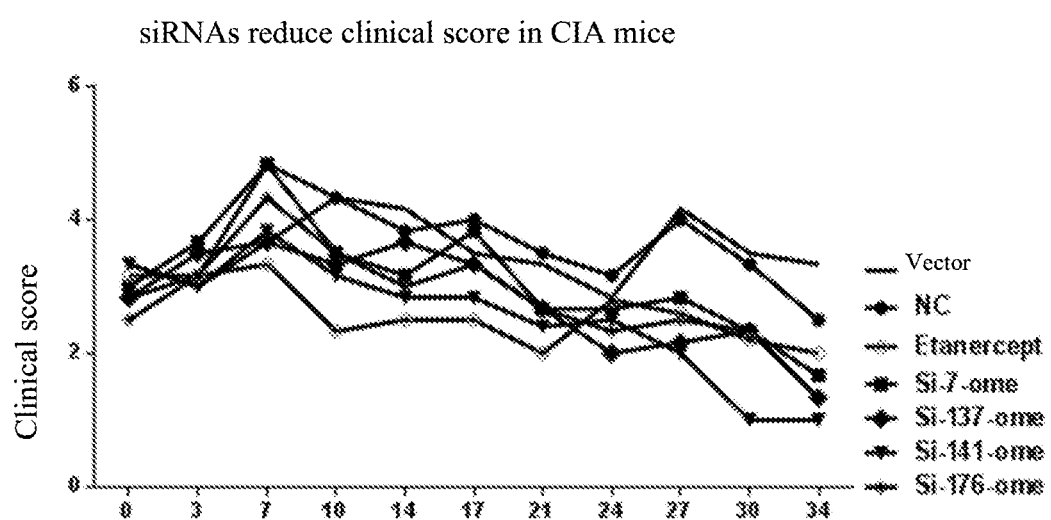
FIG. 7 shows that siRNAs decrease CIA mouse clinical score.
Figure 8:
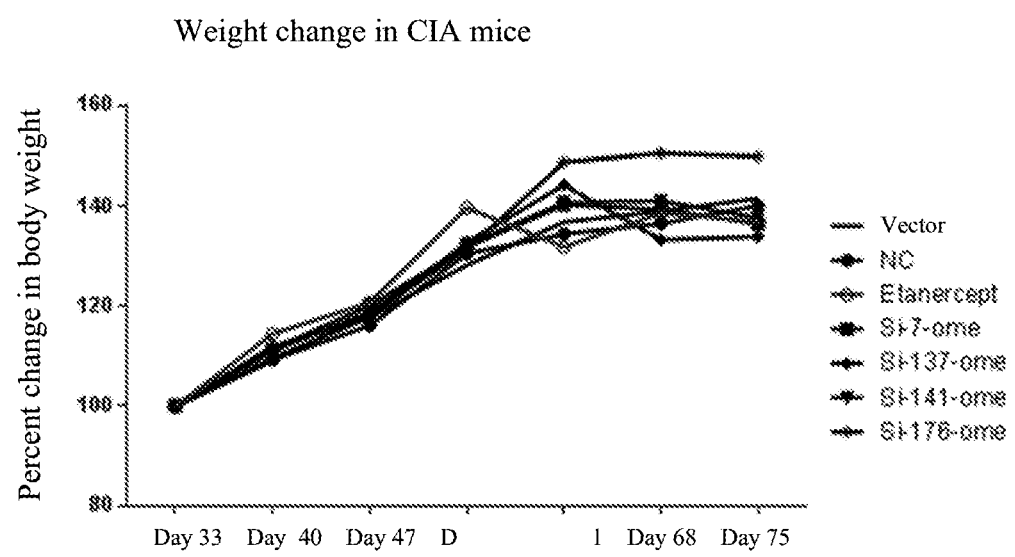
FIG. 8 shows body weight changes in CIA mice after siRNA treatment.

The scores for swelling in the ankle joint of both hind limbs of mice were observed and recorded from the day of start twice a week, and the scores for the ankle joint of both hind limbs were added for statistical analysis. Clinical scoring results are shown in FIG. 7 and Table 15 below. Meanwhile, the body weight of the mice was recorded once a week, and the results are shown in FIG. 8 and Table 16.

The results showed that the body weight of each group of mice increased without weight loss. Si-7-Ome, Si-137-Ome, Si-141-Ome, and Si-176-Ome all significantly reduced the clinical score of mice CIA model arthritis, the inhibition rates were 50%, 60%, 70% and 60%, respectively, and the effects were better than the positive drug Etanercept (inhibition 40%).

TABLE 15

Inhibition of mice CIA clinical scores

| | Grouping | Mice CIA clinical score | Inhibition rate of mice CIA clinical score (%) |
|---|---|---|---|
| Carrier groups | Carrier | 3.33 | |
| NC group | Nonspecific nucleic acid | 2.50 | 24.99 |
| PC group | Etanercept | 2.00 | 39.99 |
| Treatment group | Si-7-Ome | 1.67* | 49.98 |
| | Si-137-Ome | 1.33** | 60.01 |
| | Si-141-Ome | 1.00*** | 70.00 |
| | Si-176-Ome | 1.33** | 60.01 |

Notes:
*indicates P < 0.05 as compared with the carrier groups,
**indicates P < 0.01 as compared with the carrier groups,
**indicates P < 0.001 as compared with the carrier groups.

TABLE 16

Effect on body weight change in mice

| | | Day 0 | Day 42 | Weight change rate (%) of CIA mice |
|---|---|---|---|---|
| Carrier groups | Carrier | 16.8 | 23.7 | 141.1 |
| NC group | Nonspecific nucleic acid | 17.4 | 24.3 | 139.7 |
| PC group | Etanercept | 16.6 | 23.0 | 138.6 |
| Treatment group | Si-7-OMe | 16.4 | 22.4 | 136.6 |
| | Si-137-OMe | 16.0 | 21.6 | 135.0 |
| | Si-141-OMe | 15.6 | 21.7 | 139.1 |
| | Si-176-OMe | 15.9 | 24.0 | 150.9 |

2. Effect of siRNA on Expression of Proinflamimatory Factors in Joint Tissue of CIA Mice After sacrifice, the fur of CIA model mice was cut off from the legs with scissors, so that the ankle joint was exposed, the portion below knee joint was cut off with forceps, cooled with liquid nitrogen, grinded and transferred to an enzyme-free tube, and total cellular RNA was extracted using TRIzol reagent (Invitrogen, article number 15596018). cDNA was synthesized by reverse transcription using TransScript All-in-One First-Strand cDNA Synthesis SuperMix for qPCR (One-Step gDNA Removal) (TransGen, article number AT341-02) kit. The inhibitory effects of si-7, si-137, si-141 and si-176 on CKIP-1, IL-6, TNF-α and IL-17A mRNA expression in joint tissue of CIA mouse model were detected by fluorescence quantitative PCR.

Primers for IL-6, TNF-α, and the reference gene GAPDH as described above were used. The CKIP-1, IL-17A primer sequences are shown in Table 17:

TABLE 17

| | Forward (5'-3') | Reverse (5'-3') |
|---|---|---|
| Mice IL-17A | CTCCACCGCAATGAAGACC | CCCTCTTCAGGACCAGGATC |
| Mice CKIP-1 | TTTCTCGGCCTTGGGAAAAAC | GAGGCACATCGGCTCTTCT |

In the fluorescent quantitative PCR method, the expression inhibition efficiency is calculated as follows:

Inhibition efficiency=[(cytokine gene copy number of the carrier groups/GAPDH gene copy number-treatment group cytokine gene copy number of the carrier groups/GAPDH gene copy number of the treatment groups)/(cytokine gene copy number of the carrier groups/GAPDH gene copy number-cytokine gene copy number of the normal control groups/GAPDH gene copy number of the normal control groups)]× 100%

Figure 9:
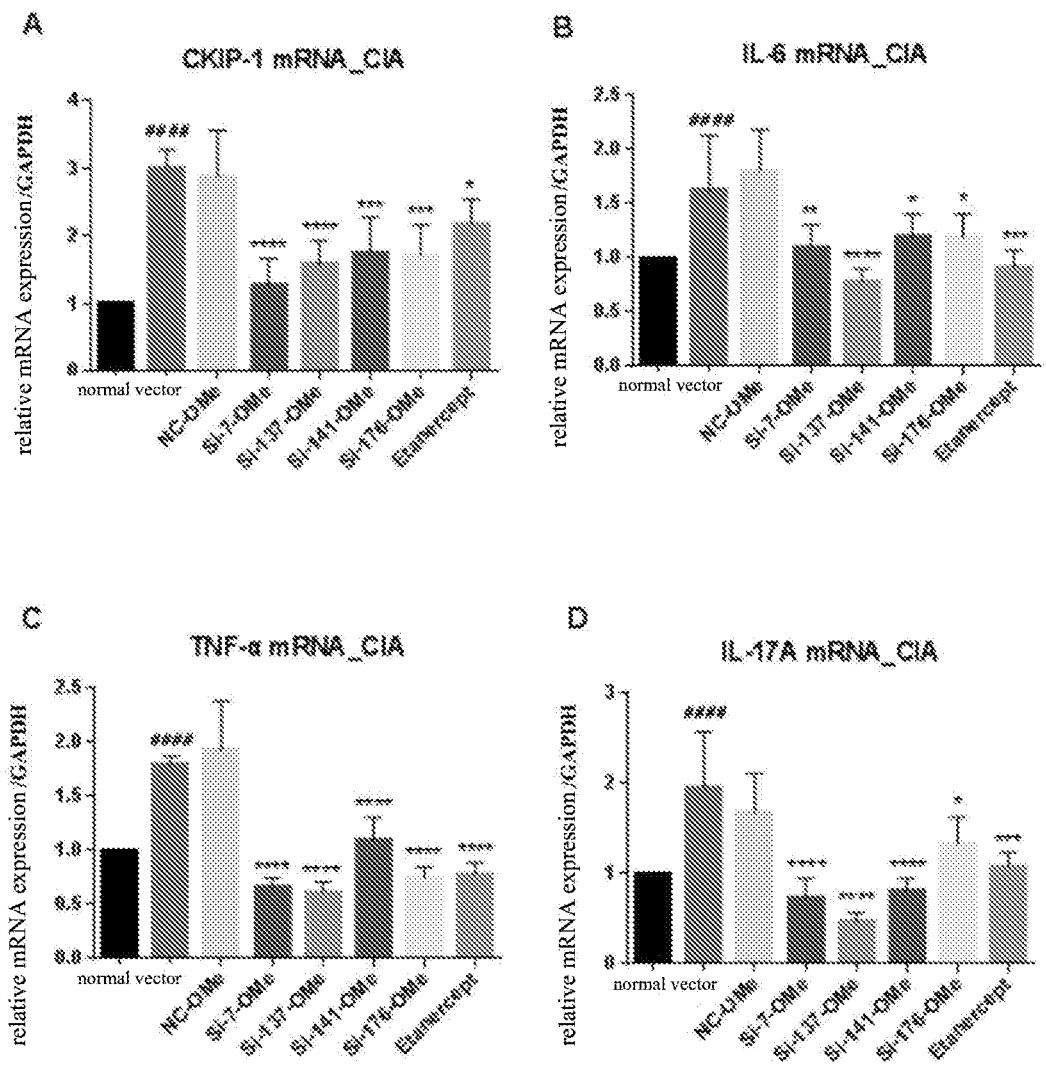
FIG. 9 shows that siRNAs affect proinflammatory cytokine expression in joint tissue of CIA mice.

The results of the determination are shown in Table 18 and FIG. 9:

TABLE 18

|  |  | Inhibition rate of CKIP-1 mRNA (%) | Inhibition rate of IL-6 mRNA (%) | Inhibition rate of TNF-α mRNA (%) | Inhibition rate of IL-17A mRNA (%) |
|---|---|---|---|---|---|
| Carrier groups | Empty liposome | 0 | 0 | 0 | 0 |
| NC group | Non-specific nucleic acid | 7.10 | −28.46 | −16.43 | 29.42 |
| Positive control group | Etanercept | 41.37* | 113.83*** | 127.36**** | 92.10*** |
| Treatment group | Si-7-OMe | 86.60* | 83.17** | 142.72**** | 126.59**** |
|  | Si-137-OMe | 70.83* | 135.84**** | 147.90**** | 154.57**** |
|  | Si-141-OMe | 62.04*** | 68.85* | 88.25**** | 118.81**** |
|  | Si-176-OMe | 65.02*** | 68.85* | 131.98**** | 65.53* |

Notes:
*$P < 0.05$, compared with carrier group, there was statistically significant difference;
**$P < 0.01$, compared with carrier group, there was statistically significant difference;
***$P < 0.001$, compared with carrier group, there was statistically significant difference;
****$P < 0.0001$, compared with carrier group, there was statistically significant difference;
$P < 0.0001$ compared with the normal control group, there was statistically significant difference.

It can be seen that si-7-OMe, si-137-OMe, si-141-OMe, si-176-OMe all significantly inhibited the expression of CKIP-1, IL-6, TNF-α, IL-17AmRNA in the joint tissues of CIA mice, with inhibition rates more than 50%, and the inhibition of CKIP-1 mRNA was stronger than that of the positive drug Etanercept (41.37%). Compared with other small interfering RNAs, si-137 showed a stronger inhibitory effect on pro-inflammatory factors IL-6, TNF-α, IL-17AmRNA, and the inhibitory effect was stronger than that of the positive drug Etanercept. The siRNAs of the present invention are shown to be effective in inhibiting inflammation in RA.

3. Micro CT Detection

Scancoviva CT 40 was used for the micro-CT detection. A mouse hind paw was put into a Micro CT sample tube for three-dimensional CT scanning and reconstruction. After the scanning, a matched software was used for analyzing the three-dimensional microstructure of the trabeculae and collecting the spatial structure parameters of the trabeculae.

4. Pathological Examination

The hind limbs of mice were fixed in 4% formaldehyde solution and embedded with paraffin after EDTA decalcification. The pathological changes of joints and bone erosion were examined through serial section and HE staining.

5. Bone Morphometric Analysis

Mice were intraperitoneally injected with xylenol orange (90 mg/kg) 12 days before sacrifice and intraperitoneally injected with calcein (10 mg/kg) 2 days before sacrifice. After sacrifice, hind paws were removed and 10 μm discrete sections were made using a non-decalcifying microtome. Sections were stained with 1% methylene blue followed by light microscopy and unstained sections were used for fluorescence microscopy. The metatarsal bones in the paws were used for bone morphometric analysis.

Compared with the control group, each siRNA administration group played an positive role in improving inflammation and bone injury of a rheumatoid arthritis model and delaying disease progress, exhibiting good therapeutic effect.

Example 9. Validation of Effect of the siRNAs with Monkey Rheumatoid Arthritis Model 1. Animal Modeling and Administration 3-6-year-old female cynomolgus monkeys were immunized with bovine type II collagen on day 0 and day 21, respectively, according to modeling methods of collagen-induced arthritis described in related literatures. The drug is locally administered into the joint after the onset of the disease. Liposome delivery systems were used for the small nucleic acids.

Grouping is as follows: as for the carrier groups, empty liposomes were injected into the joint cavity; as for NC (negative control) groups, liposomes loaded with negative control sequences were injected into ankle joint cavity; as for the treatment group, liposomes loaded with Si-7, Si-137, Si-141 or Si-176 were injected into the articular cavity; as for the positive control group, the positive drug etanercept (purchased from Shanghai CP Guojian Pharmaceutical Co., Ltd.) was administered. Three animals in each group were administered by articular injection once a week for 6 weeks.

2. Detection of Parameters

MicroCT, pathology, bone morphometry and other tests were similar to experiments in mice.

Compared with the control group, the siRNA administration group showed good treatment effects on improving disease condition, especially reducing bone damage, maintaining bone function and the like in a rheumatoid arthritis model.

What we claim is:

1. A pharmaceutical composition suitable for inhibiting casein kinase interacting protein 1 (CKIP-1) expression in a human subject in need thereof, which comprises:
   (i) an amount of a double-stranded RNA (dsRNA) molecule comprising a sense strand shown in SEQ ID NO: 71 and an antisense strand shown in SEQ ID NO: 72 effective to inhibit the expression of CKIP-1 in a human subject in need thereof; and
   (ii) a pharmaceutically acceptable carrier;
   wherein said composition when administered to a human subject in need thereof is capable of inhibiting CKIP-1 expression.

2. The pharmaceutical composition of claim 1, wherein the sense and/or antisense strand additionally has an overhang of at least one nucleotide at the 3' end.

3. The pharmaceutical composition of claim 2, wherein the sense and/or antisense strand additionally has an overhang of 2 nucleotides at the 3' end.

4. The pharmaceutical composition of claim 1, wherein the sense strand and the antisense strand comprise 1 or 2 nucleotide substitutions located within 6, 5, 4, 3 or 2 nucleotides from the 5' and/or 3' end.

5. The pharmaceutical composition of claim 4, wherein the sense and antisense strands comprise 1 nucleotide substitution, which is located at the last nucleotide of the 3' end of the sense strand and correspondingly at the first nucleotide of the 5' end of the antisense strand.

6. The pharmaceutical composition of claim 1, comprising at least one modified nucleotide.

7. The pharmaceutical composition of claim 6, wherein the modified nucleotide is selected from the group consisting of: 2'-O-methyl modified nucleotides, 2'-F modified nucleotides, nucleotides containing 5'-phosphorothioate groups and end nucleotides linked to cholesteryl derivatives or dodecanoic acid bisdecylamide groups, 2'-deoxy-2'-fluoro modified nucleotides, 2'-deoxy-modified nucleotides, locked nucleotides, abasic nucleotides, 2'-amino-modified nucleotides, 2'-alkyl-modified nucleotides, morpholino nucleotides, phosphoramidates and nucleotides containing non-natural bases.

8. The pharmaceutical composition of claim 6, wherein the 2' hydroxyl groups of all nucleotides with uracil or cytosine bases in the sense and/or antisense strands are modified with methoxy groups.

9. The pharmaceutical composition of claim 1, wherein it is an siRNA or shRNA.

10. The pharmaceutical composition of claim 1, wherein it
   1) inhibits CKIP-1 expression by at least 50%; and/or
   2) inhibits the expression of at least one pro-inflammatory cytokine.

11. The pharmaceutical composition of claim 3, wherein the overhang is TT.

12. The pharmaceutical composition of claim 1, wherein it
   1) inhibits CKIP-1 expression by at least 70%; and/or
   2) inhibits the expression of at least one pro-inflammatory cytokine.

13. The pharmaceutical composition of claim 10, wherein said at least one pro-inflammatory cytokine comprises TNF-α, IL-6 and/or IL-17A.

14. The pharmaceutical composition of claim 12, wherein said at least one pro-inflammatory cytokine comprises TNF-α, IL-6 and/or IL-17A.

* * * * *